(12) United States Patent
Dai et al.

(10) Patent No.: US 12,091,401 B2
(45) Date of Patent: Sep. 17, 2024

(54) NITROGEN-HETEROCYCLIC COMPOUND, DISPLAY PANEL AND DISPLAY APPARATUS

(71) Applicant: WuHan TianMa Micro-electronics CO., LTD., Wuhan (CN)

(72) Inventors: Wenpeng Dai, Shanghai (CN); Jinghua Niu, Shanghai (CN); Wei Gao, Shanghai (CN); Lei Zhang, Shanghai (CN); Gaojun Huang, Shanghai (CN)

(73) Assignee: WuHan TianMa Micro-electronics CO., LTD., Wuhan (CN)

( * ) Notice: Subject to any disclaimer, the term of this patent is extended or adjusted under 35 U.S.C. 154(b) by 771 days.

(21) Appl. No.: 16/847,534

(22) Filed: Apr. 13, 2020

(65) Prior Publication Data

US 2021/0261531 A1  Aug. 26, 2021

(30) Foreign Application Priority Data

Feb. 18, 2020 (CN) .......................... 202010099805.1

(51) Int. Cl.
| | | |
|---|---|---|
| C07D 403/04 | (2006.01) | |
| C07D 239/26 | (2006.01) | |
| C07D 401/04 | (2006.01) | |
| C07D 401/14 | (2006.01) | |
| C07D 403/14 | (2006.01) | |
| C07D 405/04 | (2006.01) | |
| C07D 405/14 | (2006.01) | |
| C07D 409/14 | (2006.01) | |
| C07D 471/04 | (2006.01) | |
| C09K 11/00 | (2006.01) | |
| H10K 85/60 | (2023.01) | |

(52) U.S. Cl.
CPC ......... *C07D 403/14* (2013.01); *C07D 403/04* (2013.01); *C07D 405/04* (2013.01); *C07D 405/14* (2013.01); *H10K 85/653* (2023.02); *H10K 85/654* (2023.02); *H10K 85/6572* (2023.02); *H10K 85/6574* (2023.02)

(58) Field of Classification Search
CPC .. C07D 403/04; C07D 403/14; C07D 405/04; C07D 405/14; C07D 239/26; C07D 401/04; C07D 401/14; C07D 409/14; C07D 471/04; H10K 85/653; H10K 85/654; H10K 85/6572; H10K 85/6574; H10K 85/6576; H10K 59/873; H10K 59/879; C09K 11/00; C09K 2211/1011; C09K 2211/1029; C09K 2211/1044; C09K 2211/1059; C09K 2211/1088
See application file for complete search history.

(56) References Cited

FOREIGN PATENT DOCUMENTS

| | | | |
|---|---|---|---|
| CN | 105633118 A | | 6/2016 |
| CN | 109180567 A | | 1/2019 |
| CN | 109535064 | * | 3/2019 |
| CN | 109535064 A | | 3/2019 |
| CN | 111116489 A | | 5/2020 |

OTHER PUBLICATIONS

RN 2222334-71-4, registry database compound, 2019.*
RN1260393-06-3, registry database compound, 2011.*
RN1260393-59-6, registry database compound, 2011.*
RN10198-88-6, registry database compound, 1984.*
Registry No. 1637740-74-9 (Year: 2014).*
First Chinese Office Action mailed on Mar. 3, 2023, issued in corresponding Chinese App. No. 202010099805.1, filed on Feb. 18, 2020, and its English translation thereof, 18 pages.

* cited by examiner

*Primary Examiner* — Sun Jae Yoo
(74) *Attorney, Agent, or Firm* — CHRISTENSEN O'CONNER JOHNSON KINDNESS PLLC

(57) ABSTRACT

Provided are a nitrogen-heterocyclic compound, a display panel and a display apparatus. In an embodiment, the compound has a structure of Chemical Formula 1, in which $X_1$ and $X_2$ are each C or N, and at least one of $X_1$ and $X_2$ is N; $X_3$ to $X_7$ are N or $-CR_a$, and one, two, three or four of $X_3$ to $X_7$ are N, where $R_a$ is hydrogen, deuterium, a substituted or unsubstituted C1-C20 alkyl, C1-C20 alkoxy, C1-C20 thioalkyl, C6-C30 aryl, or C3-C30 heteroaryl; and $R_a$ is independently present or forms an aliphatic ring, an aromatic ring, or a heteroaromatic ring with adjacent carbon atoms; $Ar_1$ and $Ar_2$ are each C6-C30 aryl or C3-C30 heteroaryl; and $L_1$ and $L_2$ are each a single bond, C6-C30 arylene, or C3-C30 heteroarylene. The compound is suitable as a CPL material to improve external quantum efficiency (EQE) of an organic light-emitting device and light-emitting efficiency.

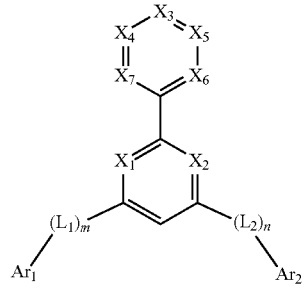

Chemical Formula 1

3 Claims, 2 Drawing Sheets

NITROGEN-HETEROCYCLIC COMPOUND, DISPLAY PANEL AND DISPLAY APPARATUS

CROSS-REFERENCE TO RELATED DISCLOSURES

The present application claims priority to Chinese Patent Application No. 202010099805.1, filed on Feb. 18, 2020, the content of which is incorporated herein by reference in its entirety.

FIELD

The present disclosure relates to the field of organic electroluminescent materials, and particularly, to a compound, a display panel including the nitrogen-heterocyclic, and a display apparatus.

BACKGROUND

Organic light-emitting diodes (OLEDs) have made great progress with decades of development. Although the internal quantum efficiency of OLEDs is close to 100%, the external quantum efficiency is only about 20%. Most of the light emitted by OLED is confined within the light-emitting device due to factors such as substrate mode loss, surface plasma loss, and waveguide effects, thereby resulting in a great energy loss.

In top emission devices, an organic cover layer (Capping Layer, CPL) is deposited on a translucent metal electrode to adjust an optical interference distance, suppress external light reflection, and suppress extinction caused by surface plasma energy movement, thereby improving a light extraction efficiency and a light-emitting efficiency.

The OLEDs have high requirements on performances of CPL materials, such as nearly no absorption in the visible wavelength region (400 nm to 700 nm); high refractive index, with a small extinction coefficient in a wavelength range of 400 nm to 600 nm; and high glass transition temperature and molecular thermal stability (the high glass transition temperature also allows performing vapor-deposition without causing thermal decomposition).

Existing CPL materials are mostly aromatic amine derivatives, phosphoroso derivatives and quinolinone derivatives, which have both hole transmission and electron transmission functions, in order to improve the light extraction efficiency. However, the refractive indexes of the existing CPL materials are generally no greater than 1.9, which cannot meet the requirements on the high refractive index. Amine derivatives having a specific structure with a high refractive index and materials that meet specific parameters can improve the light extraction efficiency, but cannot solve the problem of low light-emitting efficiency (especially for blue light light-emitting devices). Materials known in the related art have a large and loose molecular structure to increase a density of molecules and achieve a high thermal stability, and thus the molecules cannot be compactly stacked. In this regard, many pores are present in the molecular gel during the vapor deposition, which results in a poor coverage. Therefore, it is urgent to develop a new CPL material for improving the performances of OLED devices.

SUMMARY

In view of the problems in the related art, a first aspect of the present disclosure provides a nitrogen-heterocyclic compound having a structure represented by Chemical

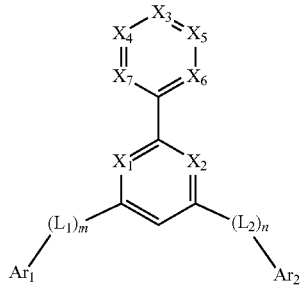

Chemical Formula 1 wherein $X_1$ and $X_2$ are each independently a carbon atom or a nitrogen atom, and at least one of $X_1$ and $X_2$ is N; $X_3$ to $X_7$ are each independently a nitrogen atom or —$CR_a$, wherein one, two, three or four of $X_3$ to $X_7$ are a nitrogen atom, $R_a$ is selected from a group consisting of hydrogen, deuterium, a substituted or unsubstituted C1-C20 alkyl, a substituted or unsubstituted C1-C20 alkoxy, a substituted or unsubstituted C1-C20 thioalkyl, a substituted or unsubstituted C6-C30 aryl, and a substituted or unsubstituted C3-C30 heteroaryl; and $R_a$ is present independently or forms, with adjacent carbon atoms, an aliphatic ring, an aromatic ring, or a heteroaromatic ring;

$Ar_1$ and $Ar_2$ are each independently selected from a group consisting of a substituted or unsubstituted C6-C30 aryl and a substituted or unsubstituted C3-C30 heteroaryl; and $L_1$ and $L_2$ are each independently selected from a group consisting of a single bond, a substituted or unsubstituted C6-C30 arylene, or a substituted or unsubstituted C3-C30 heteroarylene; m is a number of $L_1$, n is a number of $L_2$, and m and n are each an integer independently selected from 1, 2, and 3.

A second aspect of the present disclosure provides a display panel including an organic light-emitting device. In an embodiment, the organic light-emitting device includes an anode, a cathode arranged opposite to the anode, an organic layer located between the anode and the cathode, and a capping layer located at a side of a light exiting side electrode facing away from the organic layer. The light exiting side electrode is the anode or the cathode, the organic layer includes a light-emitting layer, and a material of the capping layer includes the nitrogen-heterocyclic compound according to the first aspect.

A third aspect of the present disclosure provides a display device including the display panel according to the second aspect of the present disclosure.

DESCRIPTION OF EMBODIMENTS

Figure 1:
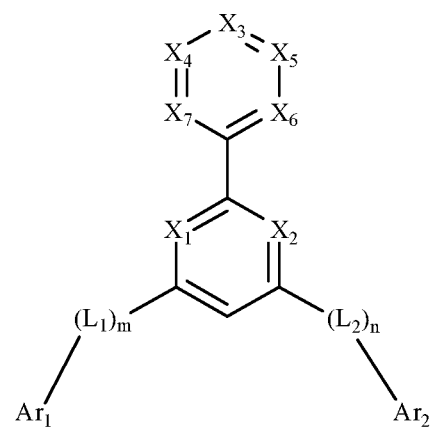
FIG. 1 is a chemical formula of a nitrogen-heterocyclic compound provided by an embodiment of the present disclosure.

The present disclosure is further described through examples and comparative examples. These examples are merely used to illustrate the present disclosure, but the present disclosure is not limited to the following examples. Any modification or equivalent replacement to the embodiments of the present disclosure without departing from the embodiments of the present disclosure should fall within the protection scope of the present disclosure.

The first aspect of the present disclosure provides a compound having a structure according to Chemical Formula 1:

Chemical Formula 1

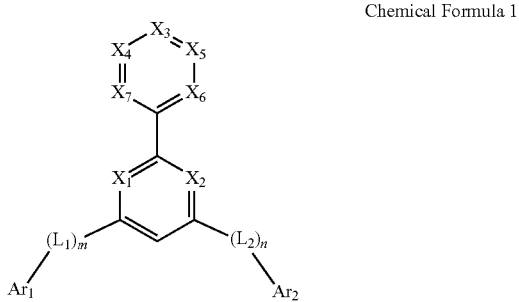

in which,
- $X_1$ and $X_2$ are each independently a carbon atom or a nitrogen atom, and at least one of $X_1$ and $X_2$ is N;
- $X_3$ to $X_7$ are each independently a nitrogen atom or —$CR_a$, wherein one, two, three or four of $X_3$ to $X_7$ are a nitrogen atom, $R_a$ is selected from a group consisting of hydrogen, deuterium, a substituted or unsubstituted C1-C20 alkyl, a substituted or unsubstituted C1-C20 alkoxy, a substituted or unsubstituted C1-C20 thioalkyl, a substituted or unsubstituted C6-C30 aryl, and a substituted or unsubstituted C3-C30 heteroaryl; and $R_a$ is present independently or forms, with adjacent carbon atoms, an aliphatic ring, an aromatic ring, or a heteroaromatic ring;
- $Ar_1$ and $Ar_2$ are each independently selected from a group consisting of a substituted or unsubstituted C6-C30 aryl and a substituted or unsubstituted C3-C30 heteroaryl; and
- $L_1$ and $L_2$ are each independently selected from a group consisting of a single bond, a substituted or unsubstituted C6-C30 arylene, and a substituted or unsubstituted C3-C30 heteroarylene; m is a number of $L_1$, n is a number of $L_2$, and m and n are each an integer independently selected from 1, 2, and 3.

When the nitrogen-heterocyclic compound of the present disclosure is used as a material of a capping layer (CPL) of an organic light-emitting device, it allows a higher refractive index, which can improve the external quantum efficiency (EQE) of the organic light-emitting device. In addition, in an embodiment, the compound of the present disclosure has a relatively small extinction coefficient in a blue light region (400 nm to 450 nm), and has almost no absorption of blue light, which is conducive to improving the luminous efficiency.

In addition, due to aggregation of nitrogen atoms in the nitrogen-heterocyclic compound of the present disclosure, the polarizability of the compound is increased compared to conventional compounds. A difference between refractive indexes for visible light of different wavelengths is small, and thus the color cast can be reduced.

In the compound of the present disclosure, one nitrogen heterocyclic ring is directly connected to another nitrogen heterocyclic ring, so that the nitrogen atoms are tightly stacked, the molecular polarity is increased compared to conventional compounds, the refractive index of the overall molecules is increased compared to conventional compounds, which is favorable for light extraction. At the same time, the compound of the present disclosure, when used in OLED devices, can regulate a light exiting direction and a light extraction efficiency and improve the external quantum efficiency of the OLED devices.

In addition, the compound of the present disclosure has a stable structure and excellent film forming performance. When the compound is used as a light extraction material in OLEDs, it can improve the transmittance of a semi-transmissive electrode and reduce the plasma effect of metal electrons.

The nitrogen-heterocyclic compound of the present disclosure have a high refractive index, and thus are suitable for use as a material of a CPL (capping layer) of an organic light-emitting device to effectively improve the external quantum efficiency (EQE) of an organic light-emitting device. In addition, the compound of the present disclosure has a small extinction coefficient in a blue light wavelength range (400 nm to 450 nm), and has almost no absorption of blue light, which is conducive to improving light-emitting efficiency. Further, in the nitrogen-heterocyclic compound of the present disclosure, a center ring of the compound molecule (a nitrogen heterocyclic ring where $X_1$ and $X_2$ are located) is directly linked to another nitrogen heterocyclic ring (a cyclic group where $X_3$ to $X_7$ are located, where at least one of $X_3$ to $X_7$ is a nitrogen atom), and the center ring is also linked (or linked through $L_1$ or $L_2$) to $Ar_1$ and $Ar_2$. In this way, an electron stacking density of the center nitrogen heterocyclic ring can be further increased compared to conventional compounds, imparting the compound with a greater molecular polarity, increasing the refractive index and a light extraction efficiency of the molecules.

In an embodiment of the nitrogen-heterocyclic compound of the present disclosure, $Ar_1$ and $Ar_2$ are each independently selected from the group consisting of a substituted or unsubstituted phenyl, a substituted or unsubstituted biphenyl, a substituted or unsubstituted terphenyl, a substituted or unsubstituted tetraphenyl, a substituted or unsubstituted naphthyl, a substituted or unsubstituted anthryl, a substituted or unsubstituted phenanthryl, a substituted or unsubstituted pyrenyl, a substituted or unsubstituted fluorenyl, a substituted or unsubstituted spirobifluorenyl, a substituted or unsubstituted carbazolyl, a substituted or unsubstituted dibenzofuryl, a substituted or unsubstituted dibenzothienyl, a substituted or unsubstituted pyrimidinyl, a substituted or unsubstituted triazinyl, a substituted or unsubstituted indolocarbazolyl, a substituted or unsubstituted indolobenzofuryl, a substituted or unsubstituted indolobenzothienyl, a substituted or unsubstituted benzofurylpyrimidinyl, and a substituted or unsubstituted benzothienylpyrimidinyl.

In an embodiment of the nitrogen-heterocyclic compound of the present disclosure, in the Chemical Formula 1, $X_1$ and $X_2$ are each a nitrogen atom. In this case, the ring containing $X_1$ and $X_2$ is a pyrimidine ring. The two electron-absorbing nitrogen atoms on the pyrimidine ring can reduce a density of the electron cloud on the nitrogen heterocyclic ring, and a density of the electron cloud on 5-position of the pyrimidine ring is the lowest. The molecule can have excellent properties when the nitrogen heterocyclic ring structure is bonded to 5-position of the pyrimidine ring allows. The center nitrogen heterocyclic ring of the molecule has a higher electron packing density, and thus the compound has a higher polarizability, thereby improving the refractive index of the compound. When the compound is used as the material of the capping layer of the organic light-emitting device, the light extraction efficiency of the organic light-emitting device is improved, and the light emitting efficiency of the entire device is improved.

The number and distribution density of nitrogen atoms in the nitrogen heterocyclic ring of the molecule may affect the molecular polarizability. An increase in the number of nitrogen atoms may increase the aggregation density, reduce the difference and the correlation between the refractive indexes of the compound for visible light of different wavelengths. In this case, the color cast caused by the capping layer can be reduced.

In an embodiment of the nitrogen-heterocyclic compound of the present disclosure, in the Chemical Formula 1, any two, three, four, or five of $X_3$, $X_4$, $X_5$, $X_6$ and $X_7$ are each a nitrogen atom. In compound molecules, with an increase of the number of nitrogen atoms in $X_3$, $X_4$, $X_5$, $X_6$ and $X_7$, the electron packing density around the center ring also increases, and the optical refractive index of the compound is further increased.

In addition, since the upper nitrogen heterocyclic ring is linked to the lower nitrogen heterocyclic ring (in view of Chemical Formula 1), the molecule have a better flatness, and when used as a capping layer material, the molecular arrangement of the compound is more orderly, so that light is easily refracted and emitted.

In an embodiment of the nitrogen-heterocyclic compound according to the present disclosure, in the Chemical Formula 1, $X_3$, $X_4$ and $X_5$ are carbon atoms, and $X_6$ and $X_7$ are nitrogen atoms.

In the above embodiment, the electron stacking on the nitrogen heterocyclic ring containing $X_3$ to $X_7$ and the center nitrogen heterocyclic ring is more concentrated, which can further improve the refractive index of the compound and the light-emitting efficiency of the organic light-emitting device.

In an embodiment of the nitrogen-heterocyclic compound according to the present disclosure, $Ar_1$ is different from $Ar_2$, and $Ar_1$ and $Ar_2$ are each independently a substituted or unsubstituted C6-C30 aryl.

In this embodiment, the refractive index of the compound can be controlled by changing the substituent. In addition, when each of $Ar_1$ and $Ar_2$ is aryl, the compound molecule can be more stable, the raw materials for synthesis of the compound are easily obtained, and the synthesis is less difficult. If each of $Ar_1$ and $Ar_2$ is heteroaryl, it is difficult to synthesize the compound, the compound has poor stability, and the service life of the device using the compound may also be shortened accordingly.

In an embodiment of the nitrogen-heterocyclic compound according to the present disclosure, in the Chemical Formula 1, $Ar_1$ and $Ar_2$ are each independently any one of the following groups:

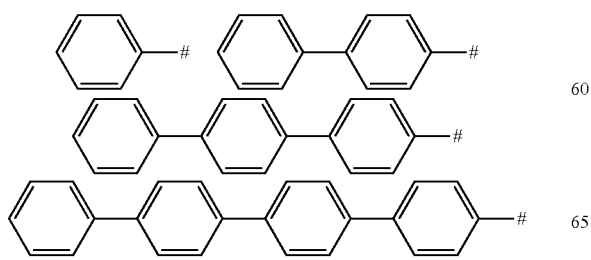

-continued

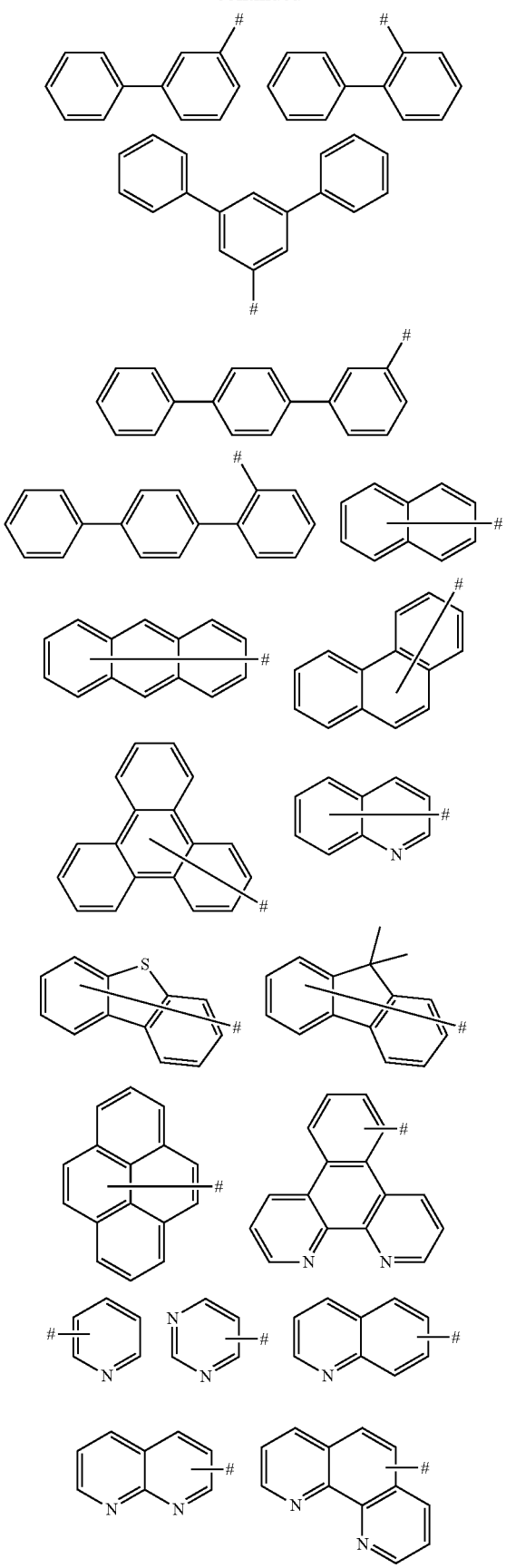

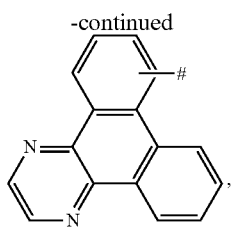

in which # indicates a bonding position.

In an embodiment of the nitrogen-heterocyclic compound according to the present disclosure, in the Chemical Formula 1, $Ar_1$ and $Ar_2$ are each any one of the following groups:

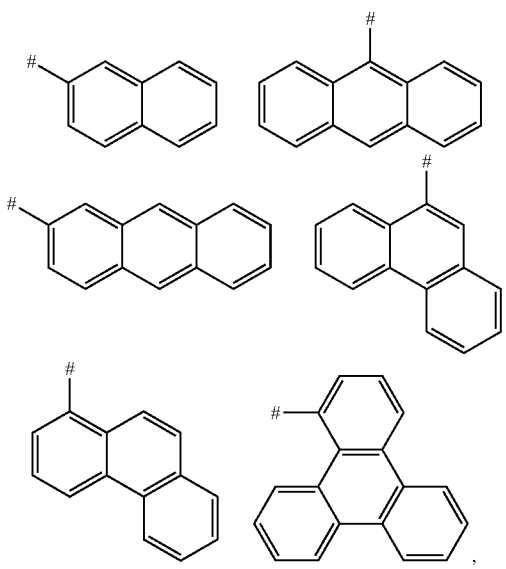

in which # indicates a bonding position.

In an embodiment of the nitrogen-heterocyclic compound according to the present disclosure, in the Chemical Formula 1, $Ar_1$ and $Ar_2$ are each any one of the following groups:

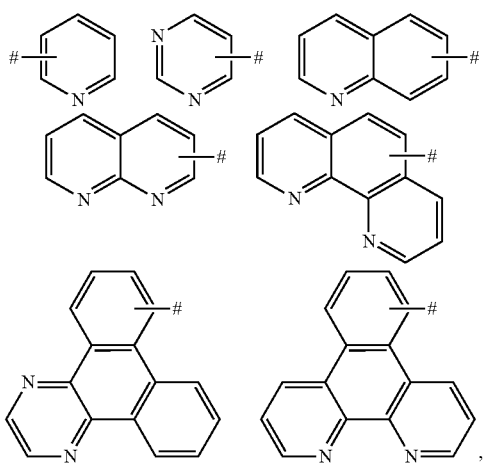

in which # indicates a bonding position.

The heteroaromatic rings such as pyridine, pyrimidine, quinoline, and o-phenanthroline have the function of increasing the polarizability of the compound containing these heteroaromatic rings, and these groups have moderate molecular weights, which is conducive to improving the crystallinity of the compound molecule and the stability of the film formed by the compound.

In an embodiment of the nitrogen-heterocyclic compound according to the present disclosure, in the Chemical Formula 1, m=n=1. In the case where m=n=1, the center nitrogen heterocyclic ring is separated from $Ar_1$ or $Ar_2$ by $L_1$ or $L_2$. In the compound of this embodiment, the molecular conjugation increases, the molecular chain is longer, and the overall molecular orientation tends to be chain-like. The overall compound molecules tend to be orientated more regularly and more orderly after being deposited, which is conducive to light extraction.

In an embodiment of the nitrogen-heterocyclic compound of the present disclosure, in the Chemical Formula 1, $L_1$ and $L_2$ are identical.

In an embodiment of the nitrogen-heterocyclic compound according to the present disclosure, $L_1$ and $L_2$ are each independently the substituted or unsubstituted C3-C30 heteroarylene, and the substituted or unsubstituted C3-C30 heteroarylene contains at least two nitrogen atoms. In the case where m and n are not equal to 0, and $L_1$ and $L_2$ are each independently a heteroarylene group containing at least two nitrogen atoms, the density of electrons around the center nitrogen heterocyclic ring can be further increased, the molecules of the compound used in the capping layer have an increased interaction with surface electrons of the cathode metal atoms, which reduces the coupling between the electromagnetic waves and the free metal electrons and also reduces the resonance between the incident light wave and the electrons, thereby increasing the light extraction efficiency.

In an embodiment of the nitrogen-heterocyclic compound according to the present disclosure, the nitrogen-heterocyclic compound is any one of the following compounds:

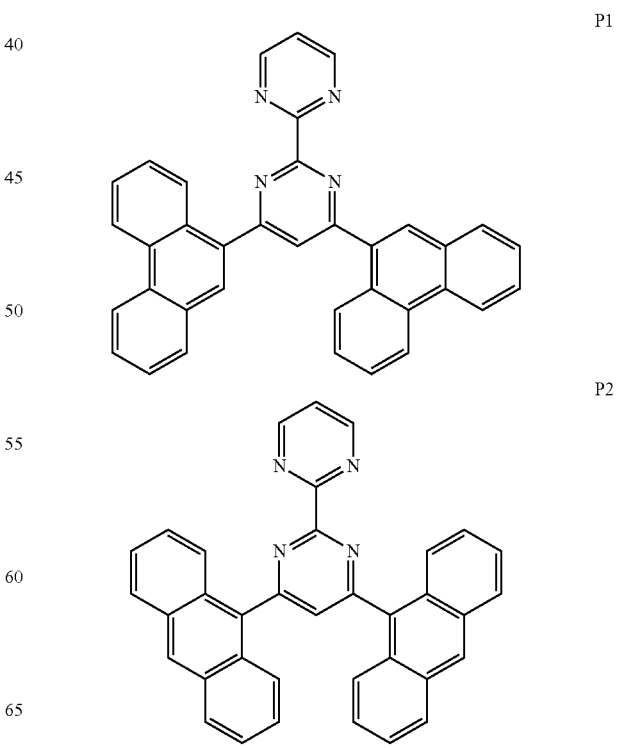

-continued
P3
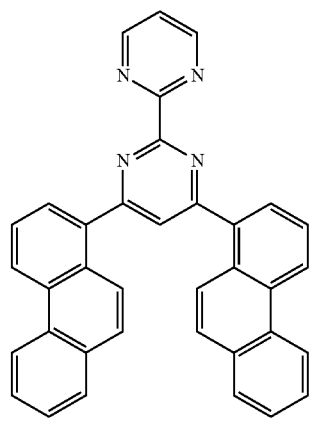
P4
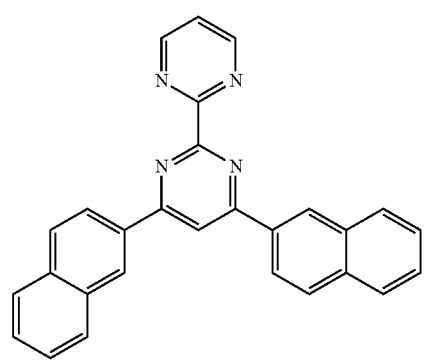
P5
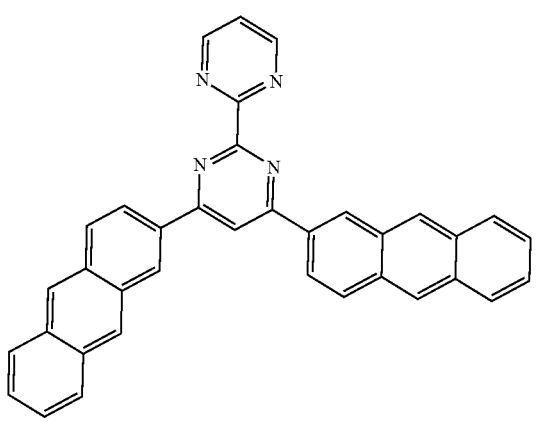
P6
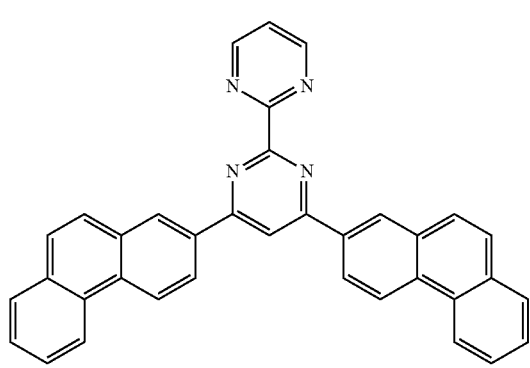
-continued
P7
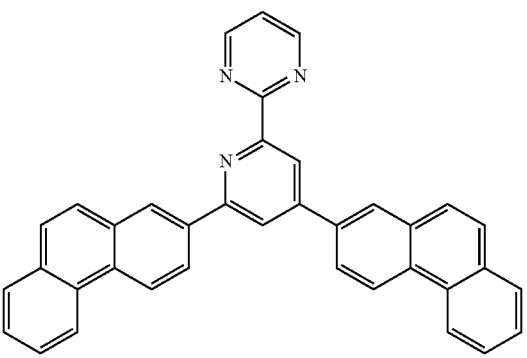
P8
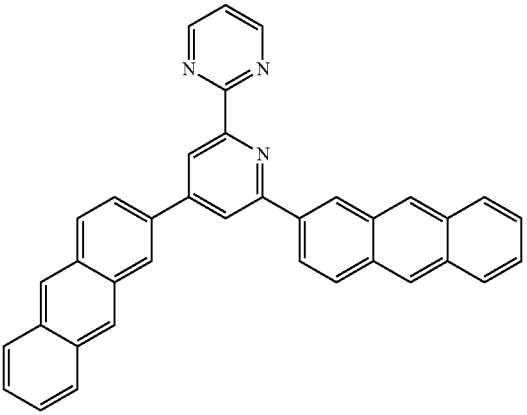
P9
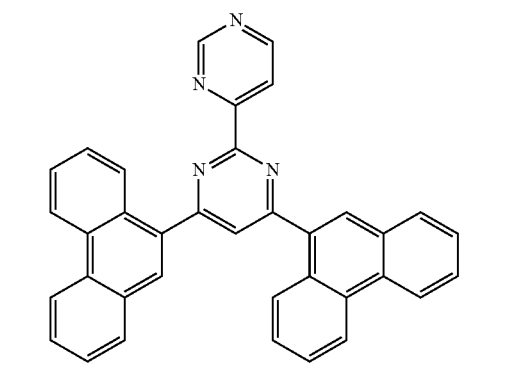
P10
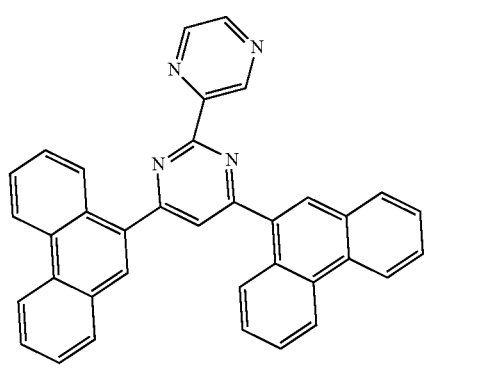

-continued
P11
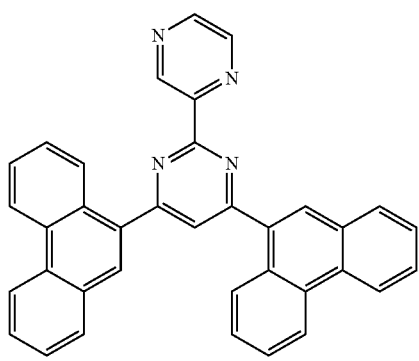
P12
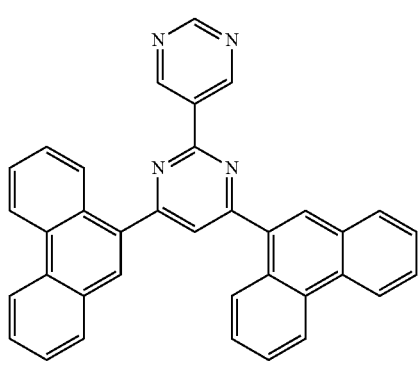
P13
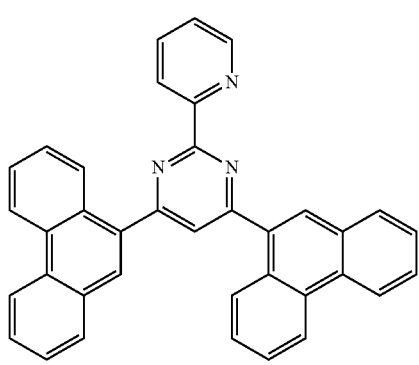
P14
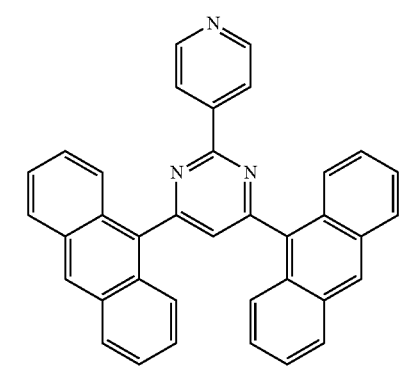
-continued
P15
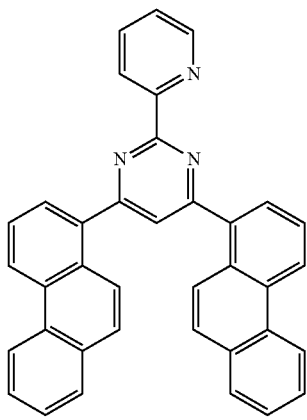
P16
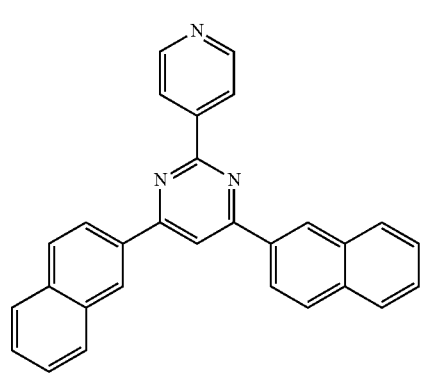
P17
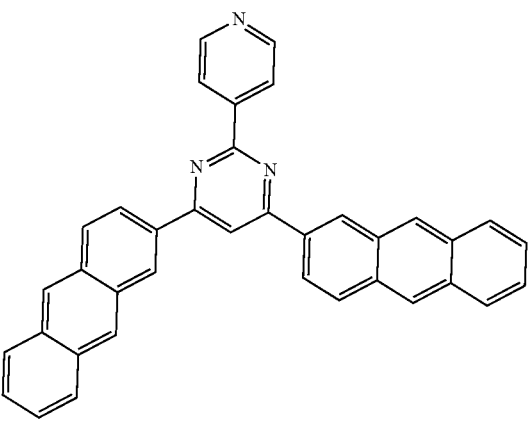
P18
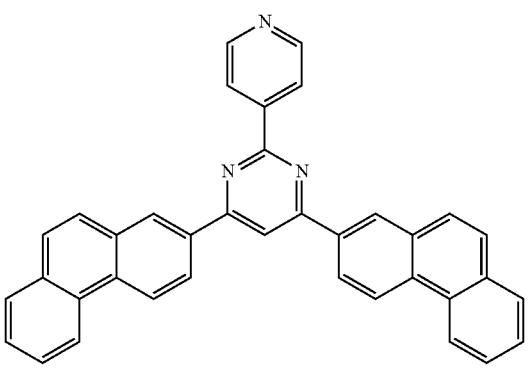

P19
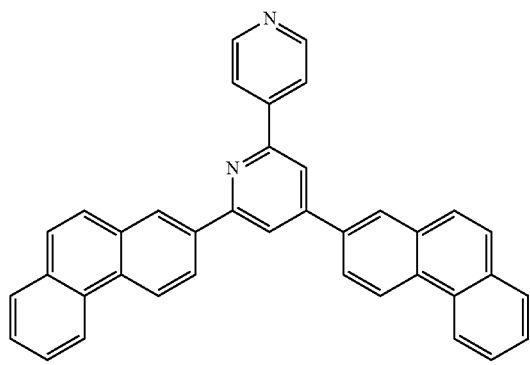
P20
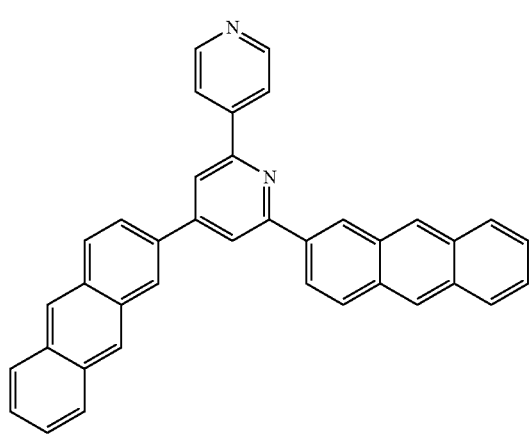
P21
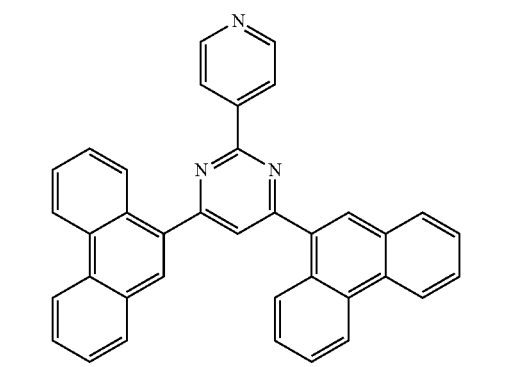
P22
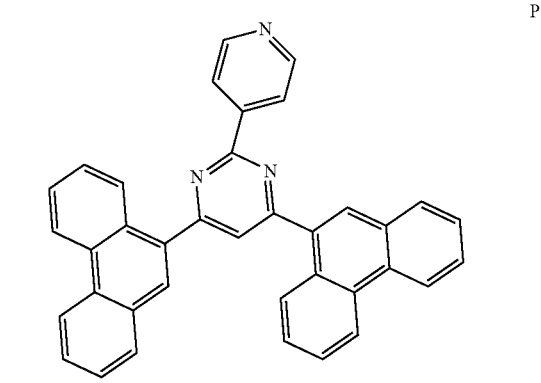
P23
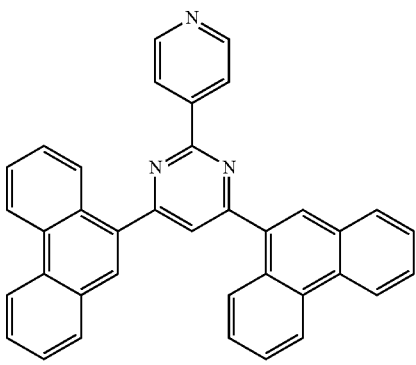
P24
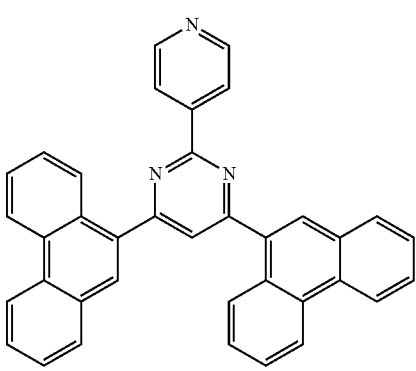
P25
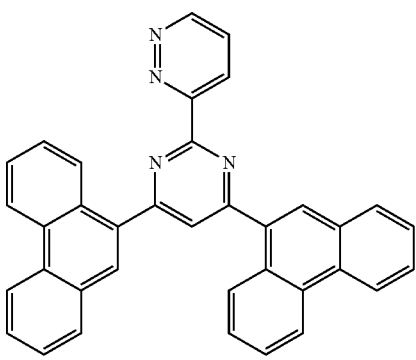
P26
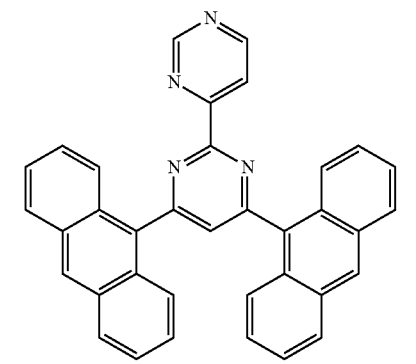

P27
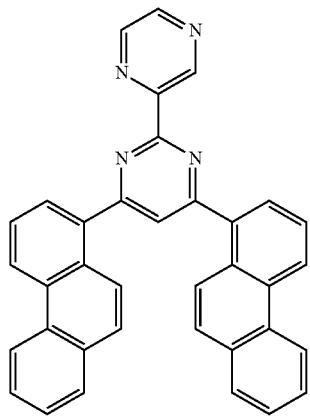
P28
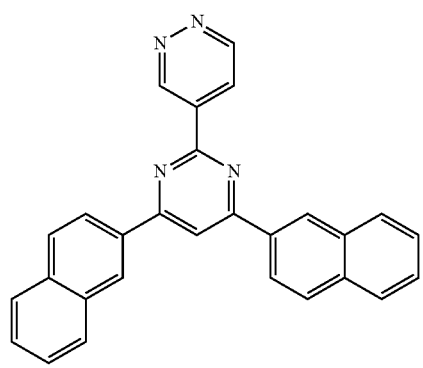
P29
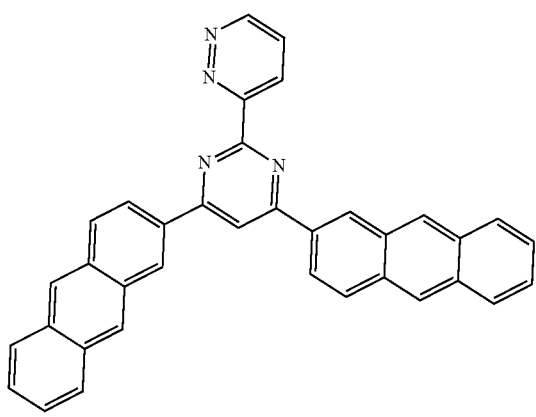
P30
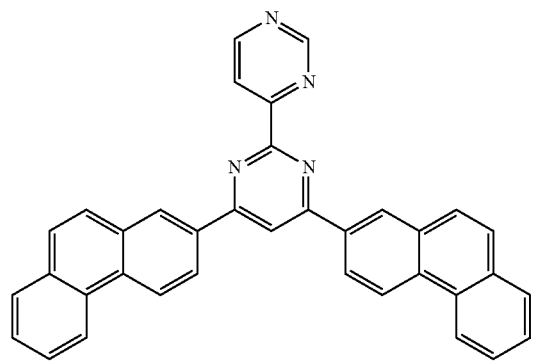
P31
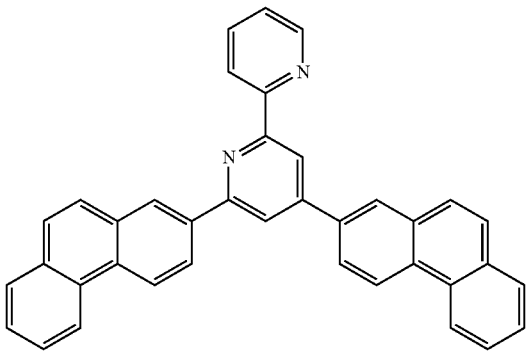
P32
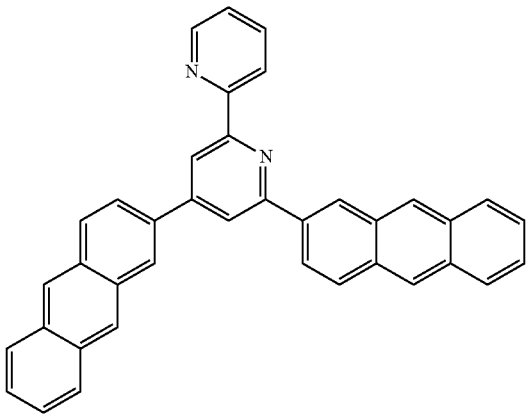
P33
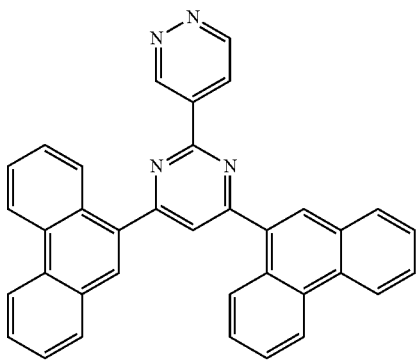
P34
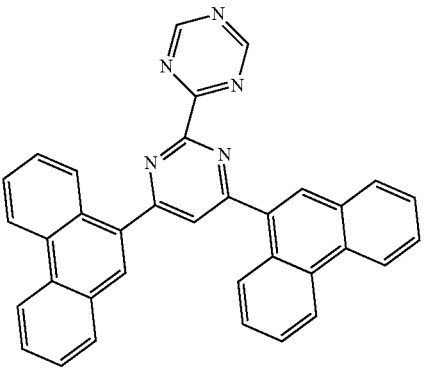

P35
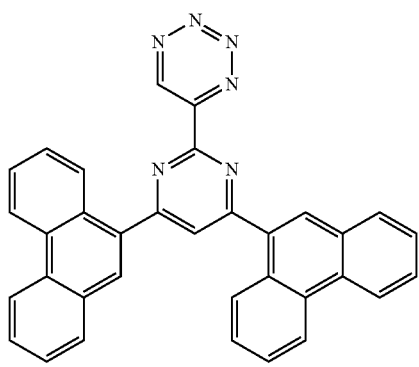
P36
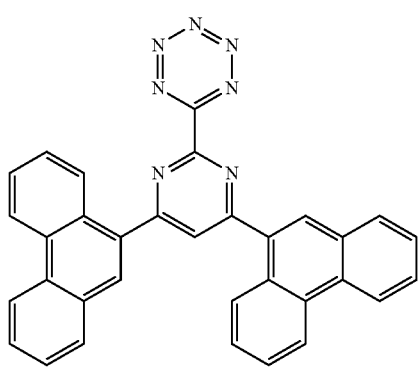
P37
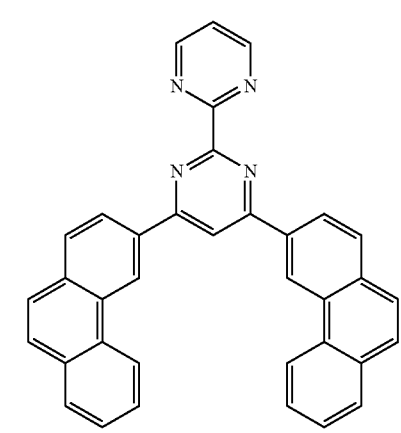
P38
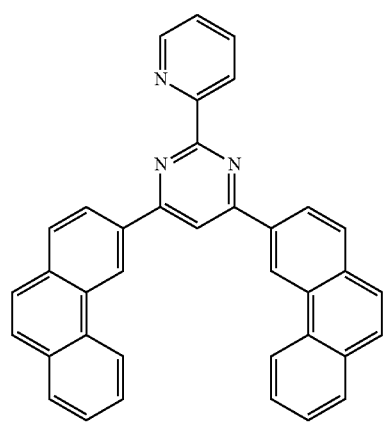
P39
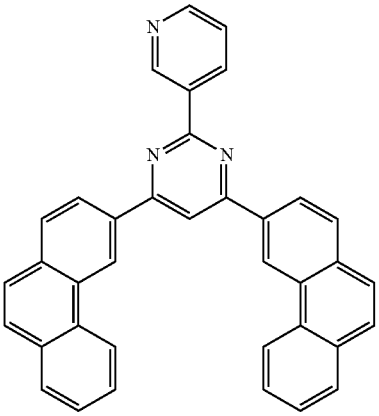
P40
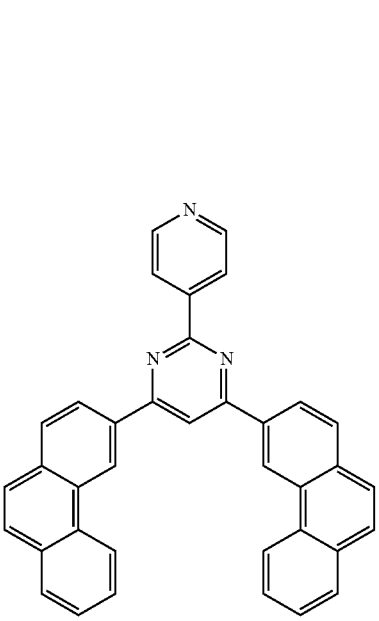
P41
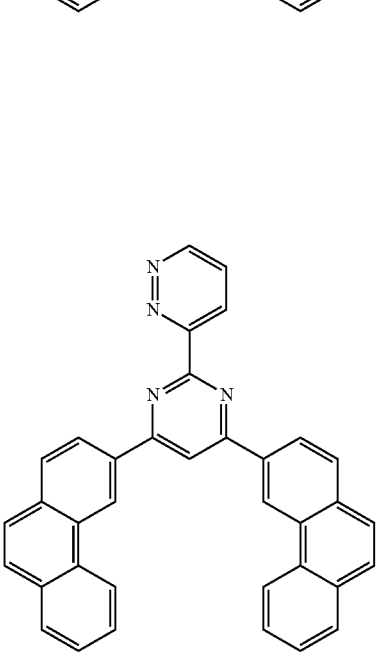

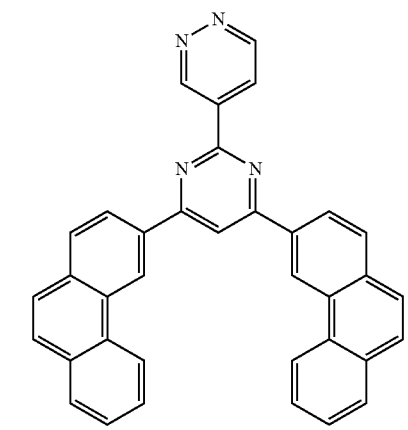
P42
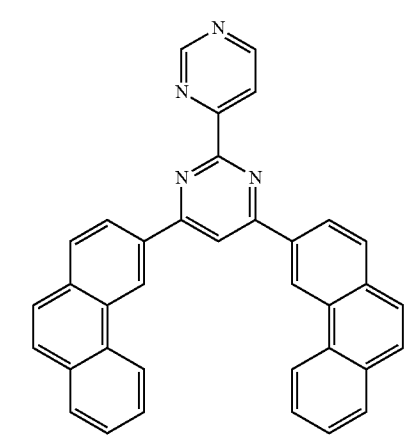
P43
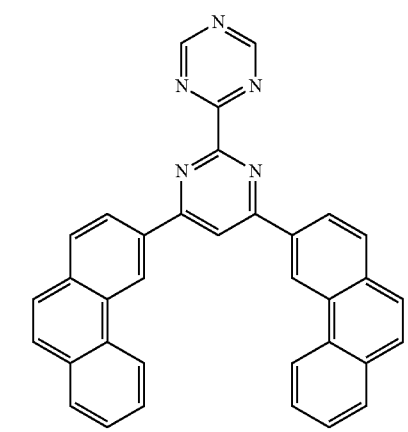
P44
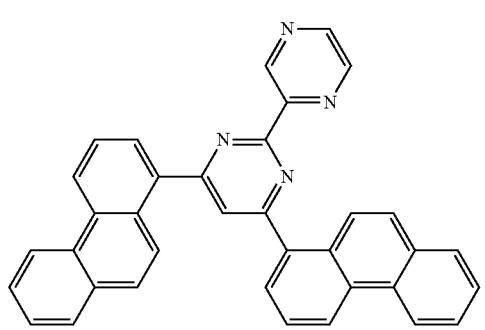
P45
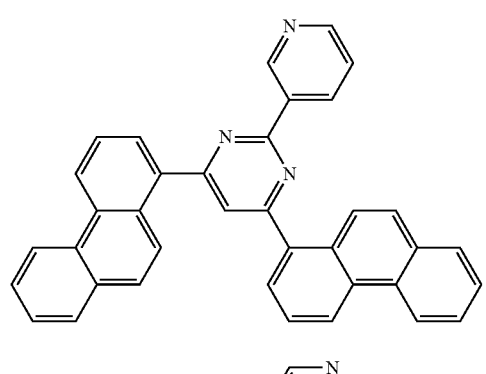
P46
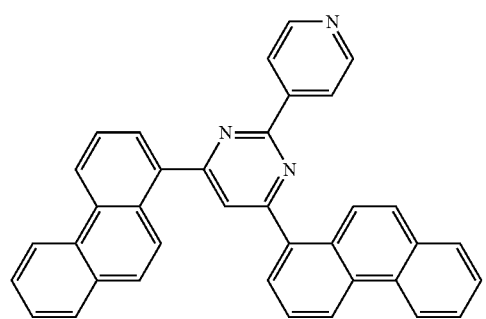
P47
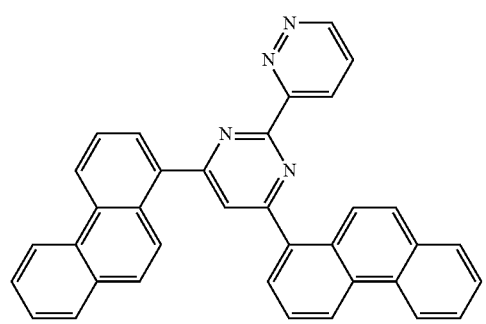
P48
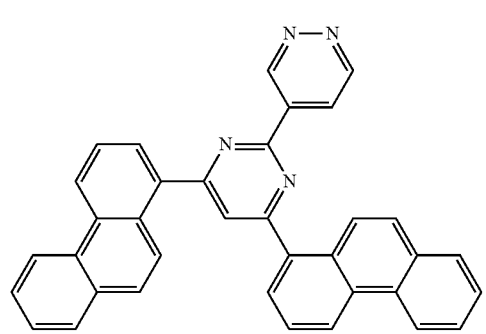
P49
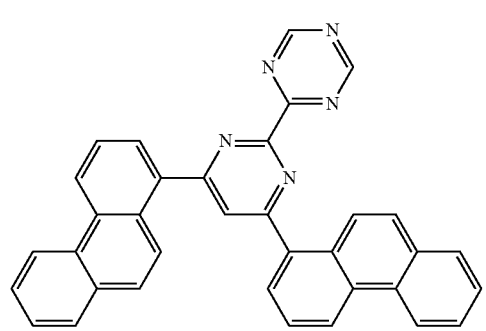
P50

-continued
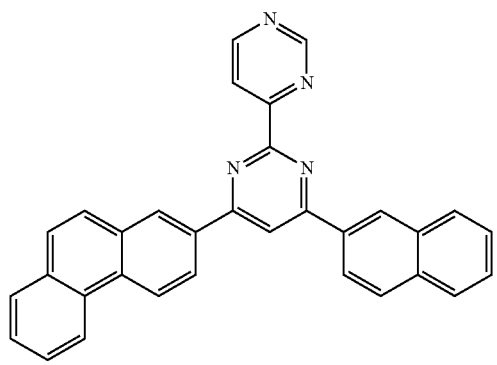
P51
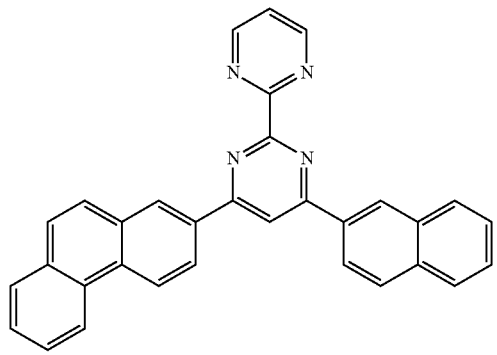
P52
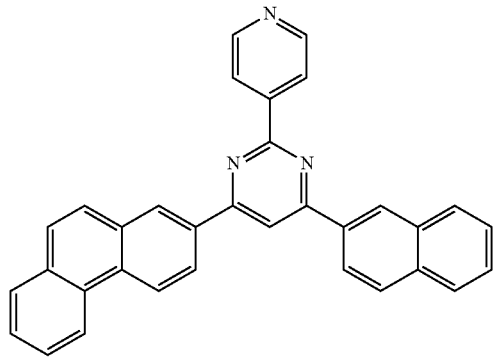
P53
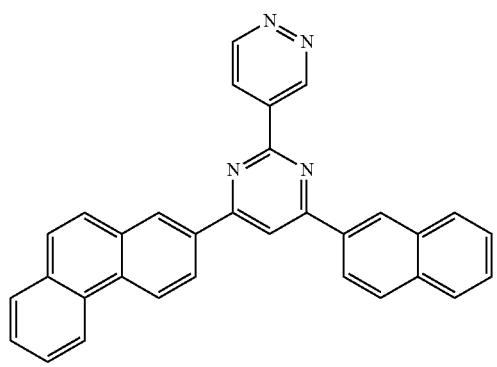
P54
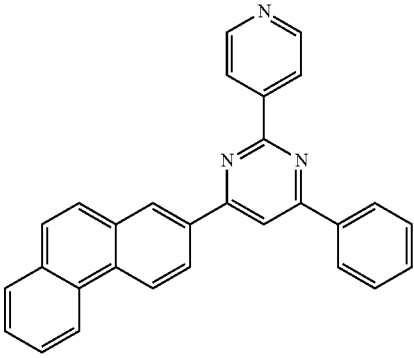
P55
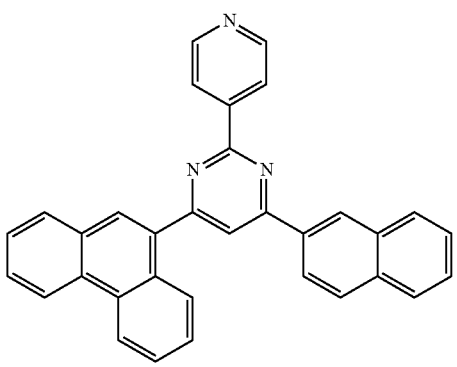
P56
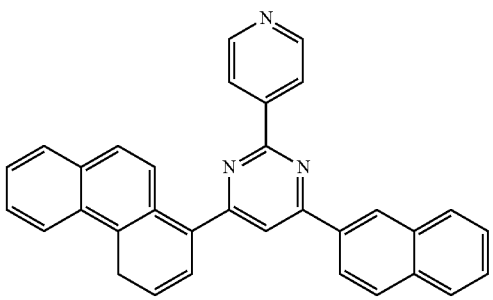
P57
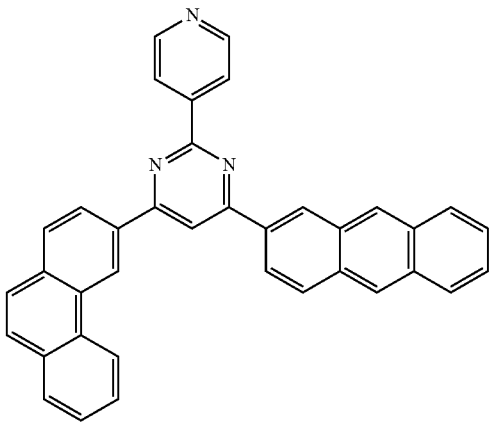
P58

-continued
P59
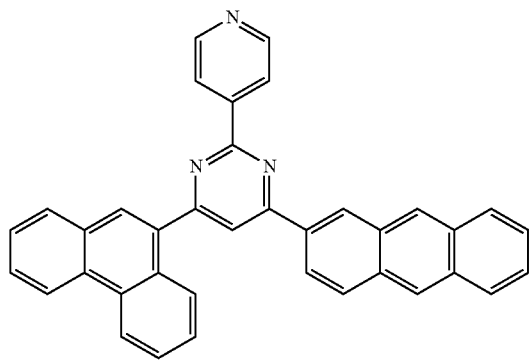
P60
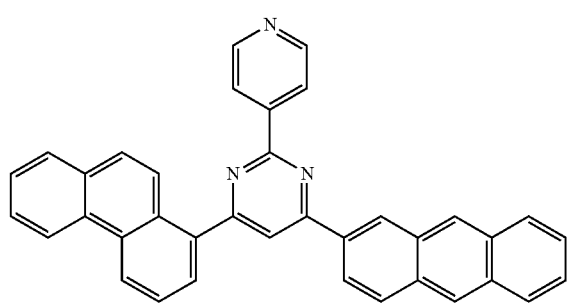
P61
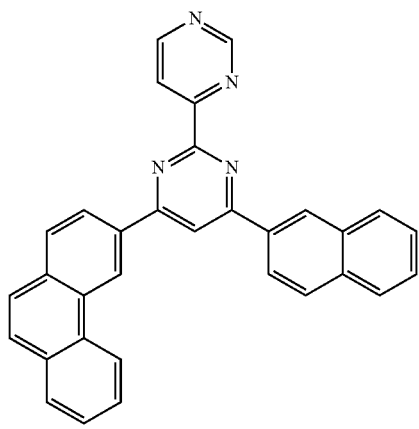
P62
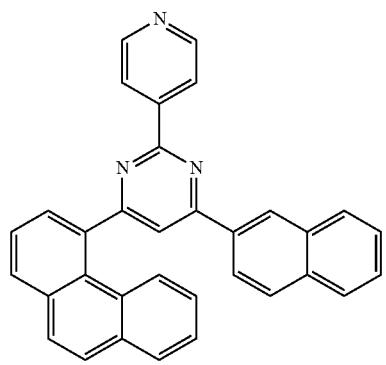
-continued
P63
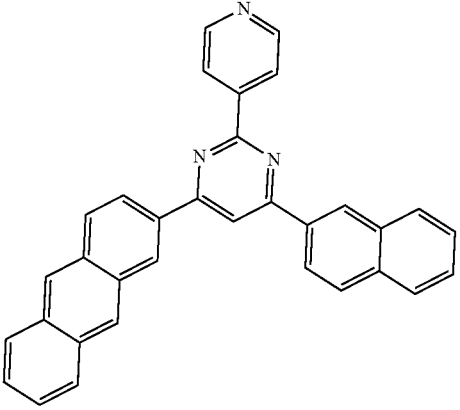
P64
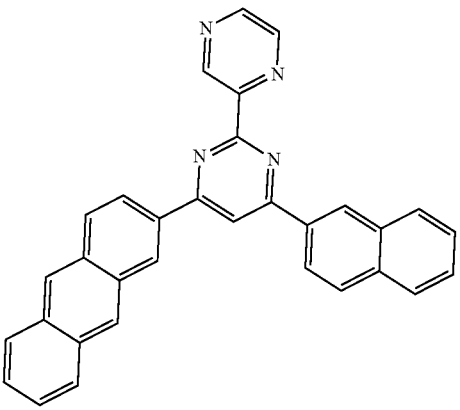
P65
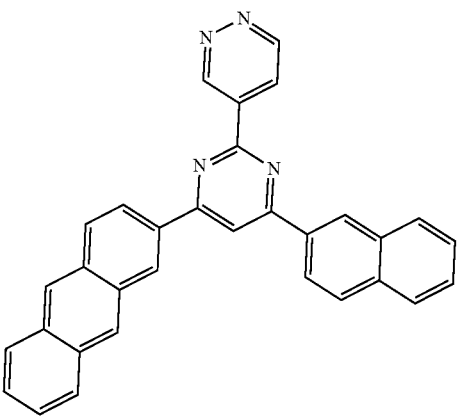
P66
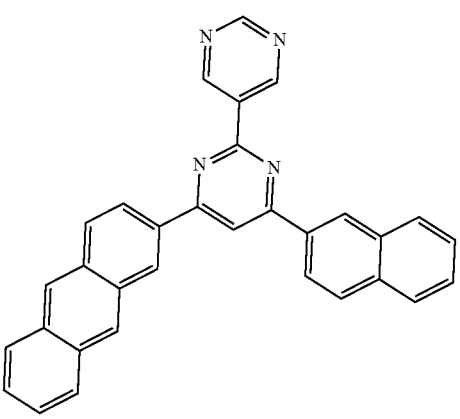

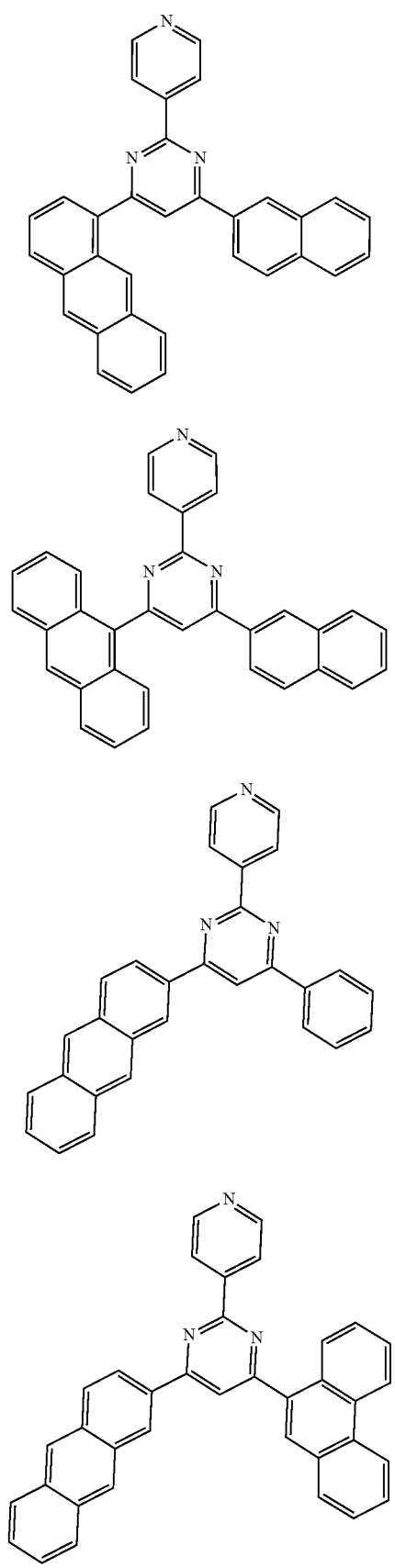
P67
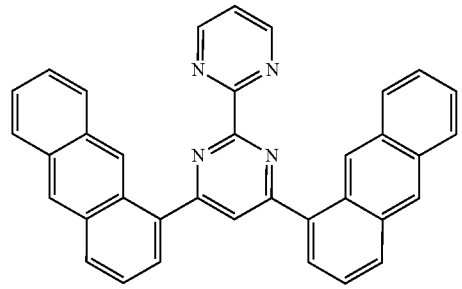
P71
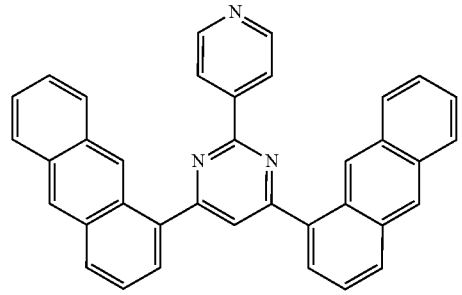
P72
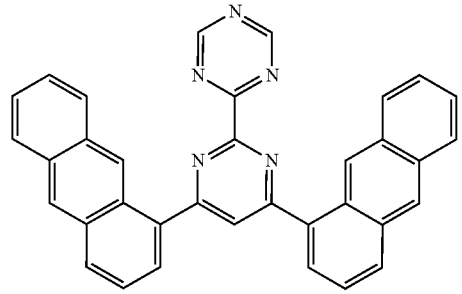
P73
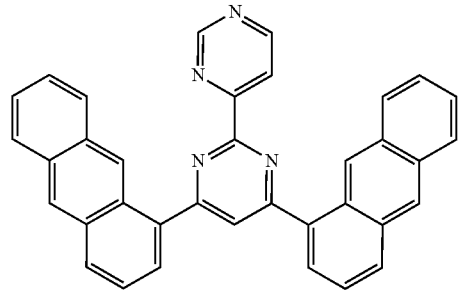
P74
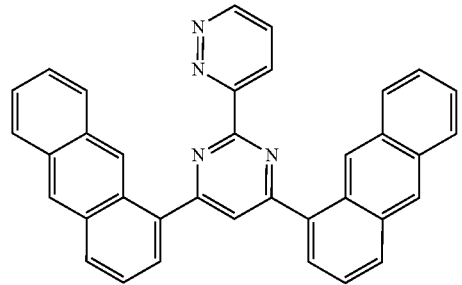
P75

-continued
P76
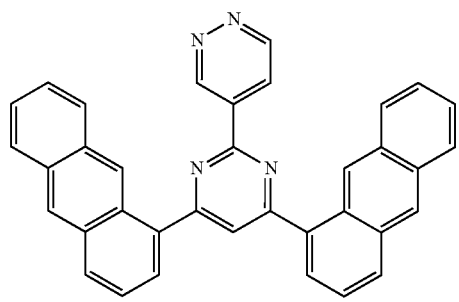
P77
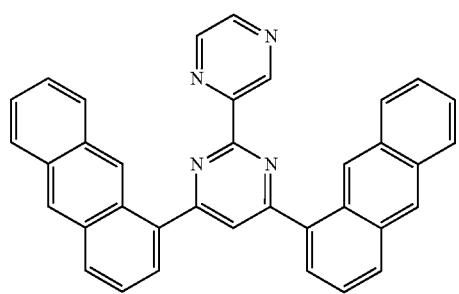
P78
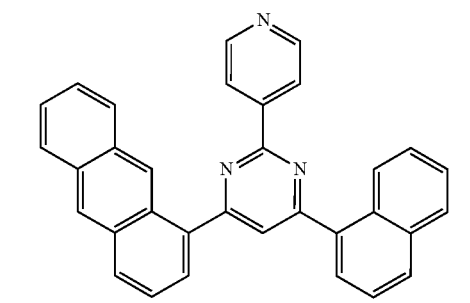
P79
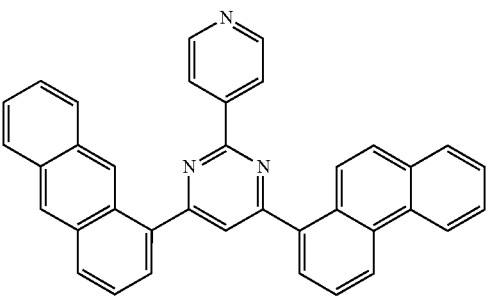
P80
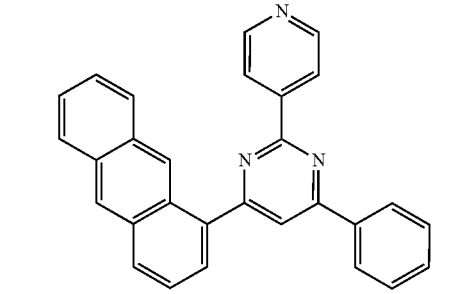
-continued
P81
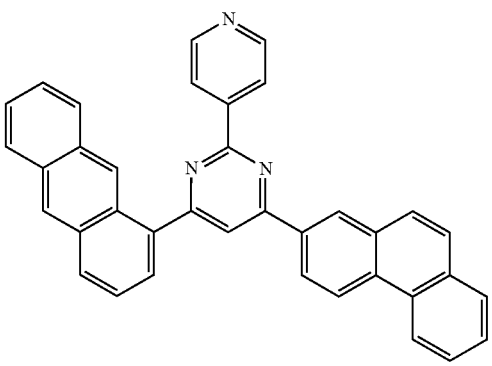
P82
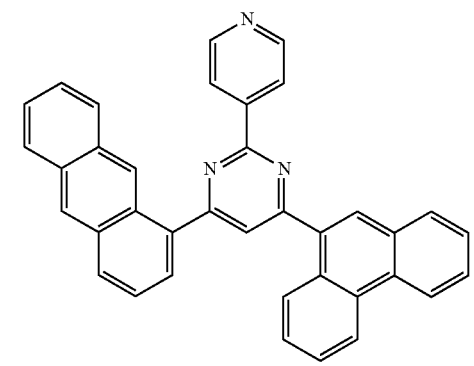
P83
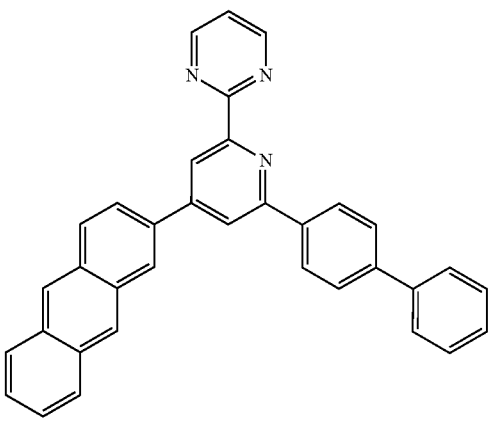
P84
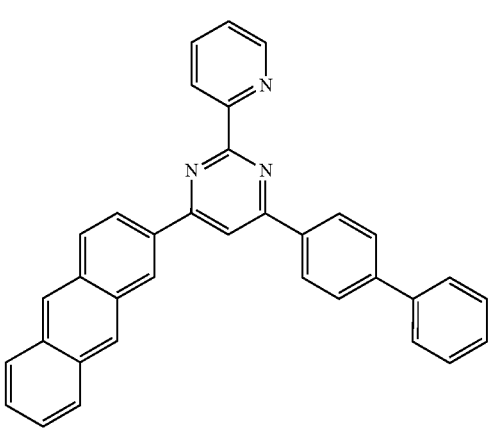

P85 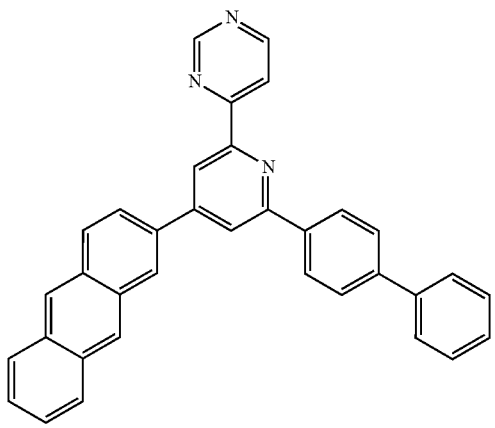
P86 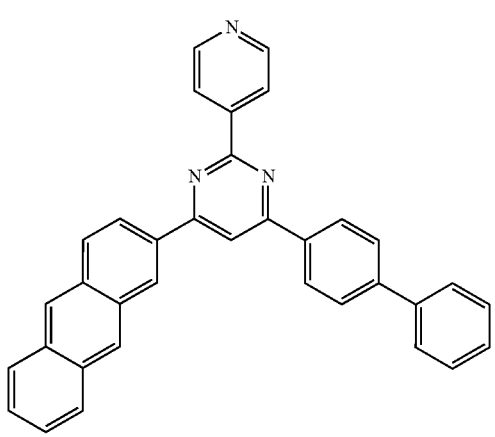
P87 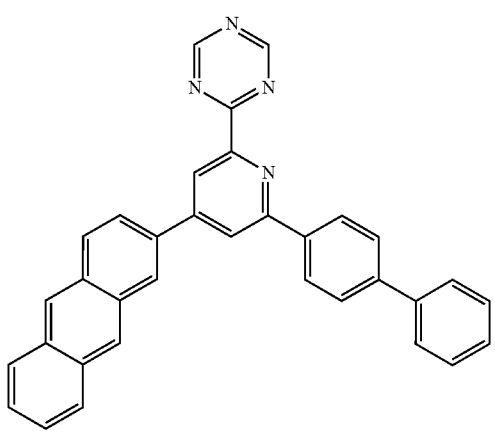
P88 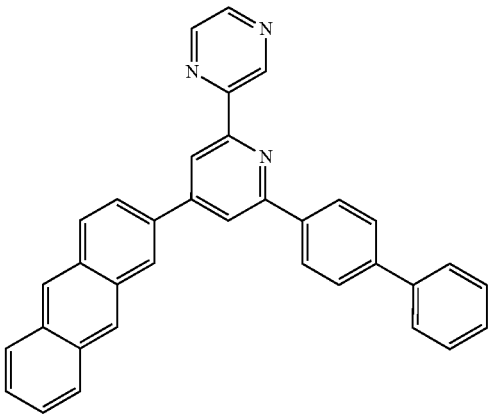
P89 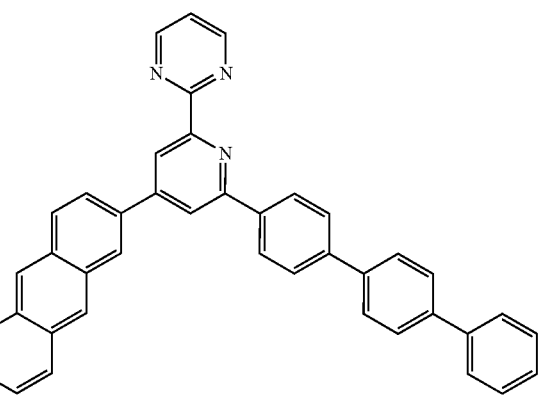
P90 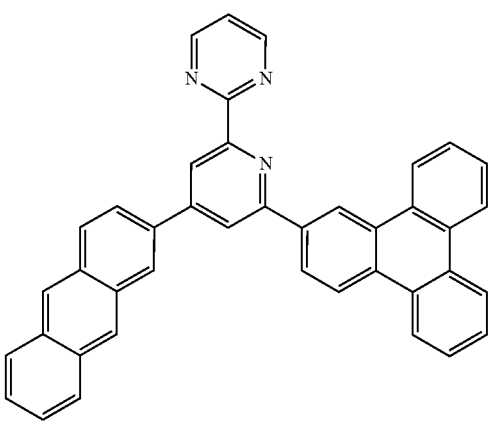

-continued
P91
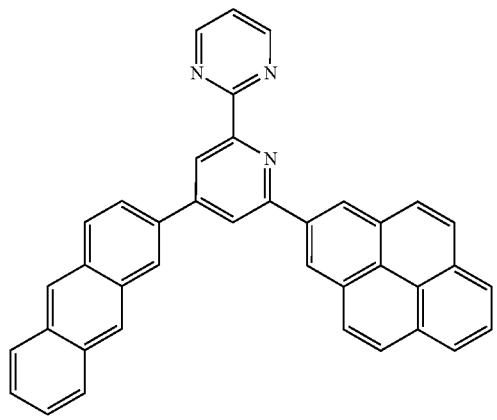
P92
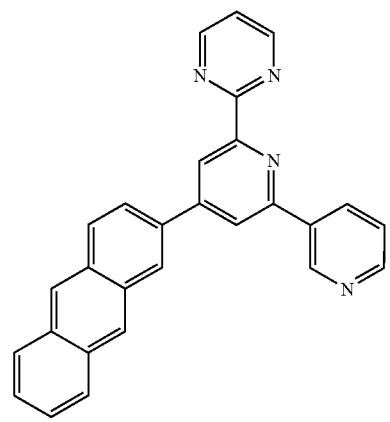
P93
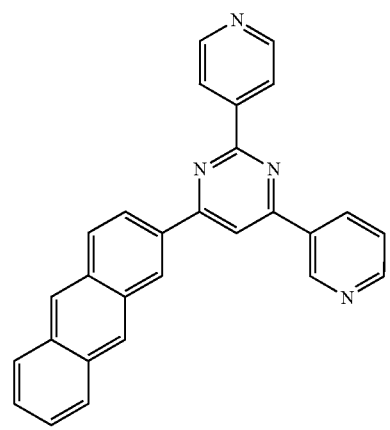
-continued
P94
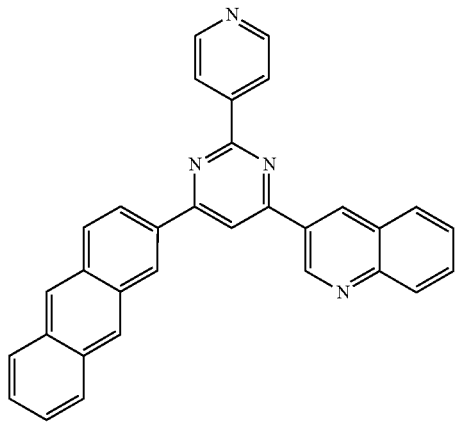
P95
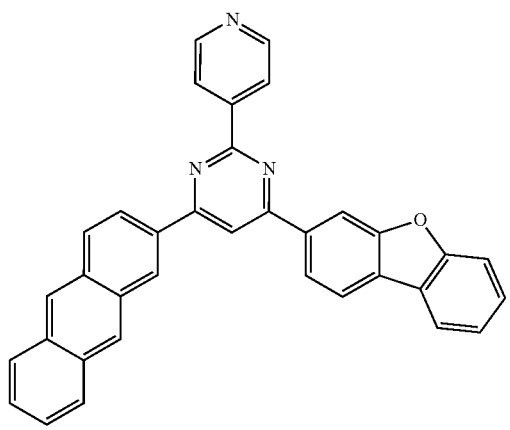
P96
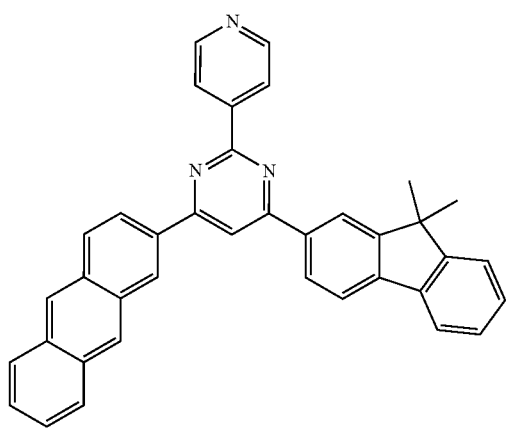

P97
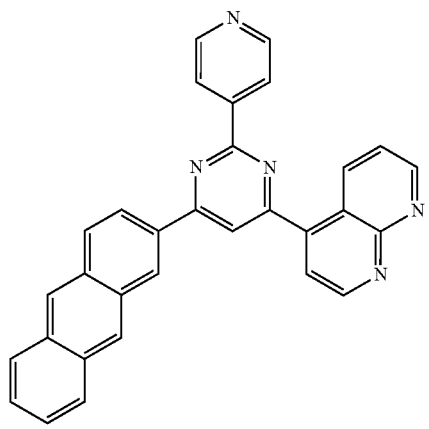
P98
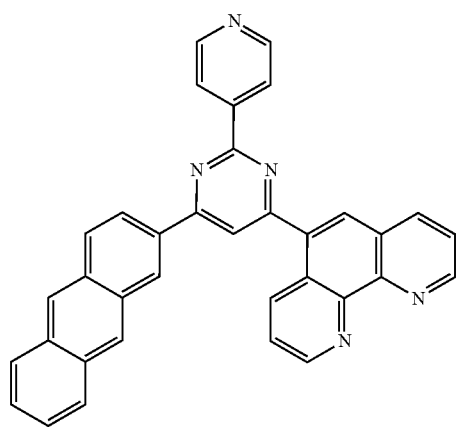
P99
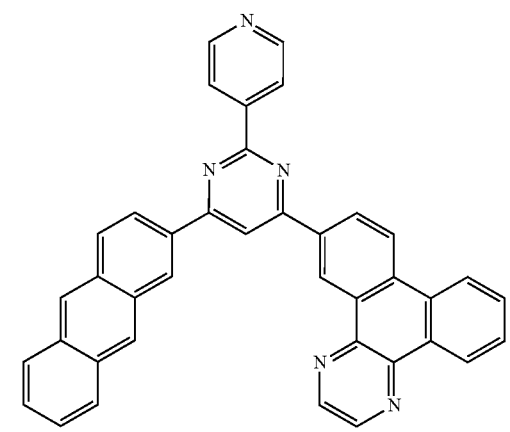
P100
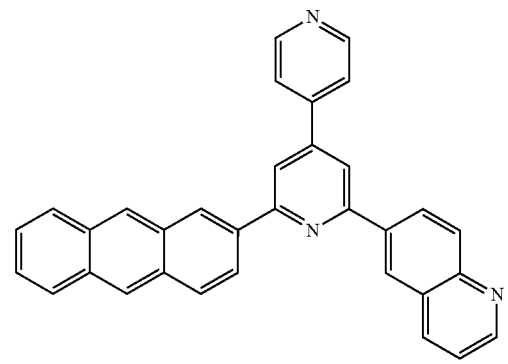
P101
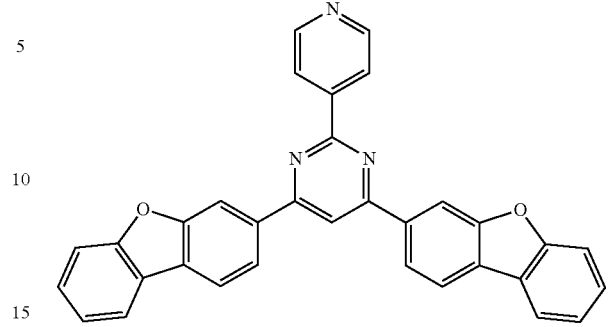
P102
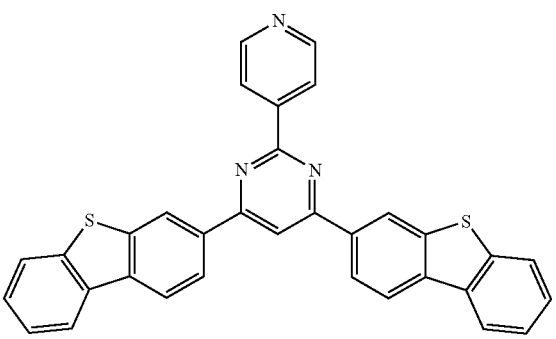
P103
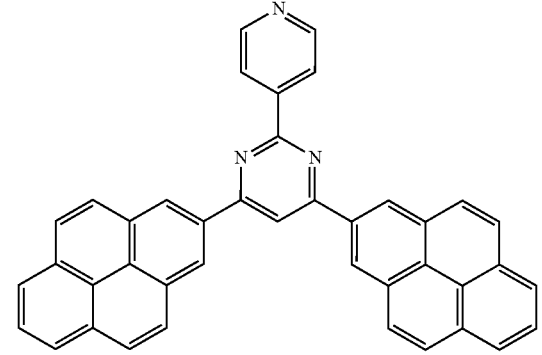
P104

-continued
P105
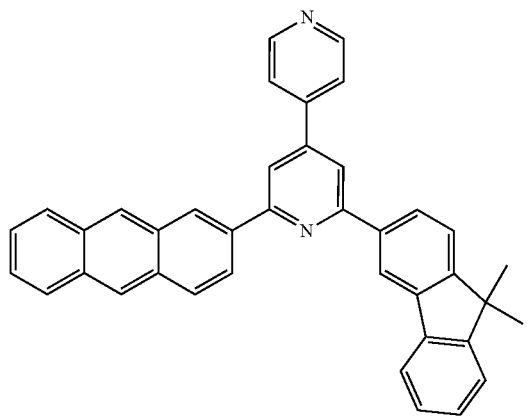
P106
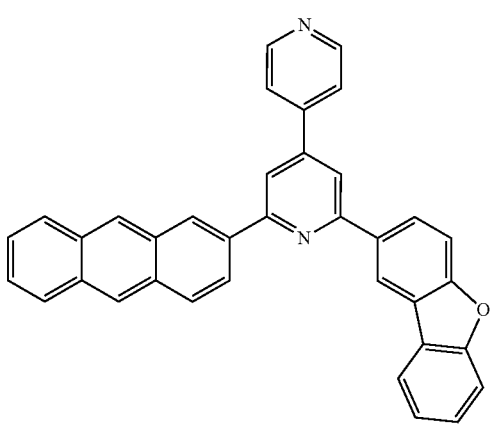
P107
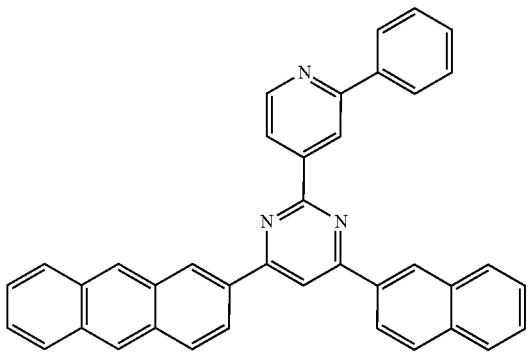
P108
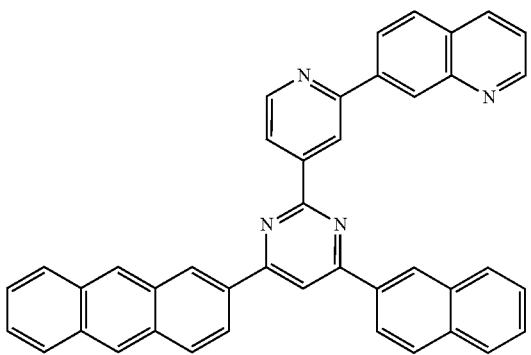
P109
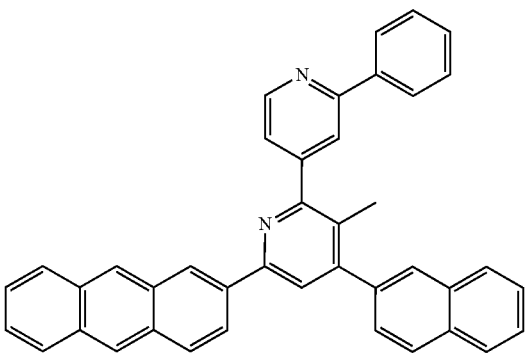
P110
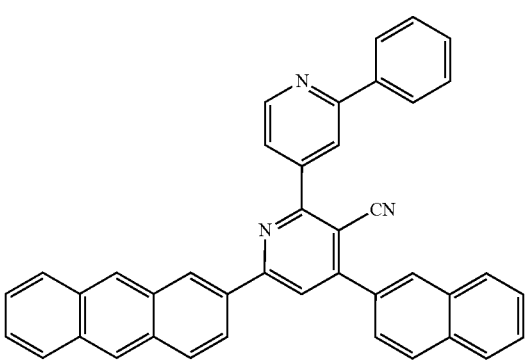
P111
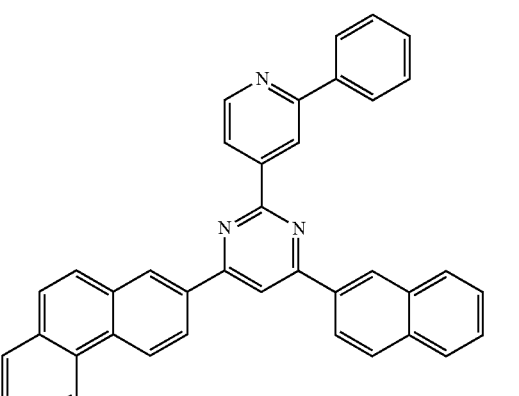
P112
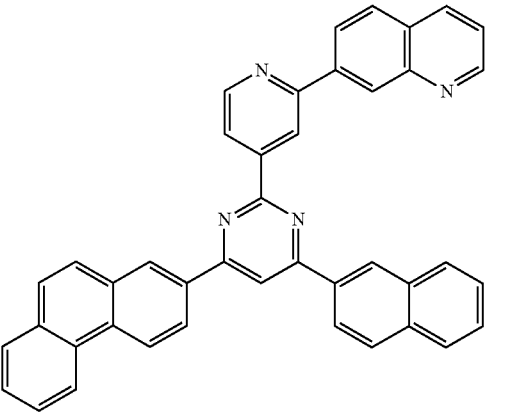

P113
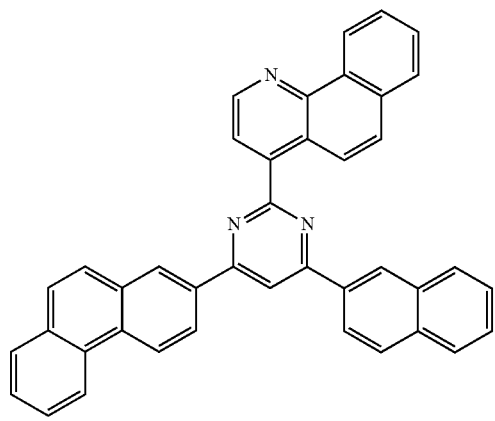
P114
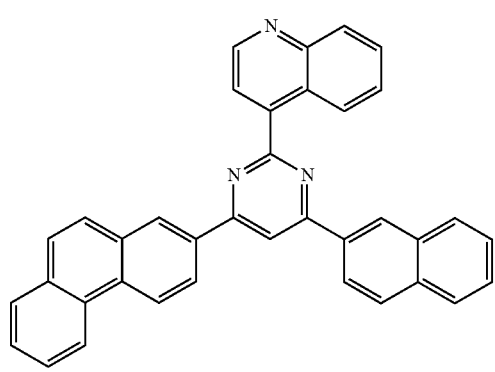
P115
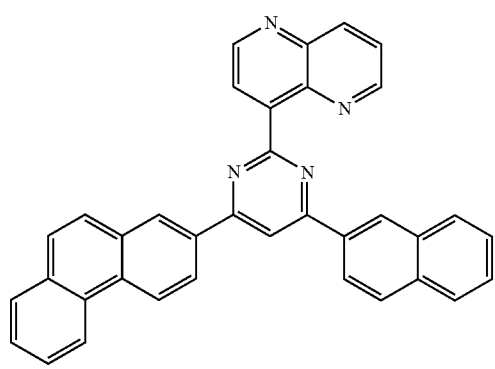
P116
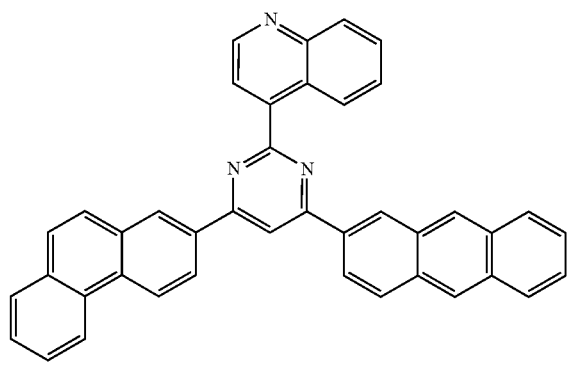
P117
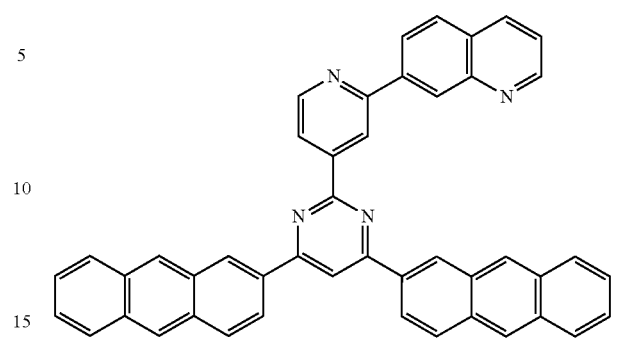
P118
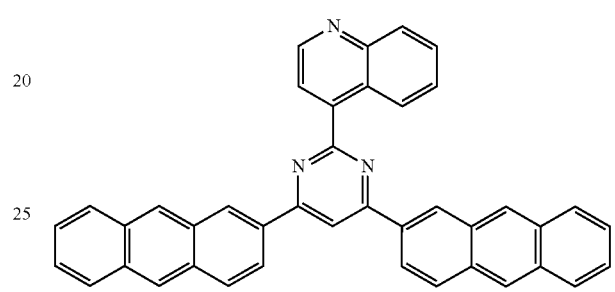
P119
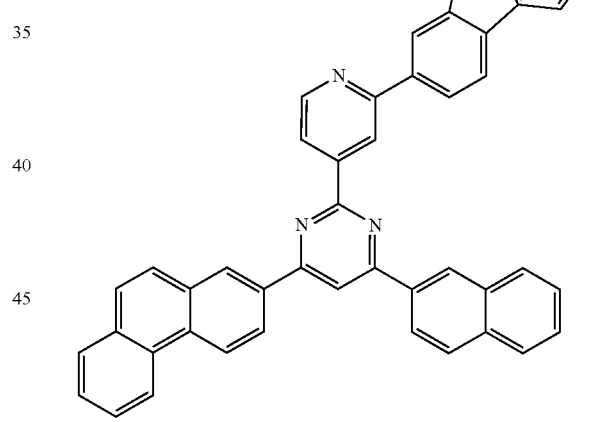
P120
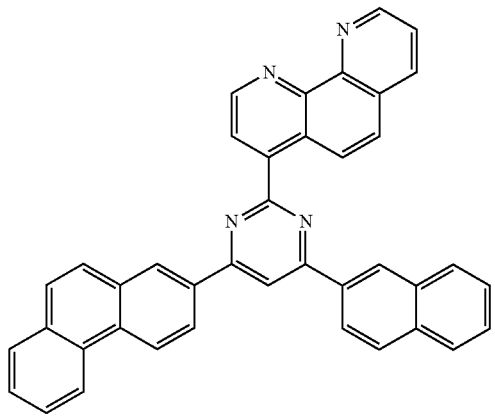

P121
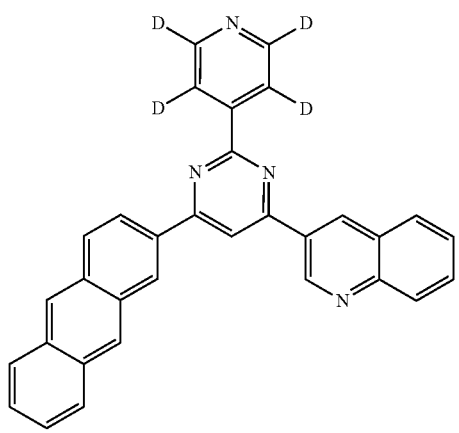
P124
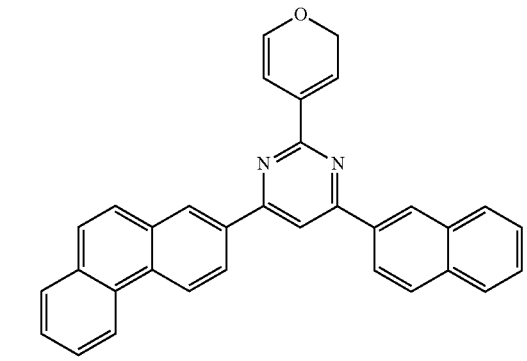
P122
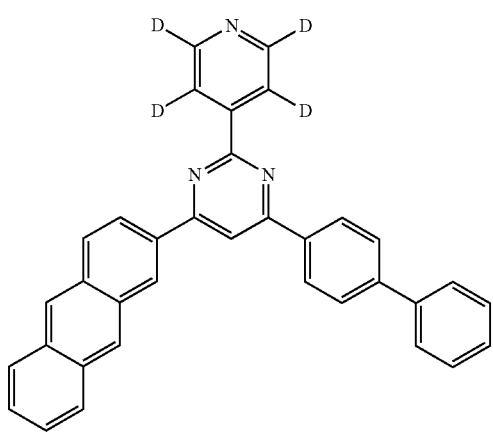
P125
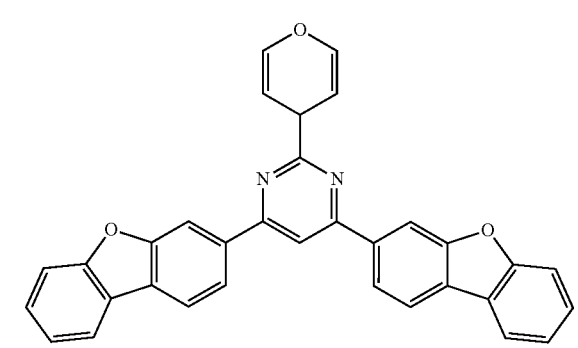
P126
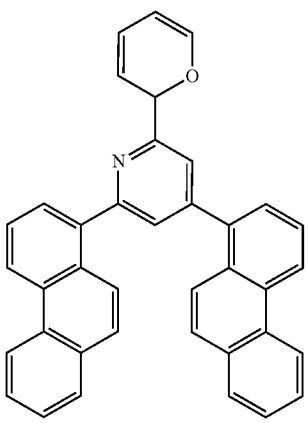
P123
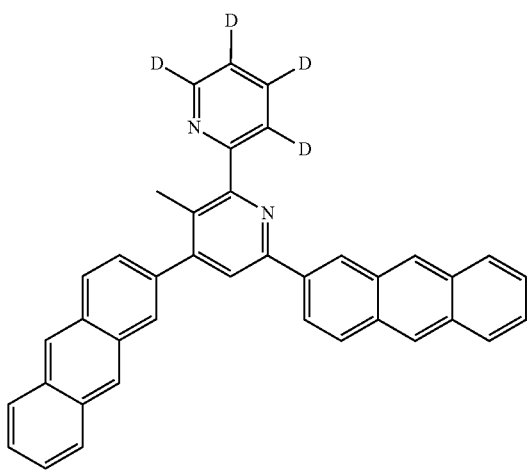
P127
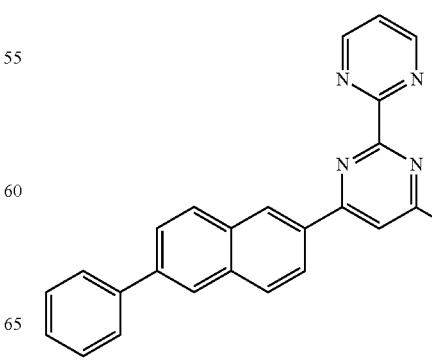

P128 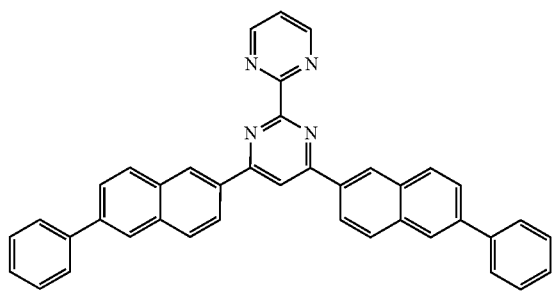

P130 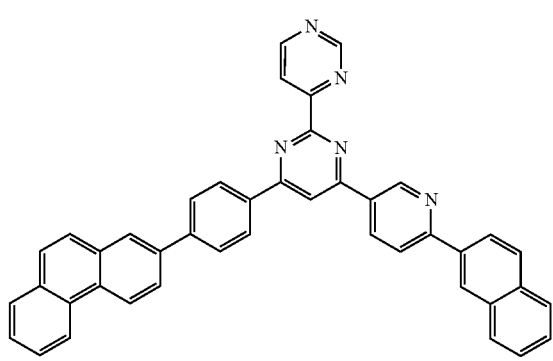

P129 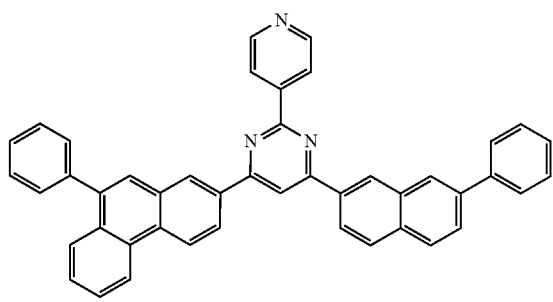

P131 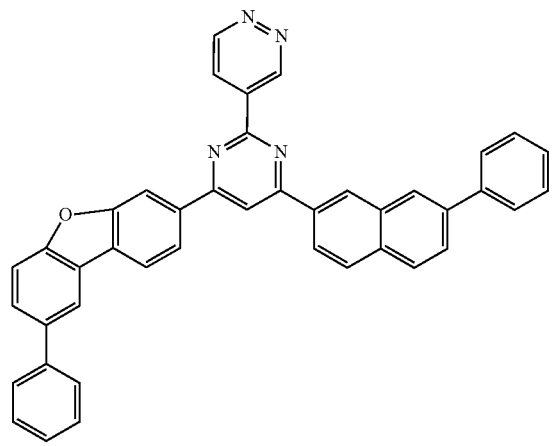

P132 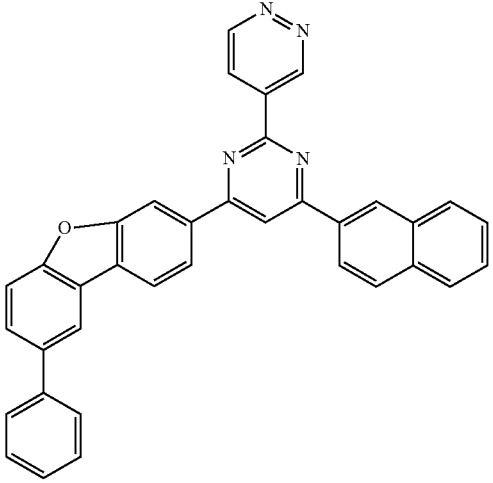

The nitrogen-heterocyclic compounds in the embodiments of the present disclosure have a refractive index greater than or equal to 2.0 for visible light having a wavelength of 400 nm to 700 nm, satisfying the basic performance requirements of OLED devices for the CPL materials. Therefore, the compounds of the present disclosure are suitable for use as CPL materials.

The nitrogen-heterocyclic compounds in the embodiments of the present disclosure have an extinction coefficient less than or equal to 0.1 for visible light having a wavelength of 430 nm to 600 nm. Blue light generally has a wavelength of 400 nm to 450 nm. In an embodiment, the extinction coefficient of the compounds of the present disclosure that is less than or equal to 0.1 for visible light having a wavelength of 430 nm to 600 nm means indicates that the compounds of the present disclosure have little or no absorption of visible light having a wavelength longer than the wavelength of the blue light.

An embodiment of the present disclosure provides a display panel. The display panel includes an organic light-emitting device, and the organic light-emitting device includes: an anode; a cathode arranged opposite to the anode; an organic layer located between the anode and the cathode and including a light-emitting layer; and a capping layer located at a side of a light exiting side electrode facing away from the organic layer. The light exiting side electrode is the anode or the cathode. A material of the capping layer includes the nitrogen-heterocyclic compound according to the present disclosure.

In an embodiment of the display panel of the present disclosure, the cathode with the capping layer has a transmittance greater than 65% for visible light having a wavelength of 400 nm to 700 nm.

In an embodiment of the display panel of the present disclosure, the capping layer satisfies the following conditions:

(1) a refractive index for light having a wavelength of 450 nm to 650 nm is greater than 2.0, and an extinction coefficient for light having a wavelength of 450 nm to 650 nm is 0.0 or less;

(2) a difference between a refractive index for light having a wavelength of 450 nm and a refractive index for light having a wavelength of 550 nm is less than 0.40; and (3) a difference between the refractive index for the light having a wavelength of 550 nm and a refractive index for light having a wavelength of 630 nm is less than 0.20.

In an embodiment of the display panel of the present disclosure, for the cathode together with the capping layer, a difference between a refractive index for light having a wavelength of 450 nm and a refractive index for light having a wavelength of 550 nm is less than 0.15, and a difference between the refractive index for the light having a wavelength of 550 nm and a refractive index for light having a wavelength of 630 nm is less than 0.15. By using the nitrogen-heterocyclic compound of the present disclosure, the organic light-emitting device has a small difference between the refractive indexes for visible light in various wave bands, which can reduce the color cast of the display panel.

The synthesis schemes of several exemplary compounds of the present disclosure are listed below.

Example 1

Synthesis of Compound P1

The synthesis scheme of pound P1 is as below:

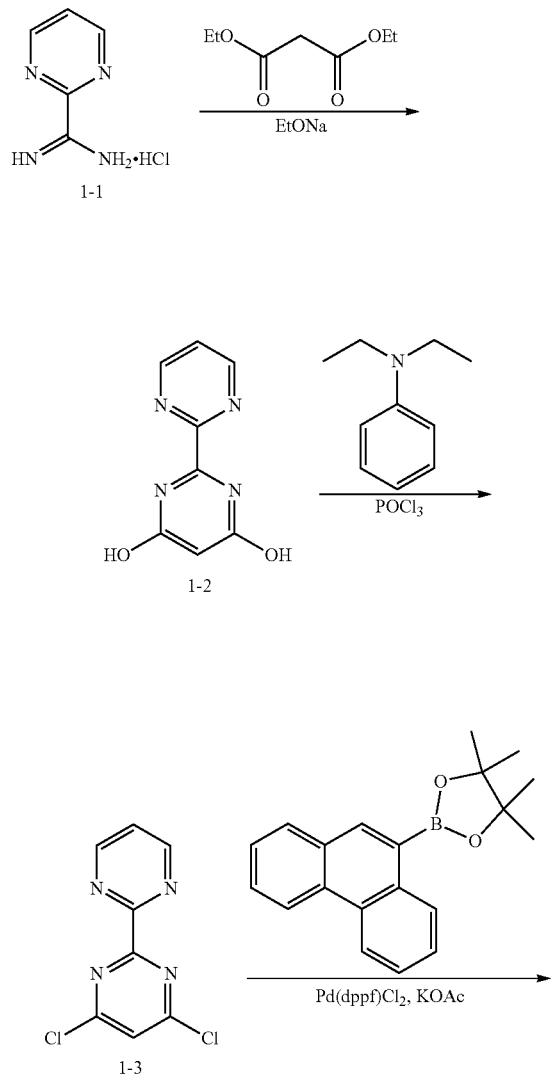

-continued

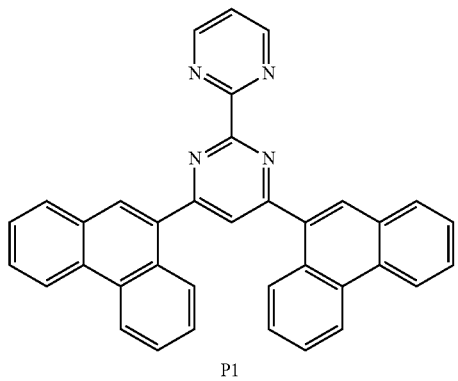

P1

(1) In a 250 ml round bottom flask, a compound 1-1 (15 mmol), diethyl malonate (35 mmol) and sodium ethoxide (15 mmol) were added to dry ethanol (100 ml), and the reaction was performed at 78° C. for 12 hours under nitrogen atmosphere. The obtained intermediate mixture solution was added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate product 1-2.

(2) In a 250 ml round bottom flask, the intermediate product 1-2 (15 mmol) and diethylphenylamine (15 mol) were added to dry $POCl_3$ (100 ml), and the reaction was performed at 120° C. for 6.0 hours under nitrogen atmosphere. The obtained intermediate mixture solution was added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate product 1-3.

(3) In a 250 ml round bottom flask, the intermediate product 1-3 (15 mmol), potassium acetate (40 mmol), 9-phenanthreneboronic acid pinacol ester (15 mmol), dry 1,4-dioxane (60 ml), and $Pd(dppf)Cl_2$ (0.4 mmol) were mixed and reacted at 90° C. under nitrogen atmosphere while being stirred. The obtained intermediate was cooled to room temperature and then added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the product P1.

Characterization Results of Compound P1:

$^1$H NMR (400 MHz, $CDCl_3$): δ 8.93-8.80 (m, 16H), 8.84 (d, J=8.4 Hz, 2H), 7.93 (s, 2H), 7.64 (s, 1H), 7.32 (t, J=3.2 Hz, 1H).

Elemental analysis results (molecular formula: $C_{36}H_{22}N_4$): theoretical: a carbon atom, 84.71; H, 4.31; a nitrogen atom, 10.98; measured: a carbon atom, 83.71; H, 4.51; a nitrogen atom, 11.78. ESI-MS (m/z)(M+) obtained through Liquid Chromatography/Mass Spectrometry: theoretical, 510.18; measured, 510.10.

Example 2

Synthesis of Compound P17

The synthesis scheme of compound P17 is shown as below:

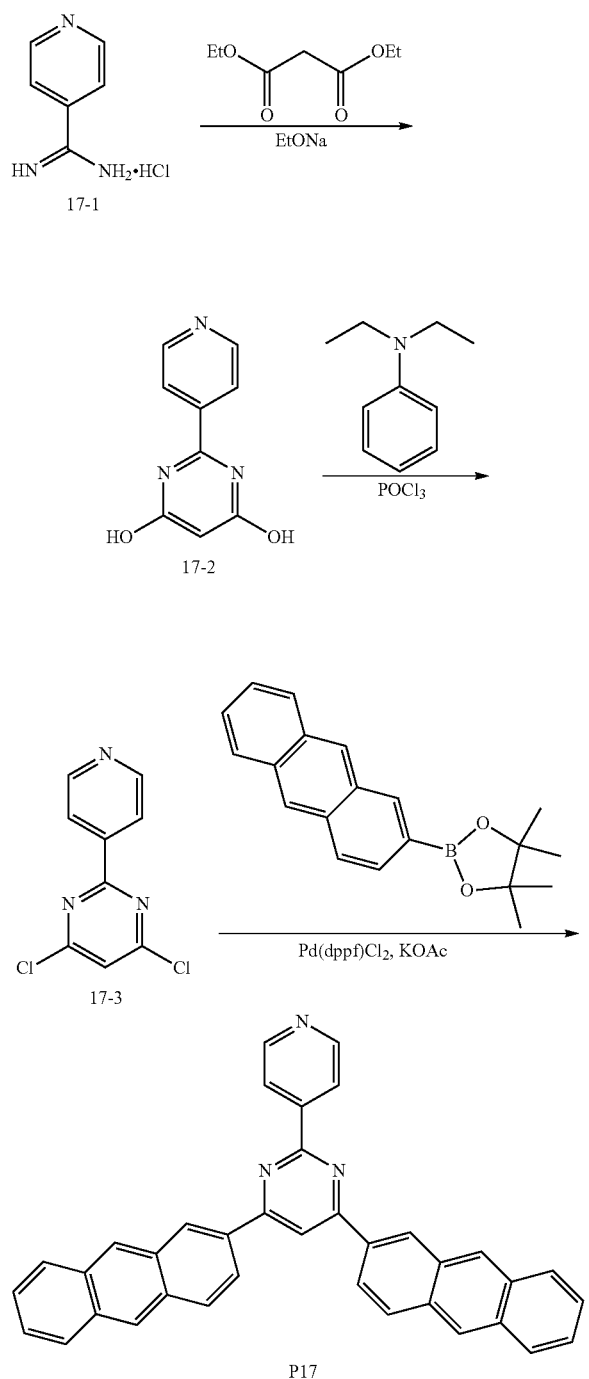

P17

(1) In a 250 ml round bottom flask, a compound 17-1 (15 mmol), diethyl malonate (35 mmol) and sodium ethoxide (15 mmol) were added to dry ethanol (100 ml), and the reaction was performed at 78° C. for 12 hours under nitrogen atmosphere. The obtained intermediate mixture solution was added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate product 17-2.

(2) In a 250 ml round bottom flask, the intermediate product 17-2 (15 mmol) and diethylphenylamine (15 mol) were added to dry POCl₃ (100 ml), and the reaction was performed at 120° C. for 6.0 hours under nitrogen atmosphere. The obtained intermediate mixture solution was added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate product 17-3.

(3) In a 250 ml round bottom flask, the intermediate product 17-3 (15 mmol), potassium acetate (40 mmol), 2-anthraceneboronic acid pinacol ester (15 mmol), dry 1,4-dioxane (60 ml), and Pd(dppf)Cl₂ (0.4 mmol) were mixed and reacted for 48 hours at 90° C. under nitrogen atmosphere while being stirred. The obtained intermediate was cooled to room temperature, then added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the product P17.

Characterization Results of Compound P17:

$^1$H NMR (400 MHz, CDCl₃): δ 8.65 (d, J=8.4 Hz, 2H), 8.31 (s, 4H), 8.13 (s, 2H), 7.97-7.39 (m, 12H), 7.60 (d, J=8.4 Hz, 2H), 7.64 (s, 1H);

Elemental analysis results (molecular formula: $C_{37}H_{23}N_3$): theoretical: a carbon atom, 87.23; H, 4.52; a nitrogen atom, 8.25; measured: a carbon atom, 88.20; H, 4.72; a nitrogen atom, 7.35. ESI-MS (m/z)(M+) obtained through Liquid Chromatography/Mass Spectrometry: theoretical, 509.19; measured, 509.08.

Example 3

Synthesis of Compound P18

The synthesis scheme of compound P18 is shown as below:

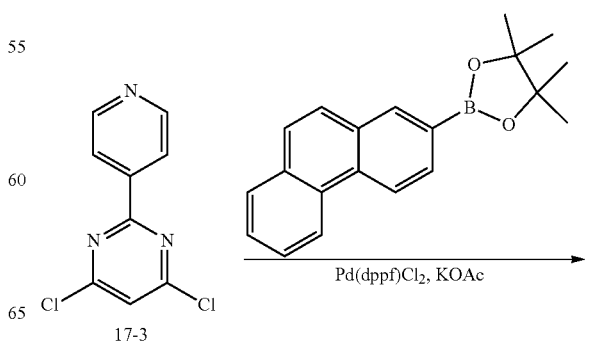

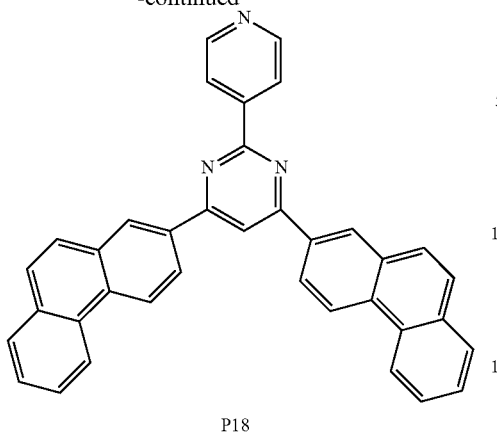

P18

(1) In a 250 ml round bottom flask, the compound 17-3 (15 mmol), potassium acetate (40 mmol), 2-phenanthreneboronic acid pinacol ester (15 mmol), dry 1,4-dioxane (60 ml), and Pd(dppf)Cl$_2$ (0.4 mmol) were mixed and reacted for 48 hours at 90° C. under nitrogen atmosphere while being stirred. The obtained intermediate was cooled to room temperature, then added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the product P18.

Characterization Results of Compound P18:

$^1$H NMR (400 MHz, CDCl$_3$): δ 8.99-8.70 (m, 16H), 8.65 (d, J=8.4 Hz, 2H), 8.43 (s, 2H), 7.60 (d, J=8.4 Hz, 2H), 7.64 (s, 1H).

Elemental analysis results (molecular formula: C$_{37}$H$_{23}$N$_3$): theoretical: a carbon atom, 87.23; H, 4.52; a nitrogen atom, 8.25; measured: a carbon atom, 87.03; H, 4.62; a nitrogen atom, 8.32. ESI-MS (m/z)(M+) obtained through Liquid Chromatography/Mass Spectrometry: theoretical, 509.19; measured, 509.13.

Example 4

Synthesis of Compound P82

The synthesis scheme of compound P82 is shown as below:

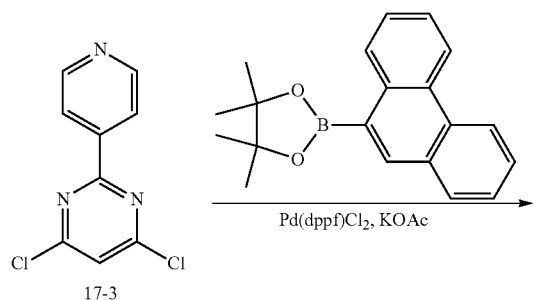

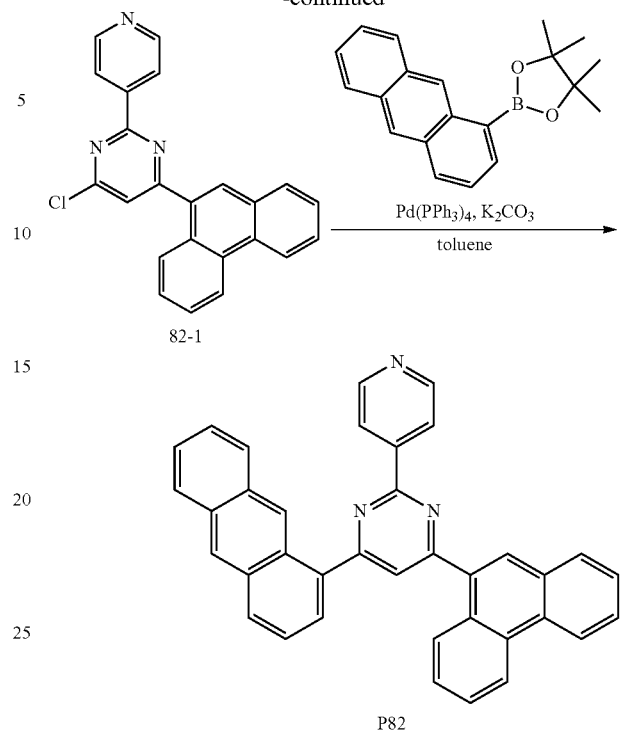

P82

(1) In a 250 ml round bottom flask, the compound 17-3 (15 mmol), potassium acetate (40 mmol), 9-phenanthreneboronic acid pinacol ester (15 mmol), dry 1,4-dioxane (60 ml), and Pd(dppf)Cl$_2$ (0.4 mmol) were mixed and reacted for 48 hours at 90° C. under nitrogen atmosphere while being stirred. The obtained intermediate was cooled to room temperature, then added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain a product 82-1.

(2) In a 250 ml round bottom flask, 1-anthraceneboronic acid pinacol ester (20 mmol), the product 82-1 (15 mmol), and Pd(PPh$_3$)$_4$ (0.3 mmol) were added to an aqueous solution of toluene (30 ml)/ethanol (20 ml) and potassium carbonate (12 mmol) and reacted for 12 hours under nitrogen atmosphere while being refluxed. The obtained mixture was cooled to room temperature, then added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the final product P82.

Characterization Results of Compound P82:

$^1$H NMR (400 MHz, CDCl$_3$): δ 8.93-8.52 (m, 8H), 8.65 (d, J=8.4 Hz, 2H), 8.31 (s, 2H), 7.93 (s, 1H), 7.91-7.39 (m, 7H), 7.65 (s, 1H), 7.60 (d, J=8.4 Hz, 2H);

Elemental analysis results (molecular formula: C$_{37}$H$_{23}$N$_3$): theoretical: a carbon atom, 87.23; H, 4.52; a nitrogen atom, 8.25; measured: a carbon atom, 87.03; H, 4.72; a nitrogen atom, 8.23. ESI-MS (m/z)(M+) obtained through Liquid Chromatography/Mass Spectrometry: theoretical, 509.19; measured, 508.98.

Example 5

Synthesis of Compound P103

The synthesis scheme of compound P103 is shown as below:

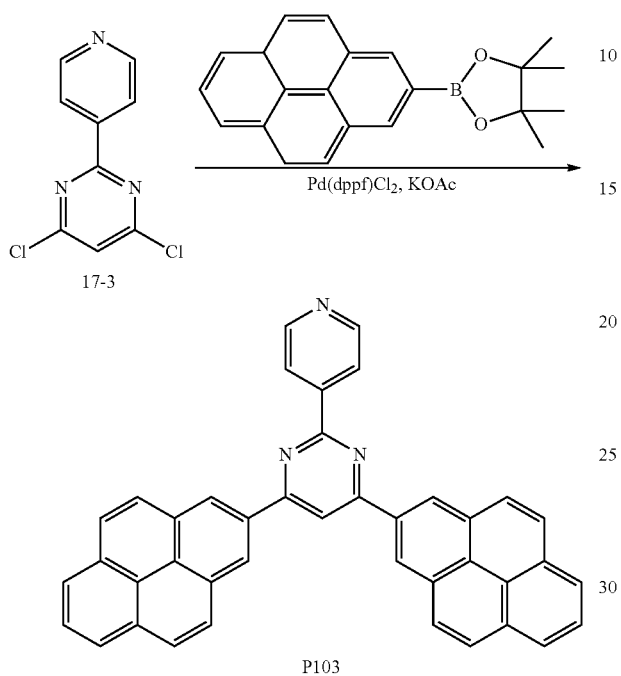

(1) In a 250 ml round bottom flask, the compound 17-3 (15 mmol), potassium acetate (40 mmol), 2-pyreneboronic acid pinacol ester (15 mmol), dry 1,4-dioxane (60 ml), and Pd(dppf)Cl$_2$ (0.4 mmol) were mixed and reacted for 48 hours at 90° C. under nitrogen atmosphere while being stirred. The obtained intermediate was cooled to room temperature, then added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the product P103.

Characterization Results of Compound P103:

$^1$H NMR (400 MHz, CDCl$_3$): δ 8.65 (d, J=8.4 Hz, 2H), 8.22 (s, 4H), 8.00-7.82 (m, 6H), 7.71 (d, J=8.4 Hz, 8H), 7.65 (s, 1H), 7.60 (d, J=8.4 Hz, 2H).

Elemental analysis results (molecular formula: C$_{41}$H$_{25}$N$_3$): theoretical: a carbon atom, 88.01; H, 4.47; a nitrogen atom, 7.51; measured: a carbon atom, 88.65; H, 4.14; a nitrogen atom, 7.62. ESI-MS (m/z)(M+) obtained through Liquid Chromatography/Mass Spectrometry: theoretical, 559.23; measured, 559.43.

Figure 2:
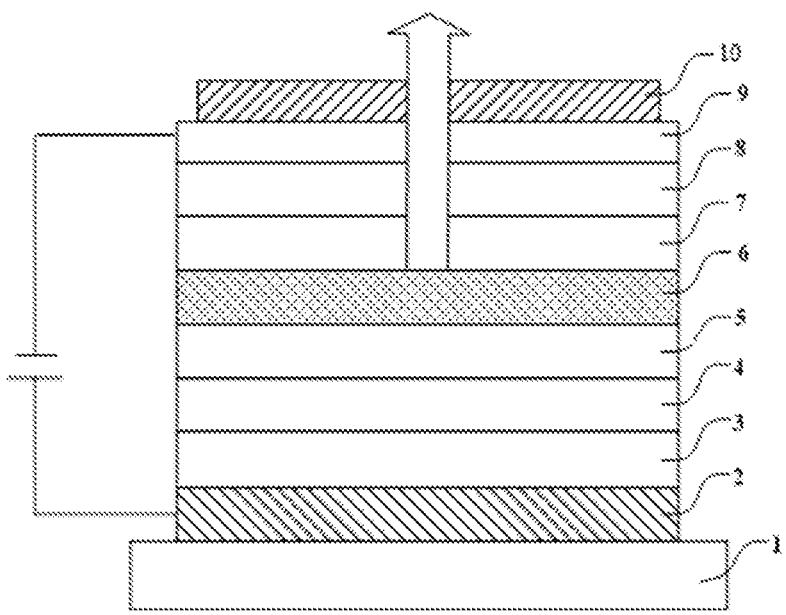
FIG. 2 is a structural schematic diagram of an OLED device according to an embodiment of the present disclosure.

An embodiment of the present disclosure provides an organic light-emitting device. As shown in FIG. 2, the organic light-emitting device includes: a substrate 1, an anode 2 (ITO), a hole injection layer 3, a first hole transmission layer 4, a second hole transmission layer 5, a light-emitting layer 6, an electron transmission layer 7, an electron injection layer 8, a cathode 9 (magnesium-silver electrode, Mg to Ag mass ratio 9:1), and a capping layer (CPL) 10. The ITO anode 2 has a thickness of 15 nm, the hole injection layer 3 has a thickness of 5 nm, the first hole transmission layer 4 has a thickness of 100 nm, the second hole transmission layer 5 has a thickness of 5 nm, the light-emitting layer 6 has a thickness of 30 nm, the electron transmission layer 7 has a thickness of 30 nm, the electron injection layer 8 has a thickness of 5 nm, the magnesium-silver electrode 9 has a thickness of 10 nm, and the capping layer (CPL) 10 has a thickness of 100 nm.

Device Example 1

This example provides an organic light-emitting device, which is specifically manufactured by the following steps:

1) A glass substrate was cut into a size of 50 mm×50 mm×0.7 mm, subjected to ultrasonic treatment respectively in isopropyl alcohol and in deionized water for 30 minutes, and then exposed to ozone for about 10 minutes for cleaning, so as to obtain the substrate 1. The obtained glass substrate with an indium tin oxide (ITO) anode 2 having a thickness of 15 nm was mounted on a vacuum deposition apparatus;

2) Compound 2 as a hole injection layer material and compound 1 as a p-dopant material, in a doping ratio of 3% by weight, were co-deposited by vacuum evaporation on the ITO anode layer 2, so as to form a hole injection layer 3 having a thickness of 5 nm;

3) Compound 3 as a hole transmission layer material was deposited by vacuum evaporation on the hole injection layer 3 to form a first hole transmission layer 4 having a thickness of 100 nm;

4) Compound 4 as the hole transmission material was deposited by vacuum evaporation on the first hole transmission layer 4 to form a second hole transmission layer 5 having a thickness of 5 nm;

5) Compound 5 as a host material, and compound 6 as a dopant, in a doping ratio of 3% by weight, were deposited by vacuum evaporation on the second hole transmission layer 5 to form a light-emitting layer 6 having a thickness of 30 nm;

6) Compound 7 as the electron transmission material was deposited by vacuum evaporation on the light-emitting layer 6 to form an electron transmission layer 7 having a thickness of 30 nm;

7) Compound 8 as an electron transmission material, and compound 9 as an n-dopant, in a doping mass ratio of 1:1, were co-deposited by vacuum evaporation on the electron transmission layer 7 to form an electron injection layer 8 having a thickness of 5 nm;

8) a magnesium-silver electrode (a ratio of Mg to Ag is 9:1) was deposited by vacuum evaporation on the electron injection layer 8 to form a cathode 9 having a thickness of 10 nm; and 9) Compound P1 of the present disclosure was deposited by vacuum evaporation on the cathode 9 to form a capping layer 10 having a thickness of 100 nm.

The compounds used in the organic light-emitting devices are listed below:

compound 1
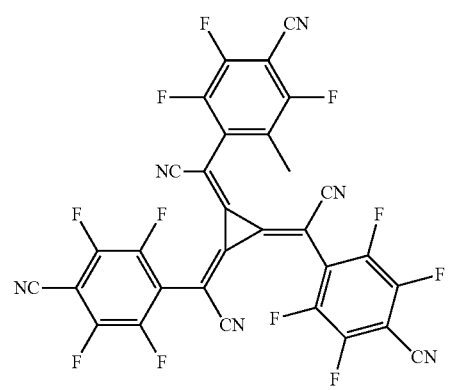
compound 4
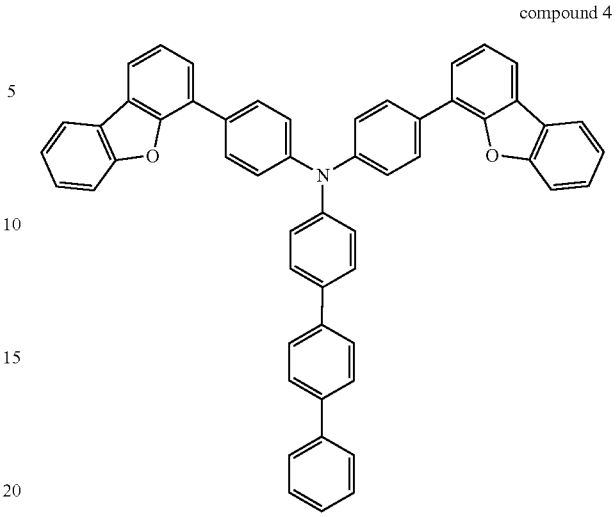
compound 2
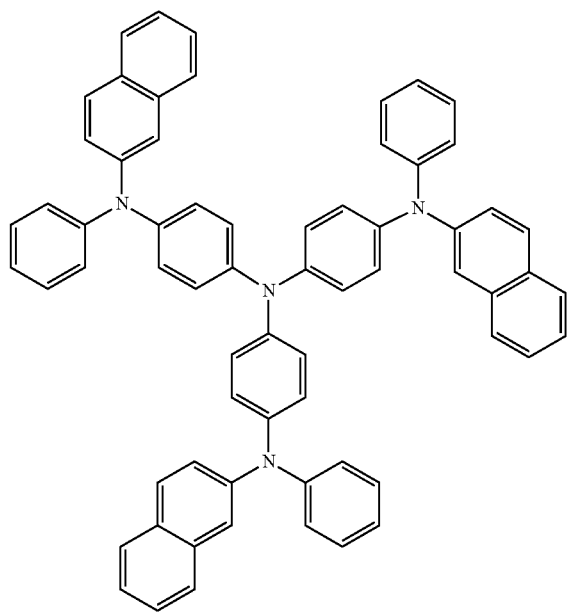
compound 5
compound 6
compound 3
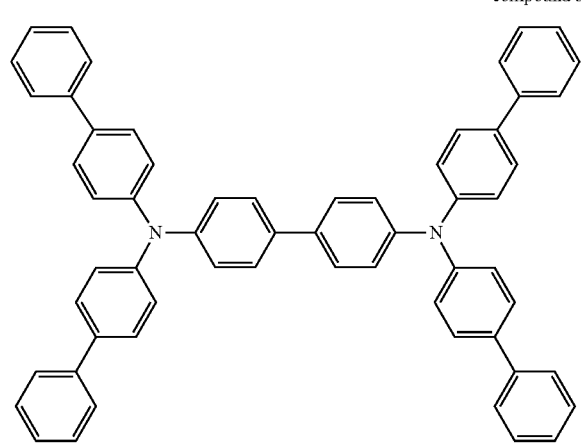
compound 7
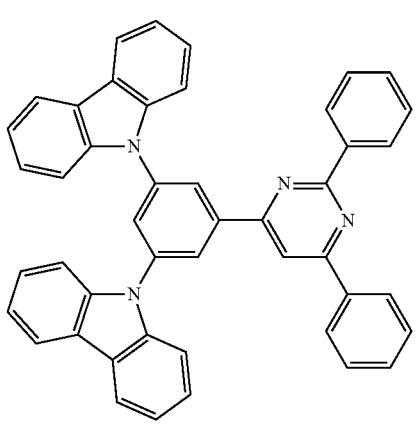

-continued compound 8

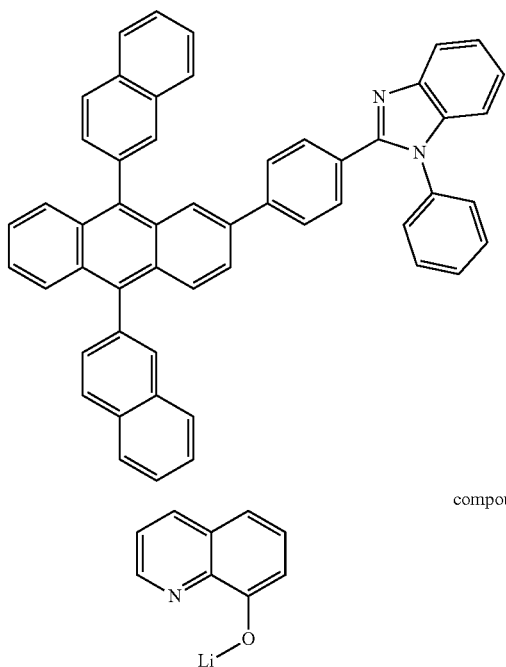

compound 9

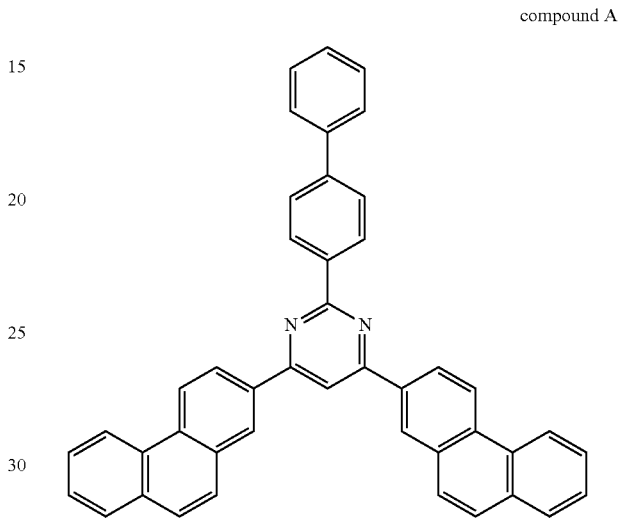

Device Example 2

Device Example 2 differs from Device Example 1 in that the compound P1 was replaced with compound P17.

Device Example 3

Device Example 3 differs from Device Example 1 in that the compound P1 was replaced with compound P18.

Device Example 4

Device Example 4 differs from Device Example 1 in that the compound P1 was replaced with compound P36.

Device Example 5

Device Example 5 differs from Device Example 1 in that the compound P1 was replaced with compound P82.

Device Example 6

Device Example 6 differs from Device Example 1 in that the compound P1 was replaced with compound P100.

Device Example 7

Device Example 7 differs from Device Example 1 in that the compound P1 was replaced with compound P101.

Device Example 8

Device Example 8 differs from Device Example 1 in that the compound P1 was replaced with compound P103.

Device Example 9

Device Example 9 differs from Device Example 1 in that the compound P1 was replaced with compound P106.

Device Comparative Example 1

Device Comparative Example 1 differs from Device Example 1 in that the compound P1 was replaced with compound A.

compound A

Device Comparative Example 2

Device Comparative Example 2 differs from Device Example 1 in that the compound P1 was replaced with compound B.

compound B

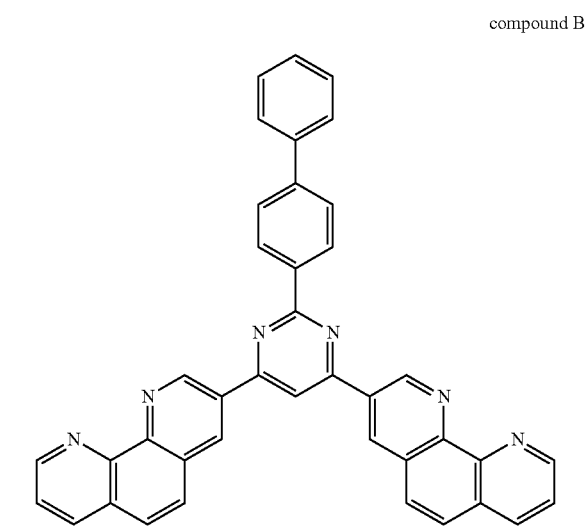 [SMILES: c1ccc(-c2ccc(-c3nc(-c4cnc5c(ccc6cccnc65)c4)cc(-c4cnc5c(ccc6cccnc65)c4)n3)cc2)cc1]

Tests of Performances:
(1) The compounds, which were used as the capping layer in the device examples and the device comparative examples, were tested in terms of glass transition temperature $T_g$, the refractive index n, and the extinction coefficient k. The results are shown in Table 1. The glass transition temperature $T_g$ was measured by the differential scanning calorimetry (DSC, Waters Technology (Shanghai) Co., Ltd., PerkinElmer DSC 8000 Differential Scanning Calorimeter), with a heating rate of 10 C/mmn. The refractive index n and the extinction coefficient k were measured under atmospheric environment by an ellipsometer (J. A. Woollam Co., USA; Model: ALPHA-SE). The tested results are shown in Table 1.

TABLE 1

| No. | Compound | $T_g$/° C. | 450 nm n | 450 nm k | 550 nm n | 550 nm k | 630 nm n | 630 nm k |
|---|---|---|---|---|---|---|---|---|
| Device Example 1 | P1 | 150 | 2.35 | 0.015 | 2.27 | 0.008 | 2.20 | 0.000 |
| Device Example 2 | P17 | 157 | 2.32 | 0.016 | 2.24 | 0.009 | 2.15 | 0.000 |
| Device Example 3 | P18 | 151 | 2.31 | 0.015 | 2.22 | 0.000 | 2.13 | 0.000 |
| Device Example 4 | P36 | 153 | 2.43 | 0.008 | 2.29 | 0.000 | 2.20 | 0.000 |
| Device Example 5 | P82 | 152 | 2.35 | 0.016 | 2.23 | 0.006 | 2.18 | 0.000 |
| Device Example 6 | P100 | 151 | 2.37 | 0.012 | 2.22 | 0.010 | 2.12 | 0.000 |
| Device Example 7 | P101 | 155 | 2.20 | 0.034 | 2.13 | 0.008 | 2.00 | 0.000 |
| Device Example 8 | P103 | 172 | 2.24 | 0.046 | 2.13 | 0.015 | 2.08 | 0.000 |
| Device Example 9 | P106 | 159 | 2.49 | 0.042 | 2.34 | 0.014 | 2.28 | 0.000 |
| Device Comparative Example 1 | Compound A | 150 | 2.02 | 0.053 | 1.88 | 0.031 | 1.81 | 0.000 |
| Device Comparative Example 2 | Compound B | 153 | 2.45 | 0.061 | 2.21 | 0.013 | 2.08 | 0.000 |

As can be seen from Table 1 above, for visible light having a wavelength of 450-630 nm, the refractive indexes of the compounds P1, P17, P18, P36, P82, P100, P101, P103, and P106 of the present disclosure are all greater than 2.0, satisfying the refractive index requirements on the CPL of the light-emitting devices. Compared with compound A and compound B, the CPL materials of the present disclosure have higher refractive indexes. In addition, the glass transition temperatures of the compounds P1, P17, P18, P36, P82, P100, P101, P103, and P106 of the present disclosure are all higher than or equal to 150° C. That is, the compounds of the present disclosure have very high thermal stability, and thus the organic light-emitting devices have a longer service life. Further, the extinction coefficient k of the compounds of the present disclosure is less than or equal to 0.05, and thus the compounds are suitable for use as the CPL materials, thereby improving the light extraction efficiency and the light-emitting efficiency of the display panel.

(2) Performance Evaluation of Organic Light-Emitting Devices

A Keithley 2365A digital nanovoltmeter was used to measure the currents of the display panels manufactured according to the examples and comparative examples at different voltages. The currents were divided by the light-emitting area to calculate current densities of the organic light-emitting device at different voltages. Konica Minolta CS-2000 spectroradiometer was used to measure the brightness and the radiant energy flux density of organic light-emitting devices manufactured according to the examples and comparative examples at different voltages. According to the current densities and brightness of the organic light-emitting devices at different voltages, an operating voltage Von, a current efficiency (CE, Cd/A), and an external quantum efficiency EQE under the same current density (10 mA/cm$^2$) were obtained. The service life LT95 was obtained by measuring a lasting time period before the brightness of the organic light-emitting device was reduced to 95% of an initial brightness (measured at 50 mA/cm$^2$).

The performance test results of the organic light-emitting devices are shown in Table 2.

TABLE 2

| No. | CPL material | Drive voltage (V) | CE (cd/A) | Service life LT95 |
|---|---|---|---|---|
| Device Example 1 | P1 | 3.61 | 6.5 | 71 |
| Device Example 2 | P17 | 3.79 | 7.0 | 69 |
| Device Example 3 | P18 | 3.64 | 6.6 | 68 |
| Device Example 5 | P82 | 3.72 | 6.5 | 66 |
| Device Example 6 | P100 | 3.66 | 6.8 | 70 |
| Device Example 7 | P101 | 3.81 | 6.4 | 63 |
| Device Example 8 | P103 | 3.65 | 7.2 | 69 |
| Device Example 9 | P106 | 3.67 | 6.9 | 73 |
| Device Comparative Example 1 | Compound A | 4.06 | 5.2 | 52 |
| Device Comparative Example 2 | Compound B | 4.60 | 4.6 | 42 |

Notes: CE: Current Efficiency

LT95: A parameter indicating the life time of an organic light-emitting device, and means a time required for OLED brightness to decrease to 95% of initial brightness.

Figure 3:
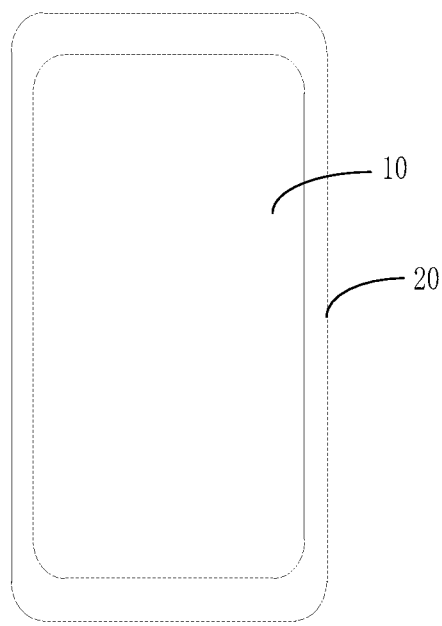
FIG. 3 is a schematic diagram of a display apparatus according to an embodiment of the present disclosure.

As can be seen from Table 2 above, the light-emitting devices using the compounds of the present disclosure as the CPL material having much lower drive voltages than the comparative devices, indicating that the compounds of the present disclosure can effectively reduce the power consumption of the light-emitting device. Compared with the comparative device, the current efficiencies of the light-emitting devices using the compound of the present disclosure as the CPL material are significantly improved. The present disclosure further provides a display apparatus including the organic light-emitting display panel described above. The organic light-emitting device of the present disclosure may be an OLED used in an organic light-emitting display apparatus. The organic light-emitting display apparatus may be a display screen of mobile phone, computer, TV, smart watch, smart car, VR or AR helmet, or other smart devices. FIG. 3 is a schematic diagram of a display apparatus according to an embodiment of the present disclosure. In FIG. 3, a mobile phone display panel is denoted with 10, and a display apparatus is denoted with 20.

What is claimed is:
1. A nitrogen-heterocyclic compound being any one of the following compounds:
P1
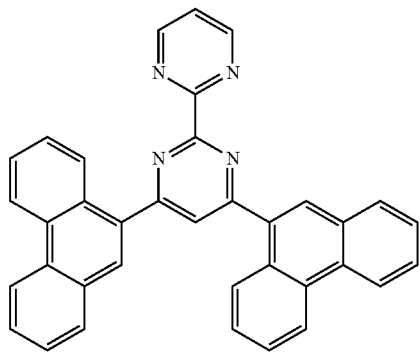
P2
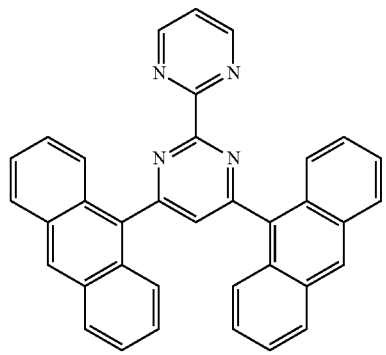
P3
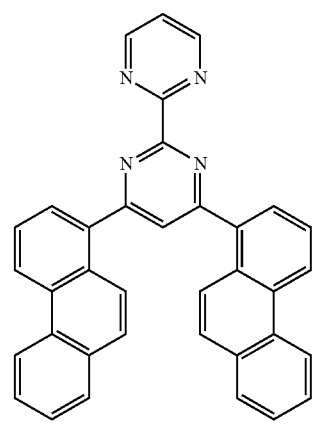
P4
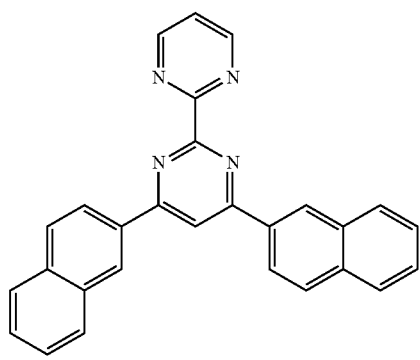
-continued
P5
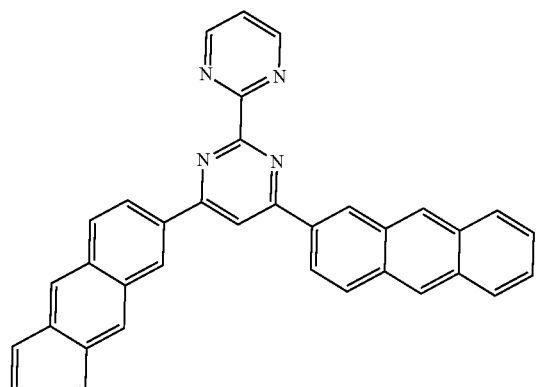
P6
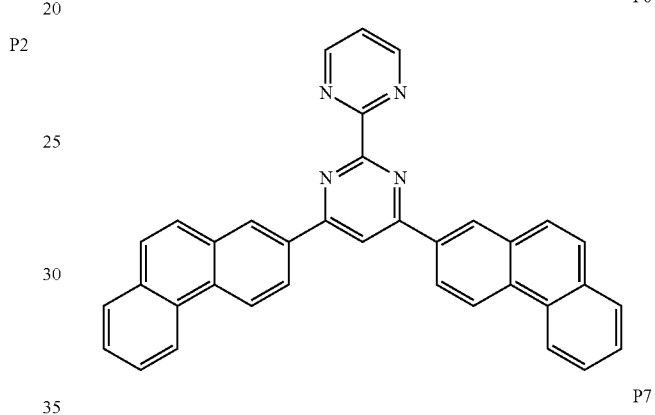
P7
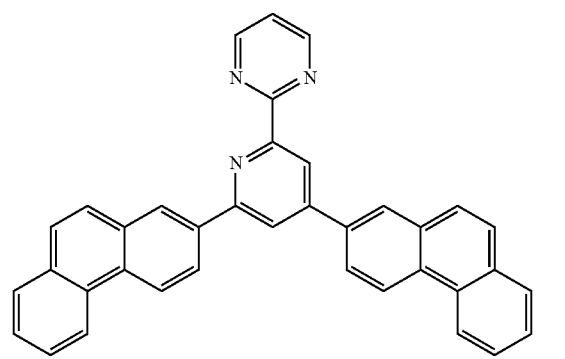
P8
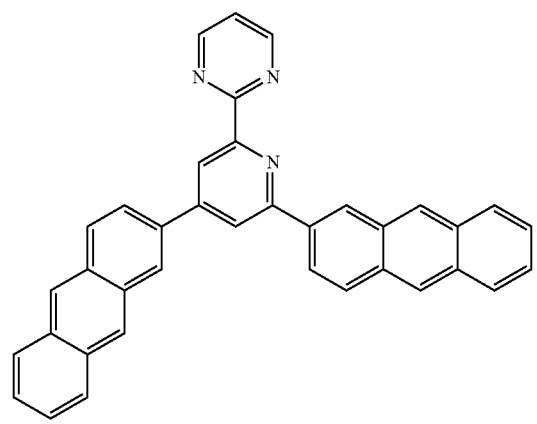

-continued
P9
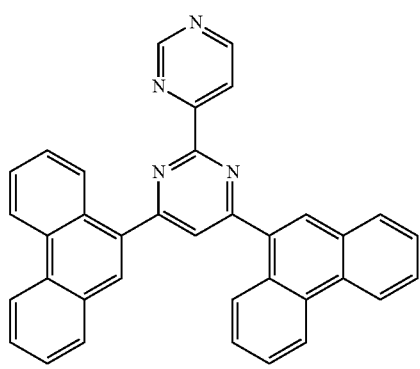
P10
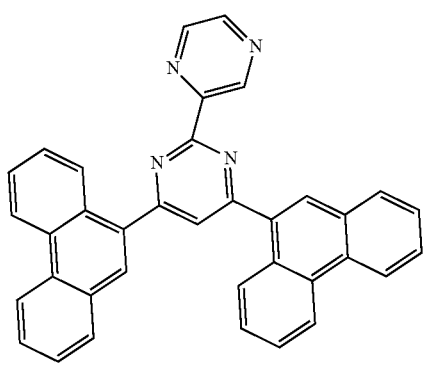
P11
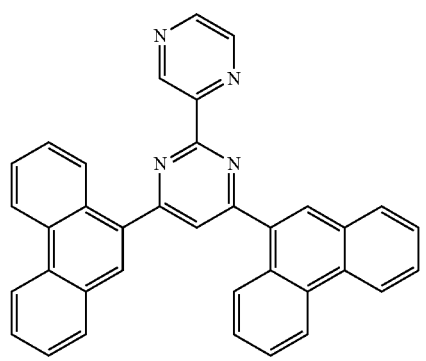
P12
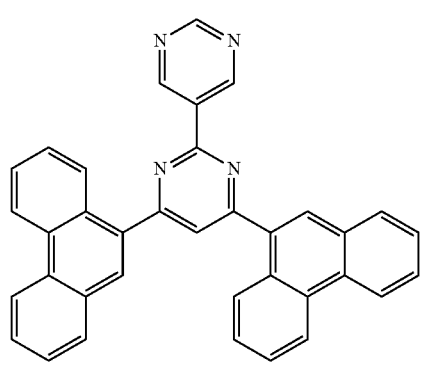
-continued
P13
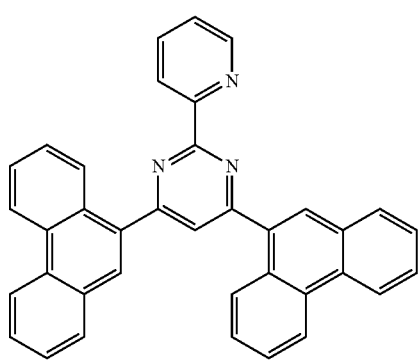
P14
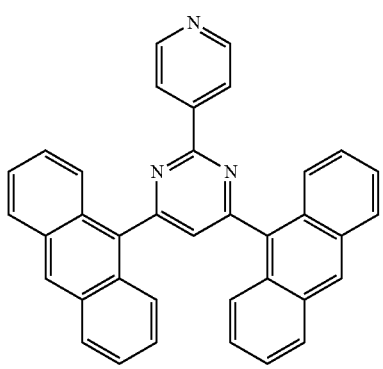
P15
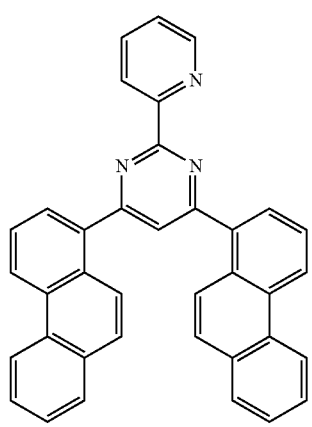
P16
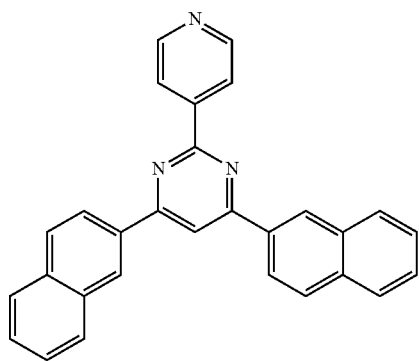

P17
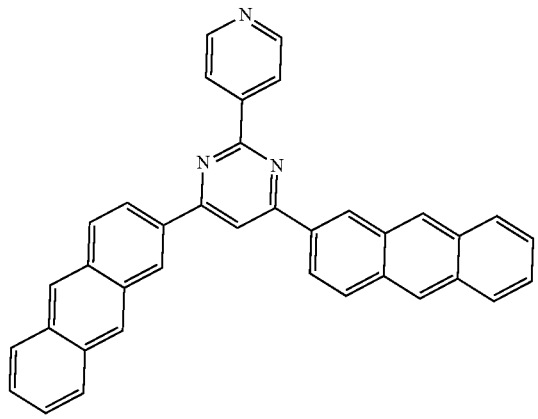
P18
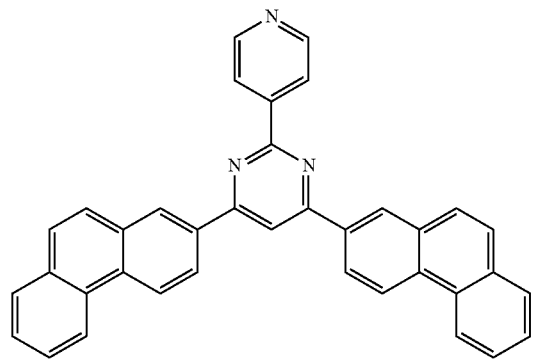
P19
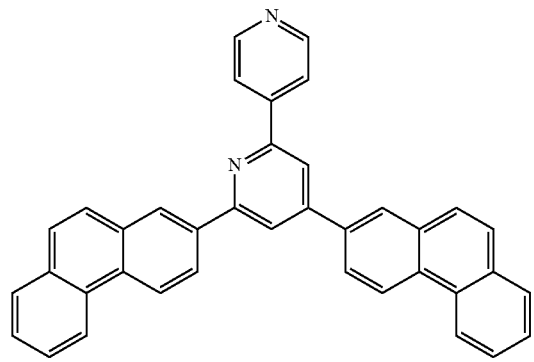
P20
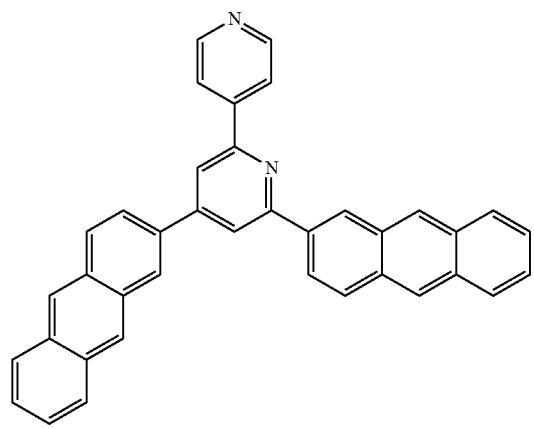
P21
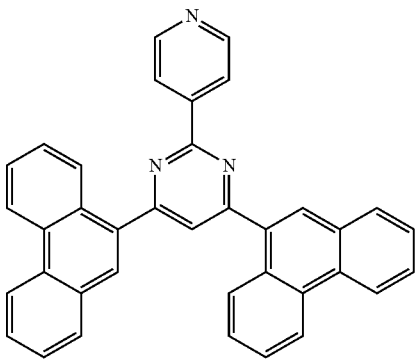
P22
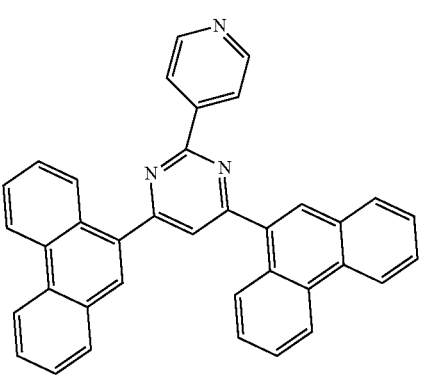
P23
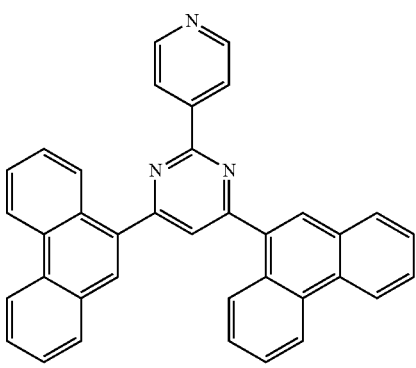
P24
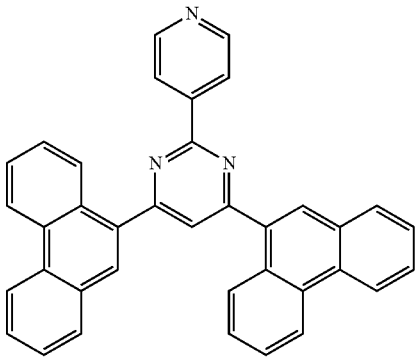

P25
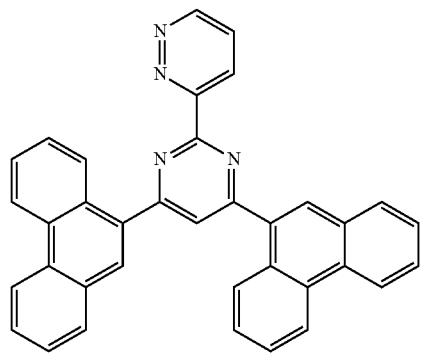
P26
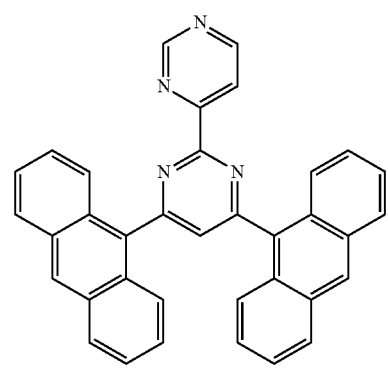
P27
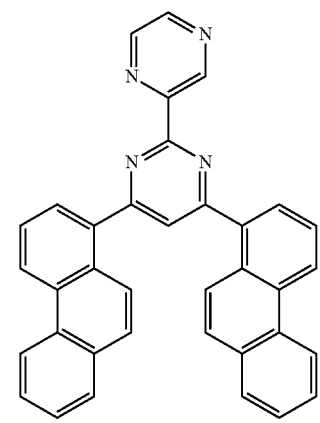
P28
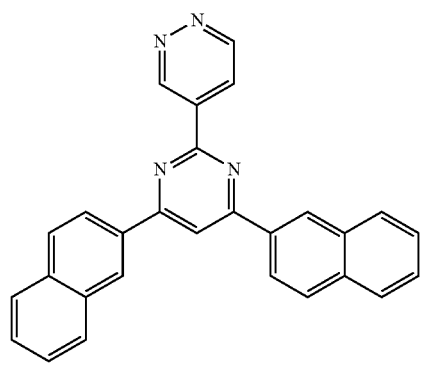
P29
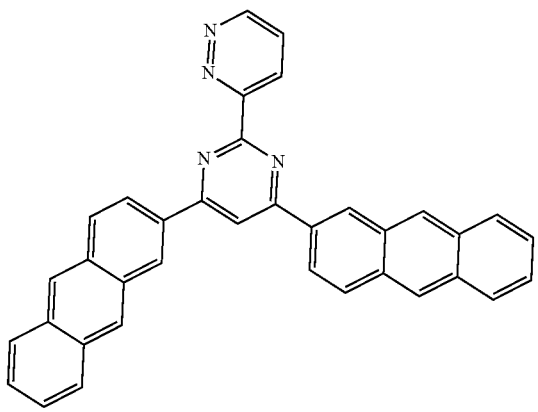
P30
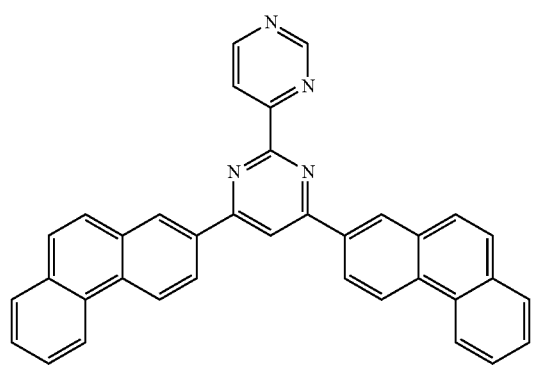
P31
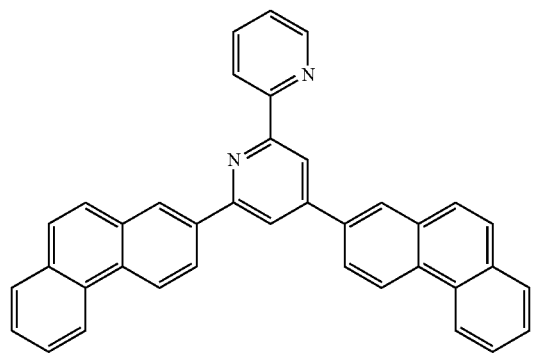
P32
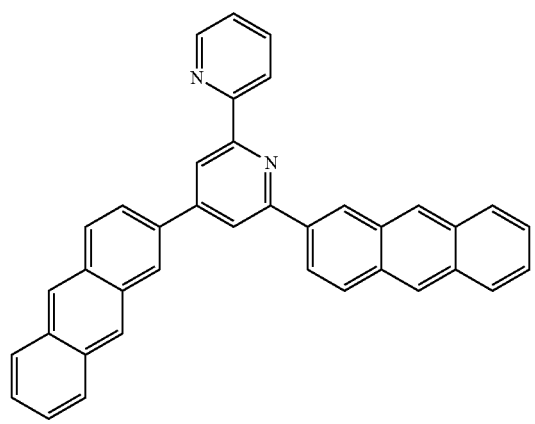

-continued
P33
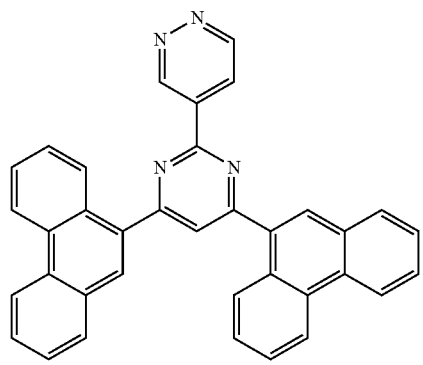
P34
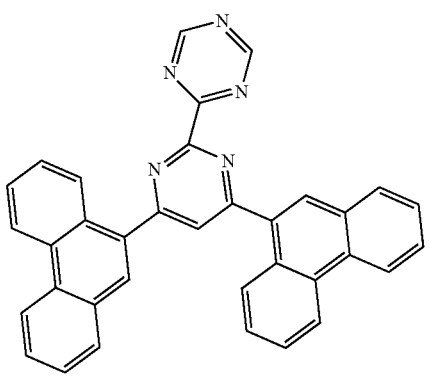
P35
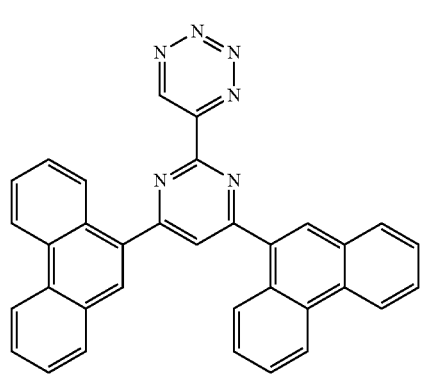
P36
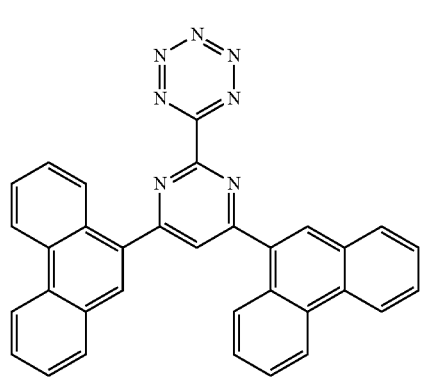
P37
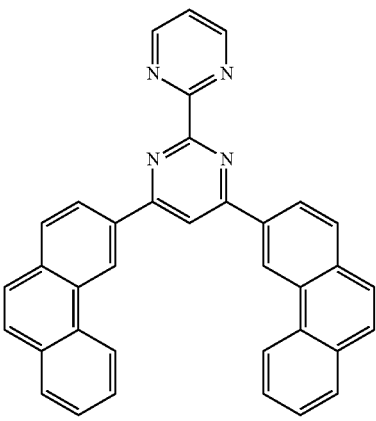
P38
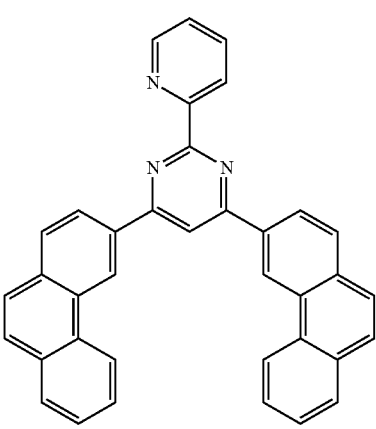
P39
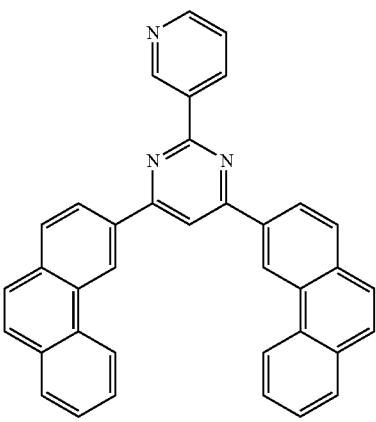

-continued
P40
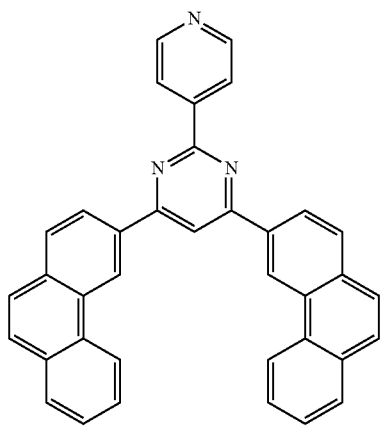
P41
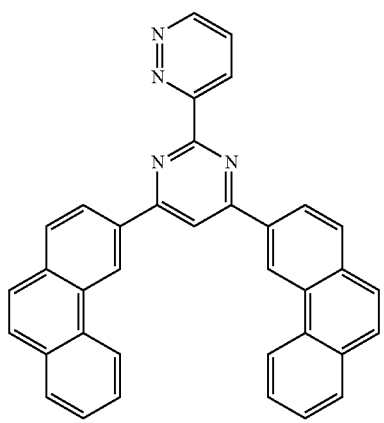
P42
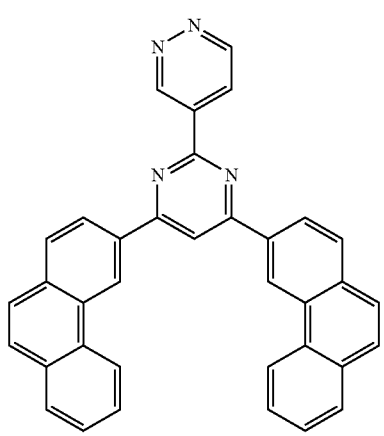
-continued
P43
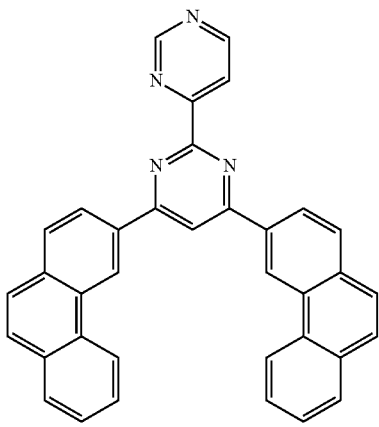
P44
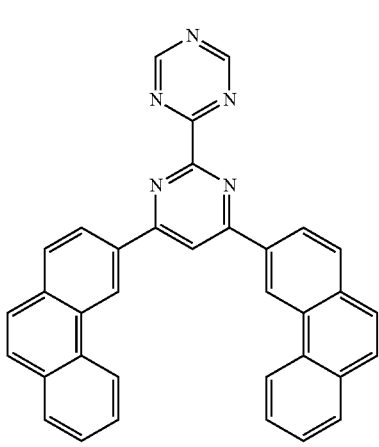
P45
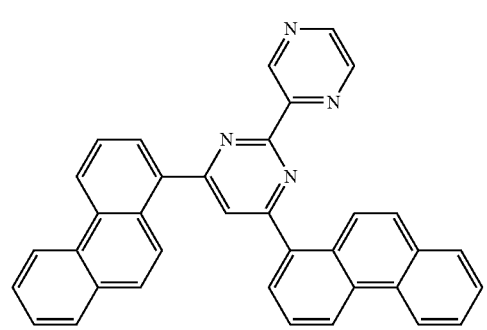
P46
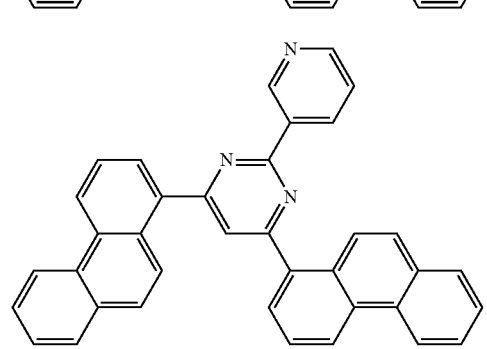

P47 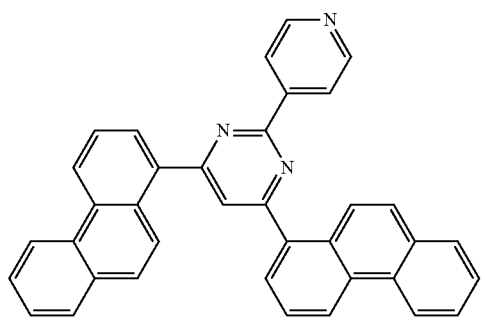
P48 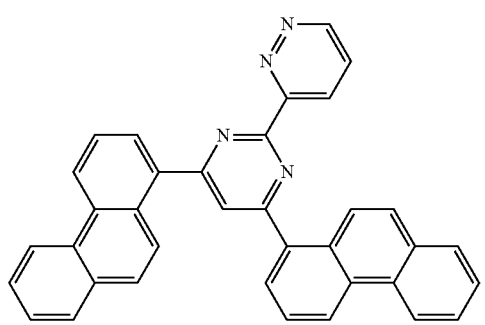
P49 
P50 
P51
P52 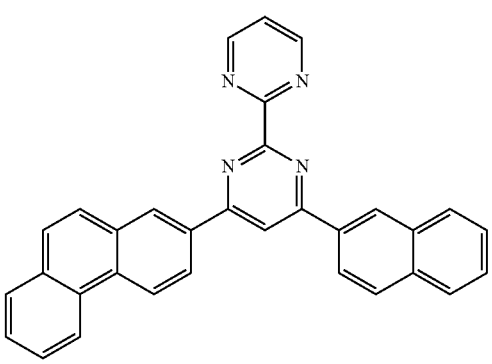
P53 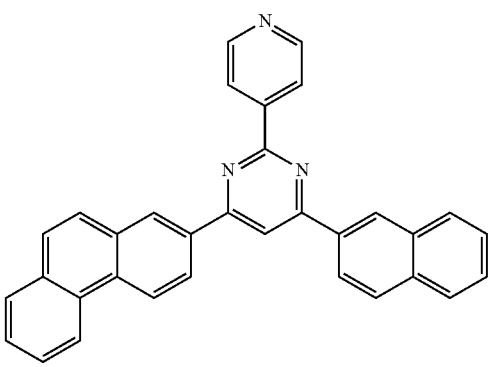
P54 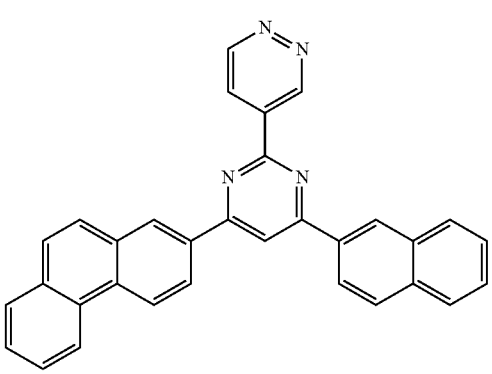
P55 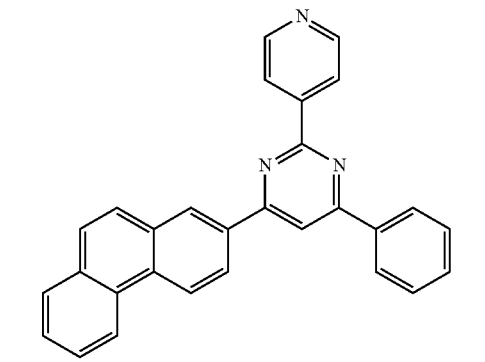

-continued
P56
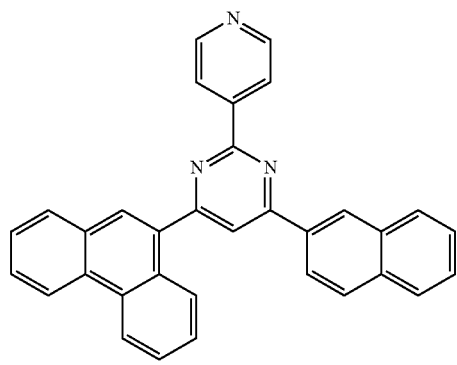
P57
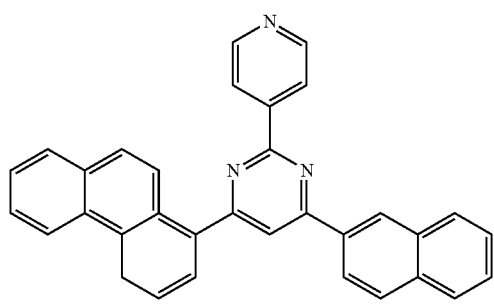
P58
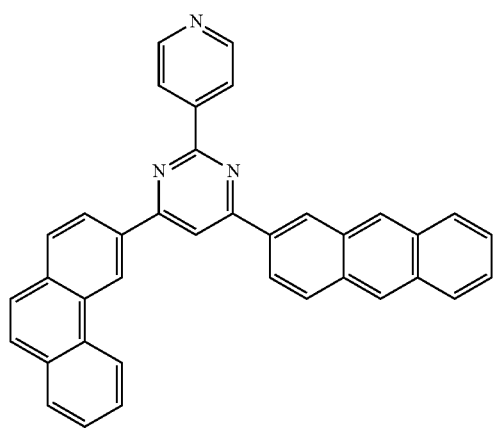
P59
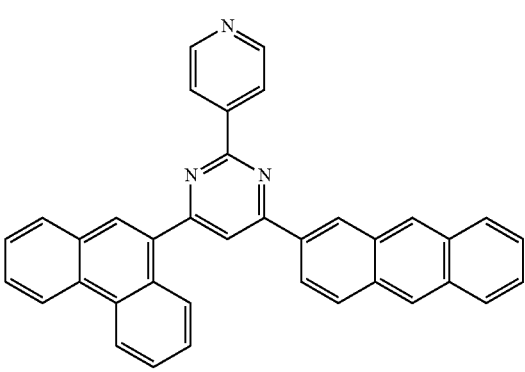
-continued
P60
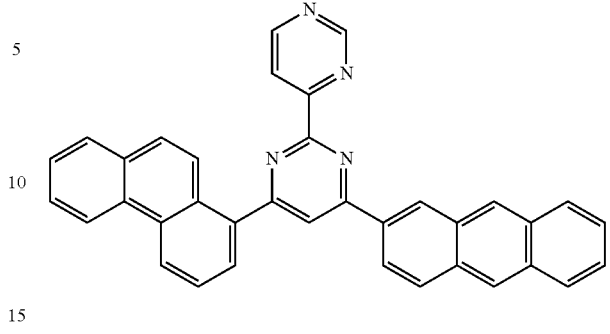
P61
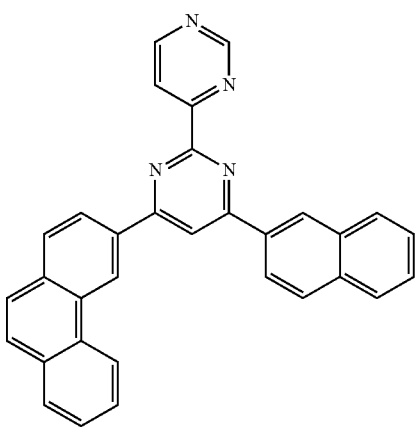
P62
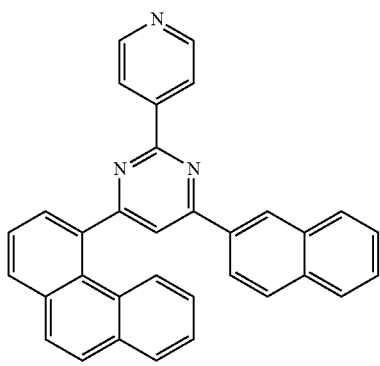
P63
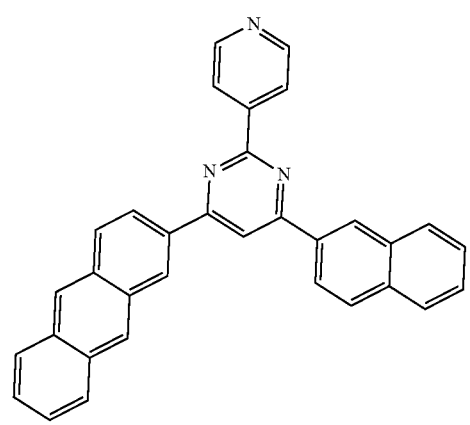

-continued
P64
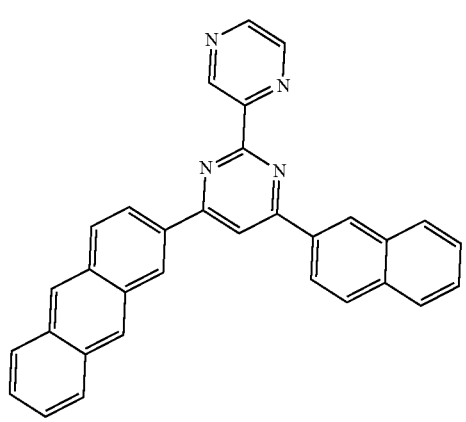
P65
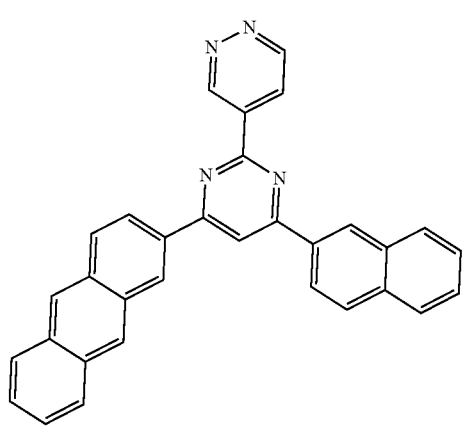
P66
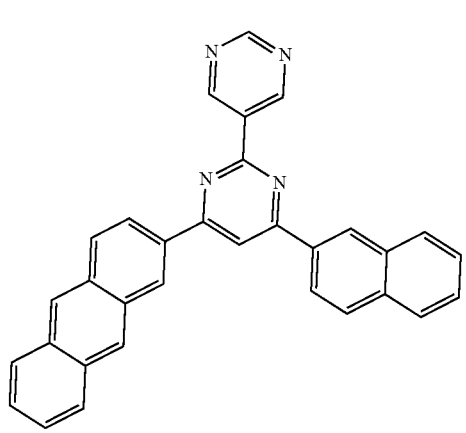
P67
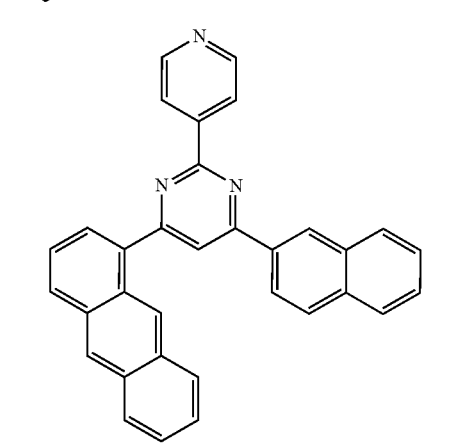
-continued
P68
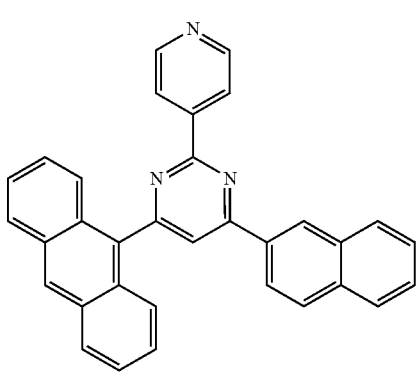
P69
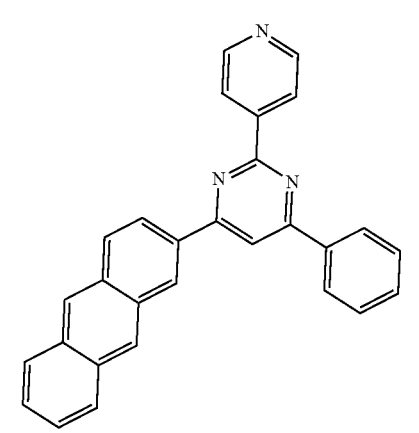
P70
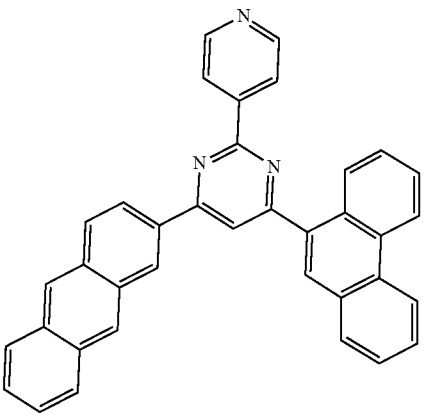
P71
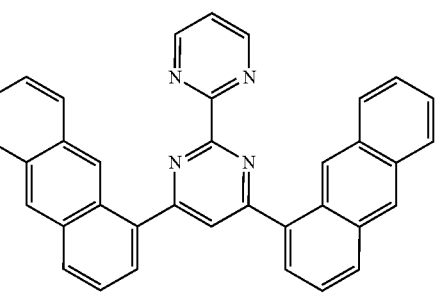

-continued
P72
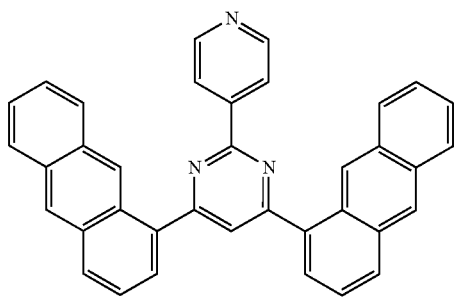
P73
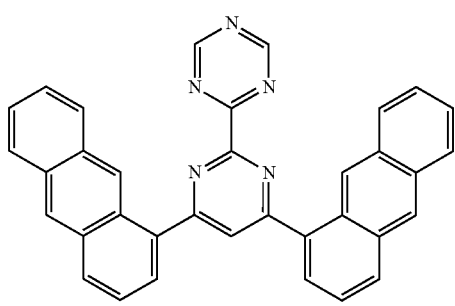
P74
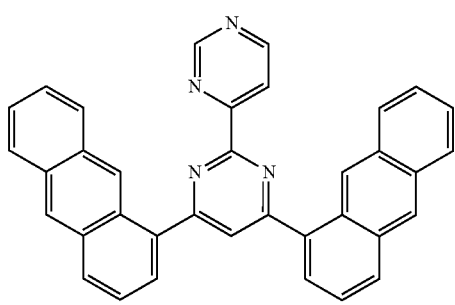
P75
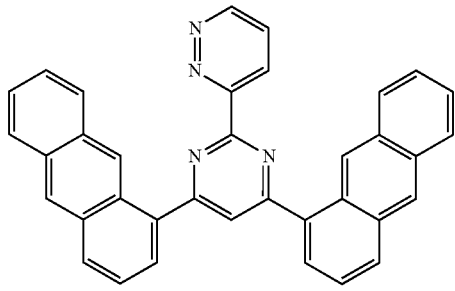
P76
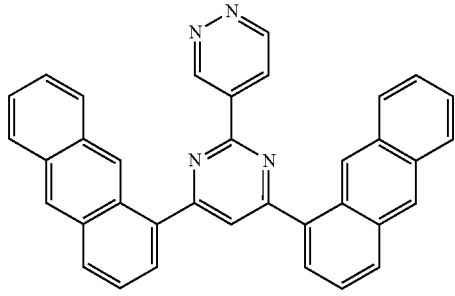
-continued
P77
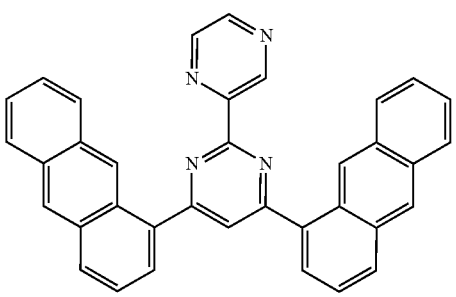
P78
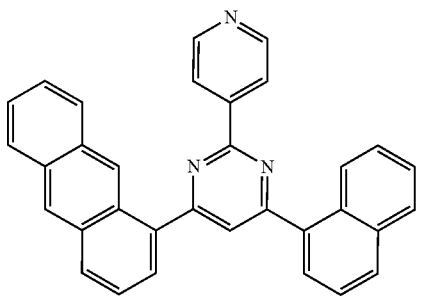
P79
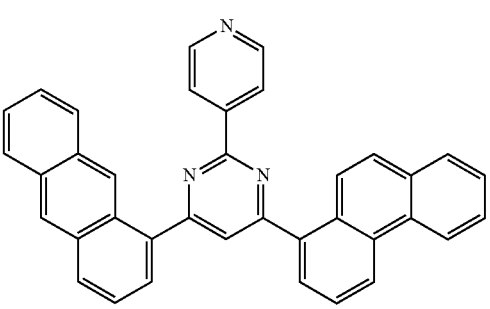
P80
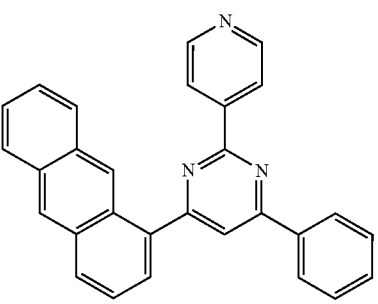
P81
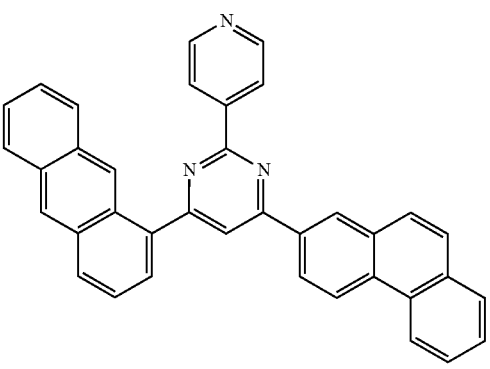

P82
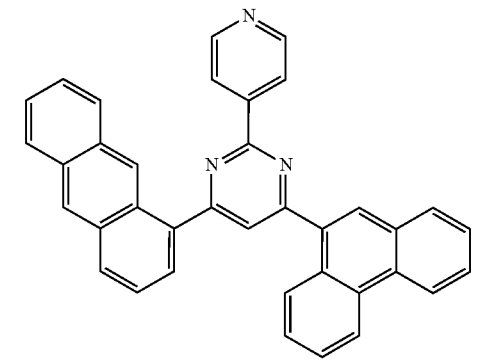
P83
P84
P85
P86
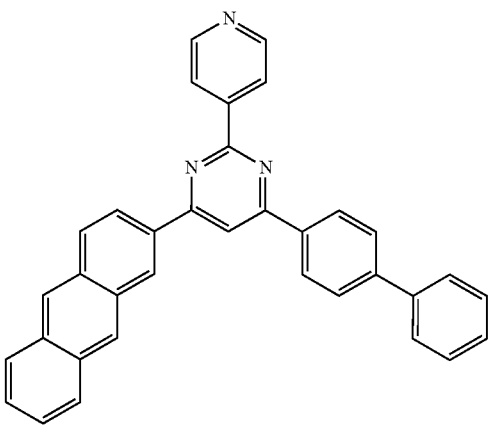
P87
P88
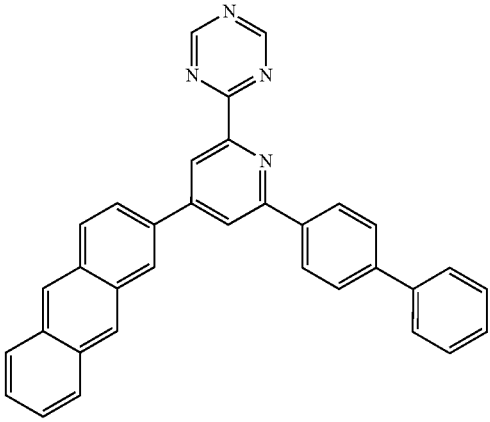
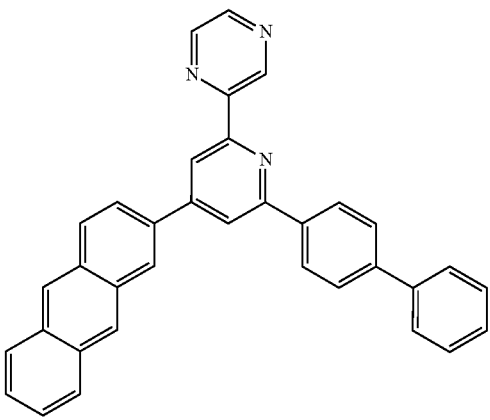

P89
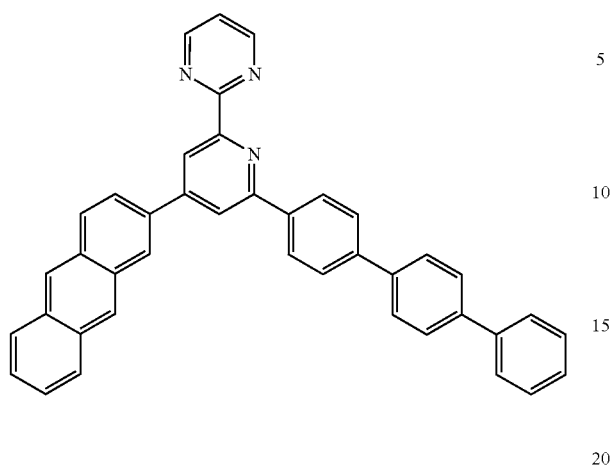
P90
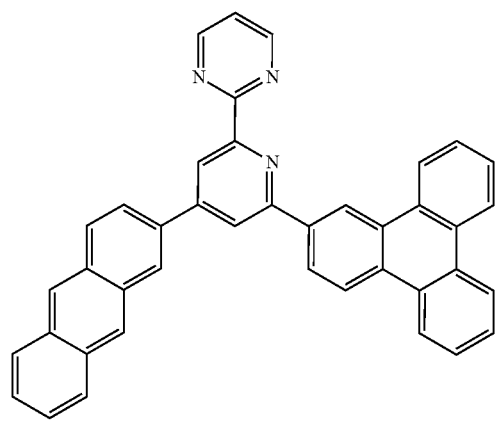
P91
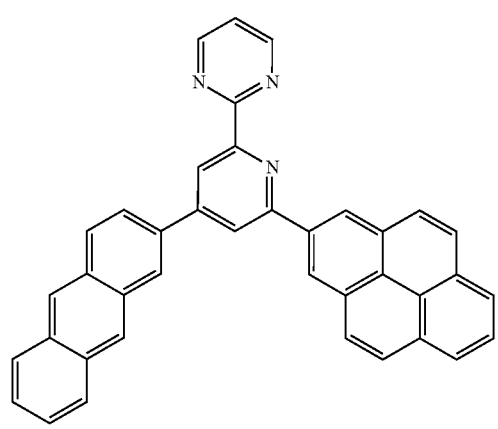
P92
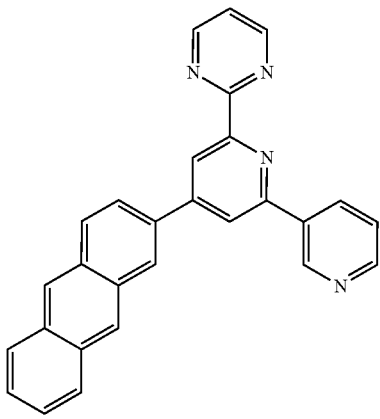
P93
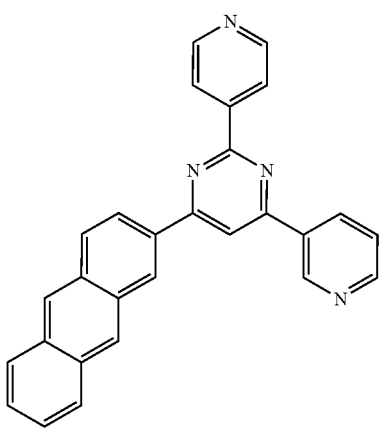
P94
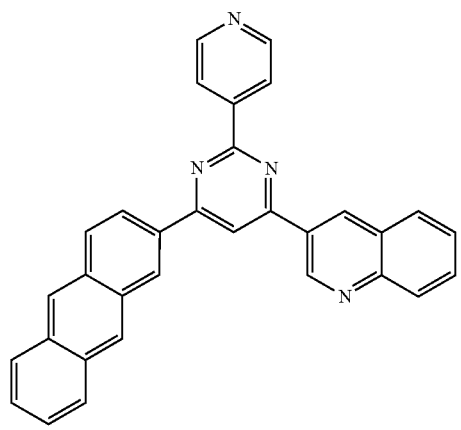

P95
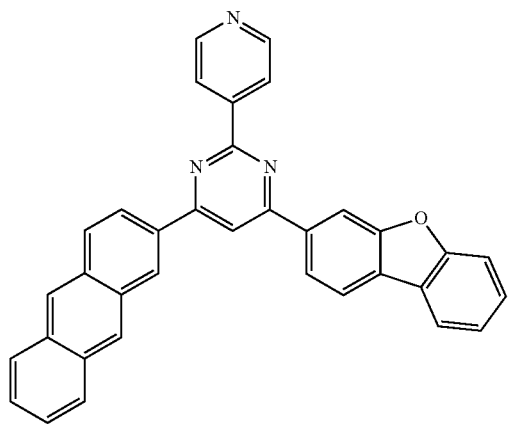
P96
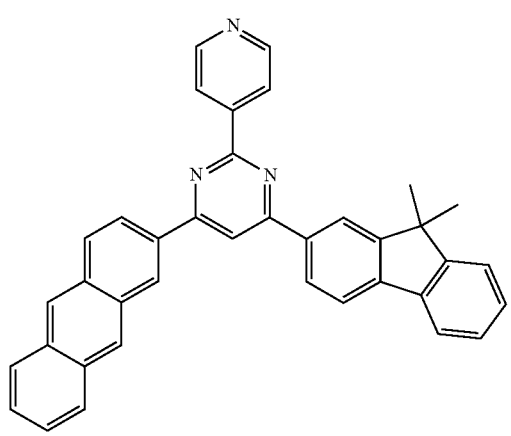
P97
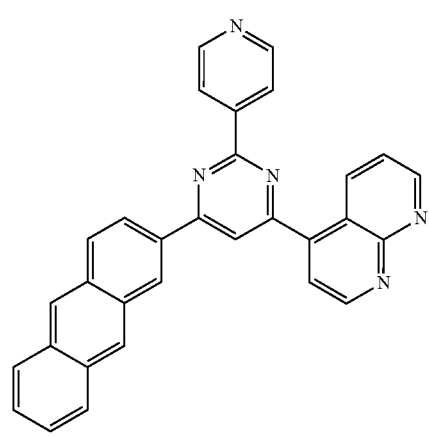
P98
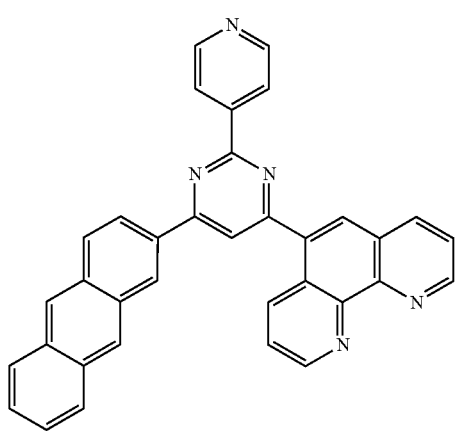
P99
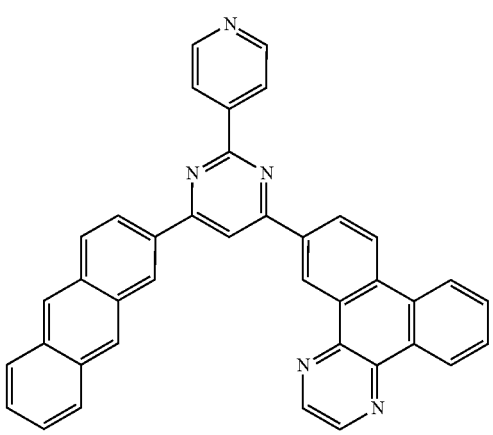
P100
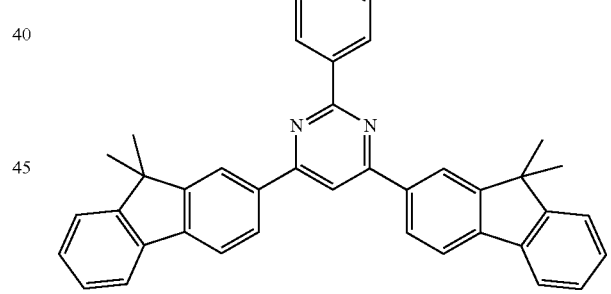
P101
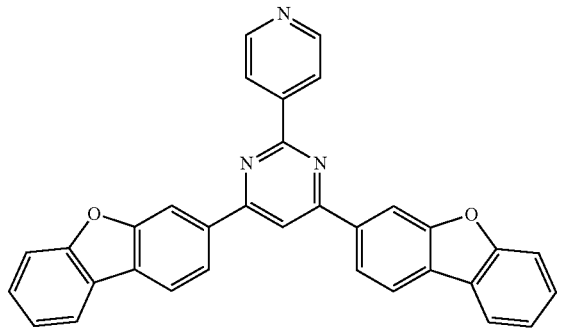

P102
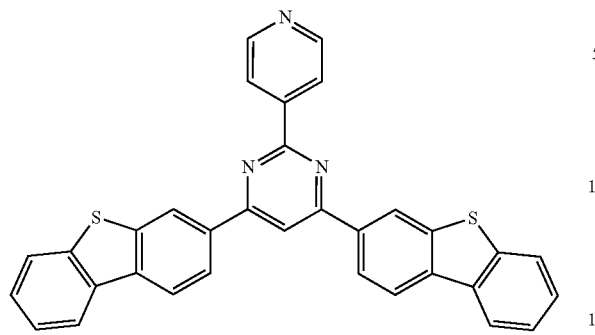
P103
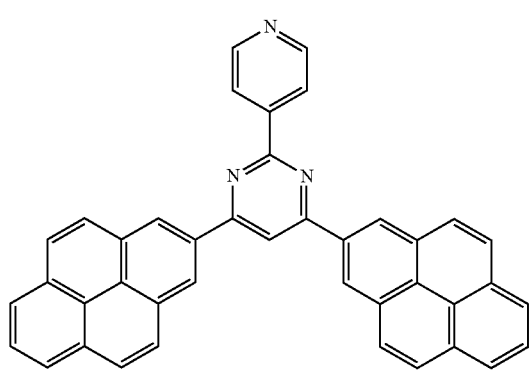
P104
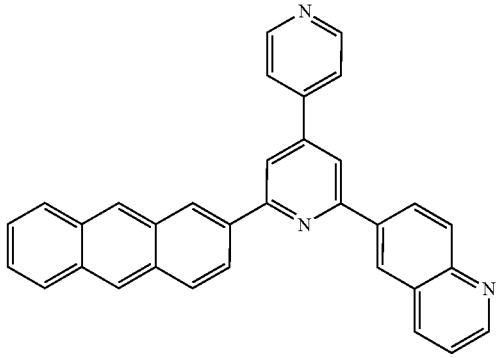
P105
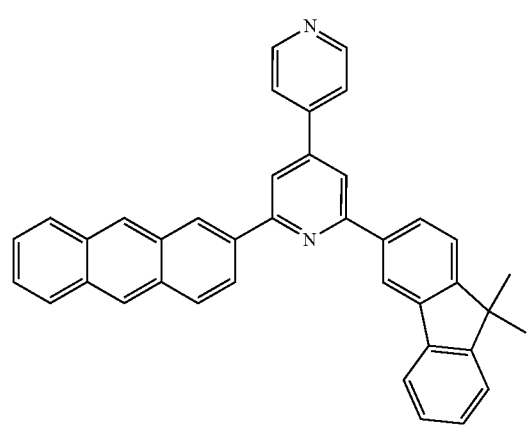
P106
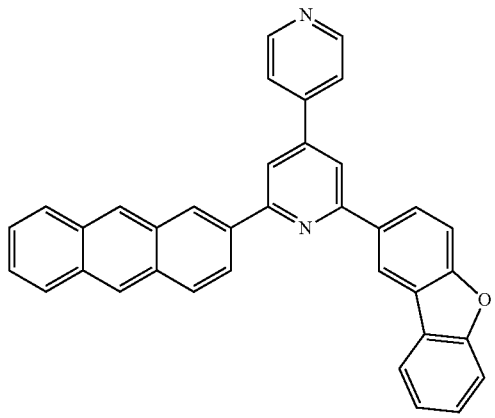
P107
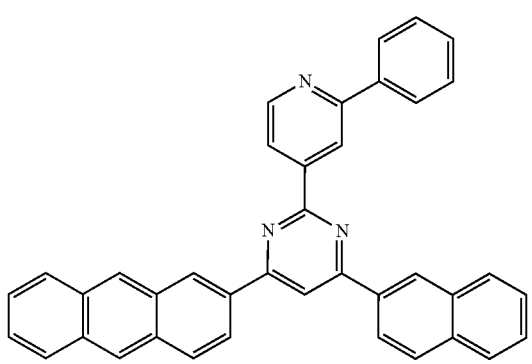
P108
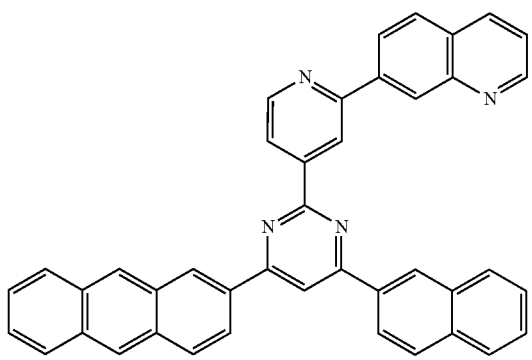
P109
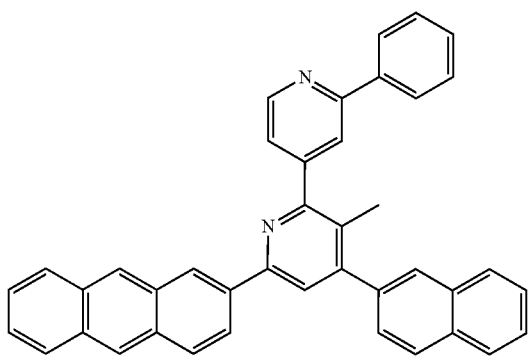

P110
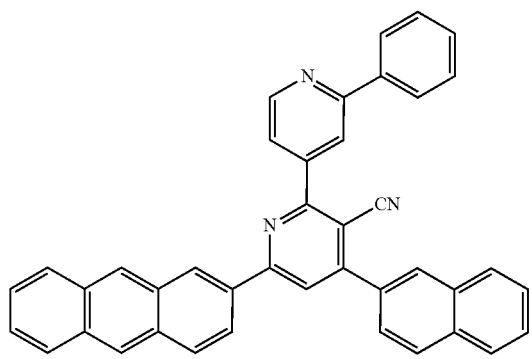
P111
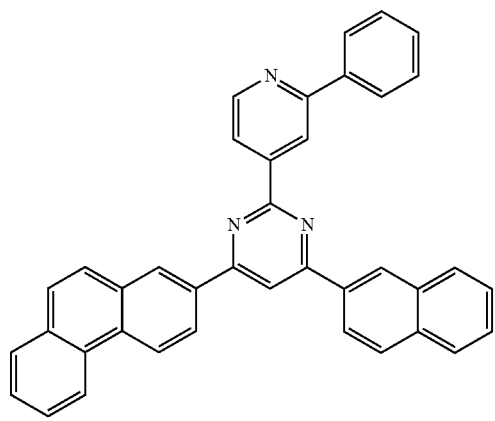
P112
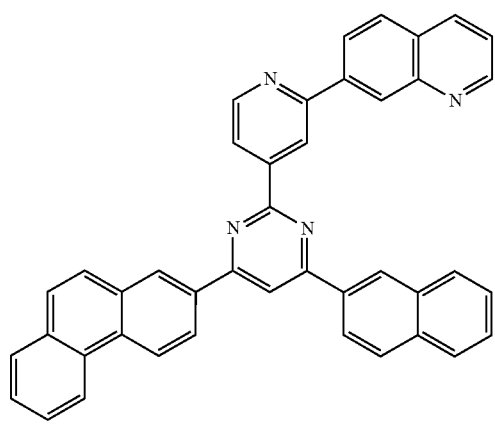
P113
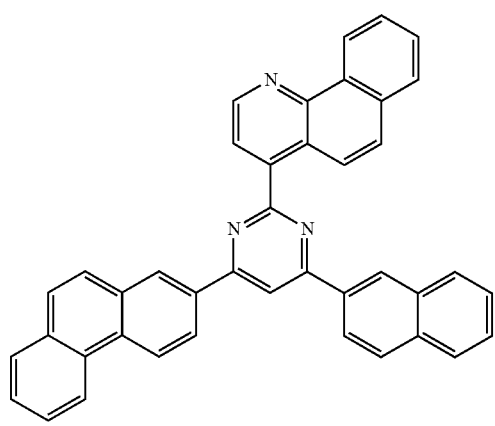
P114
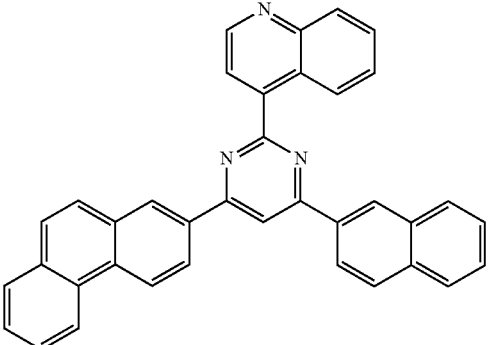
P115
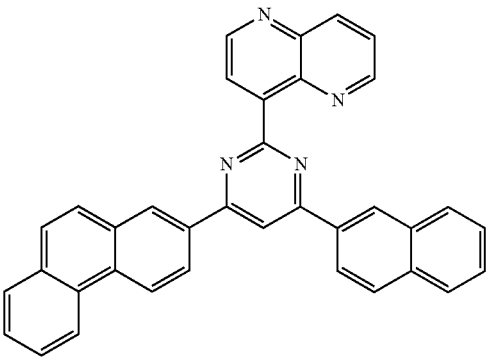
P116
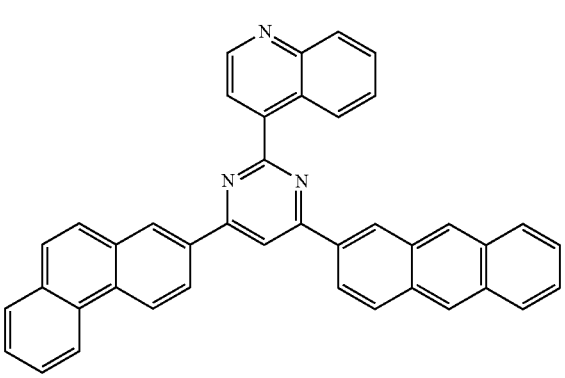
P117
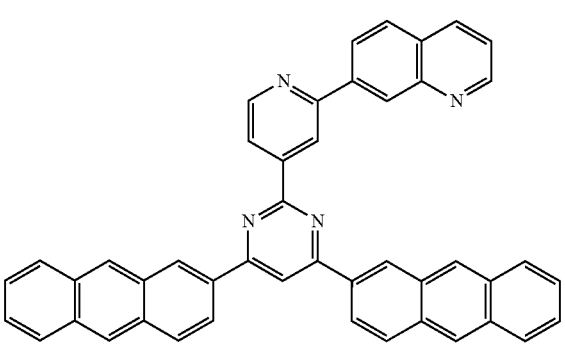

P118
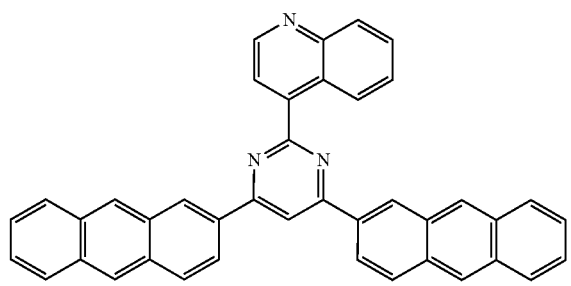
P119
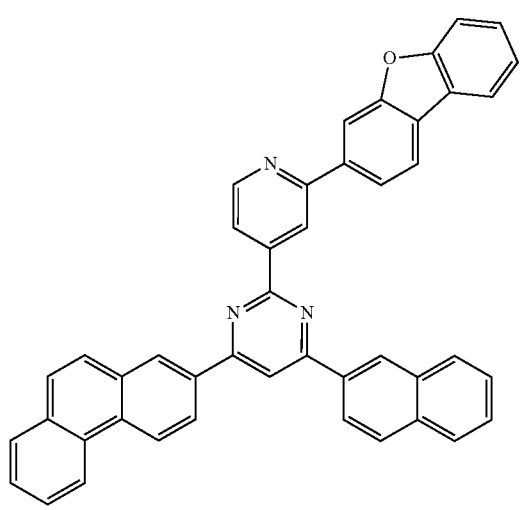
P120
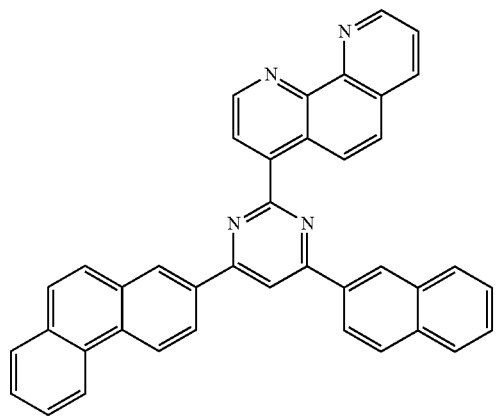
P121
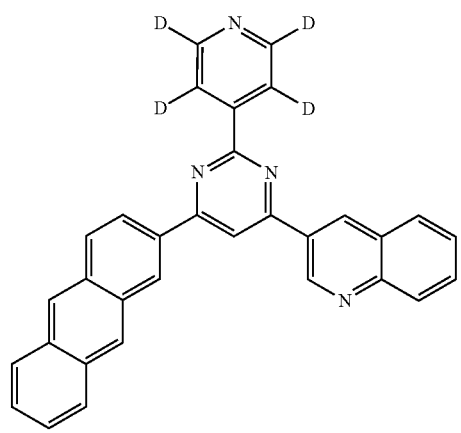
P122
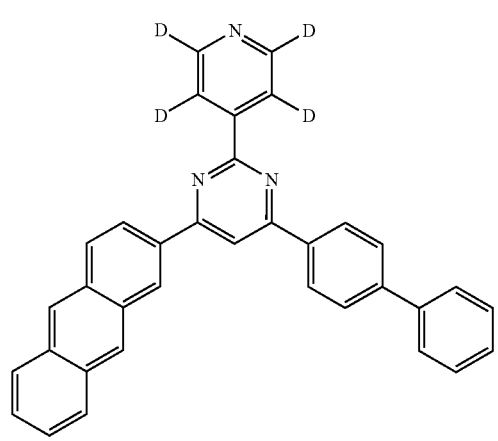
P123
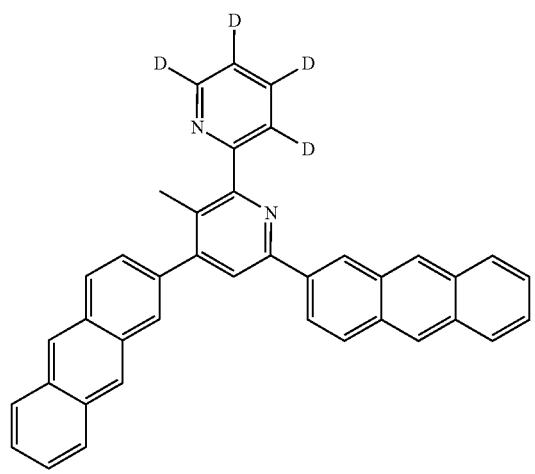

P124 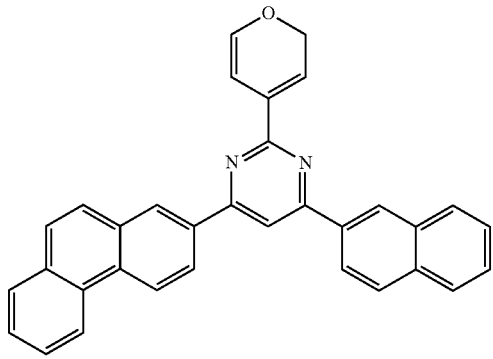
P128 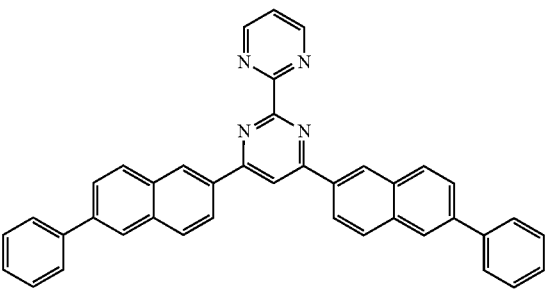
P125 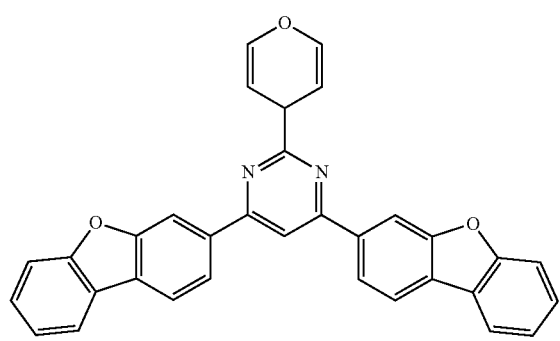
P130 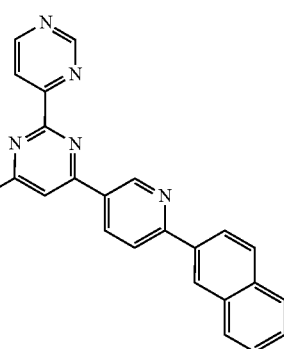
P126 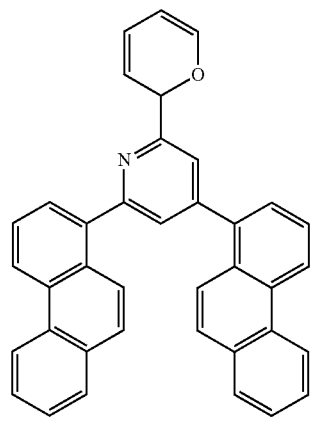
P129 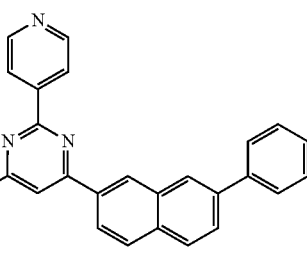
P127 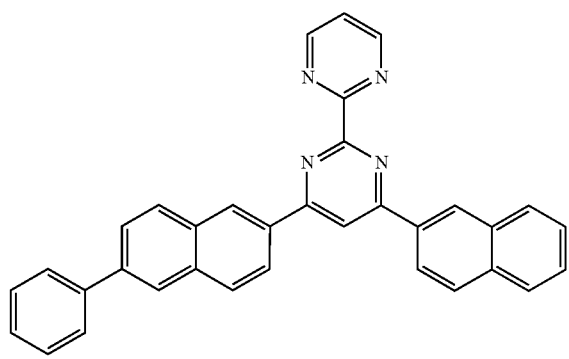
P131 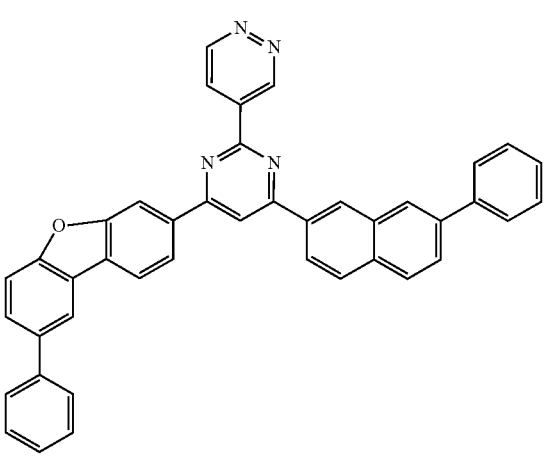

-continued

P132

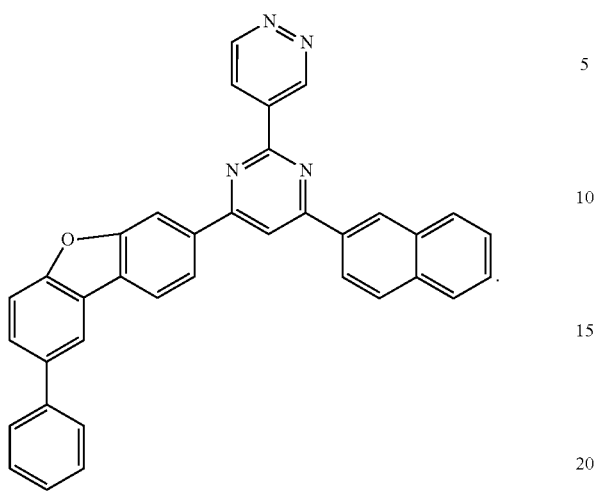

2. The nitrogen-heterocyclic compound according to claim 1, wherein the nitrogen-heterocyclic compound has a refractive index greater than or equal to 2.0 for visible light having a wavelength of 400 nm to 700 nm.

3. The nitrogen-heterocyclic compound according to claim 1, wherein the nitrogen-heterocyclic compound has an extinction coefficient less than or equal to 0.1 for visible light having a wavelength of 430 nm to 600 nm.

* * * * *